United States Patent
Nakae et al.

(10) Patent No.: US 12,023,173 B2
(45) Date of Patent: Jul. 2, 2024

(54) PAIN CLASSIFICATION AND MOMENTARY-PAIN DETERMINATION USING SPARSE MODELING

(71) Applicants: Osaka University, Osaka (JP);
PaMeLa, Inc., Osaka (JP);
NATIONAL INSTITUTE OF INFORMATION AND COMMUNICATIONS TECHNOLOGY, Koganei (JP)

(72) Inventors: Aya Nakae, Osaka (JP); Yasushi Naruse, Tokyo (JP); Takahiro Soshi, Tokyo (JP)

(73) Assignees: PAMELA, INC., Osaka (JP);
NATIONAL INSTITUTE OF INFORMATION AND COMMUNICATIONS TECHNOLOGY, Tokyo (JP); OSAKA UNIVERSITY, Osaka (JP)

( * ) Notice: Subject to any disclaimer, the term of this patent is extended or adjusted under 35 U.S.C. 154(b) by 1139 days.

(21) Appl. No.: 16/630,650

(22) PCT Filed: Jul. 13, 2018

(86) PCT No.: PCT/JP2018/026489
§ 371 (c)(1),
(2) Date: Jan. 13, 2020

(87) PCT Pub. No.: WO2019/013324
PCT Pub. Date: Jan. 17, 2019

(65) Prior Publication Data
US 2020/0253545 A1    Aug. 13, 2020

(30) Foreign Application Priority Data

Jul. 14, 2017  (JP) .................................. 2017-137723
Oct. 3, 2017   (JP) .................................. 2017-193501

(51) Int. Cl.
*A61B 5/00*    (2006.01)
*A61B 5/316*   (2021.01)
*A61B 5/377*   (2021.01)

(52) U.S. Cl.
CPC ............ *A61B 5/4824* (2013.01); *A61B 5/316* (2021.01); *A61B 5/377* (2021.01)

(58) Field of Classification Search
CPC ....... A61B 5/4824; A61B 5/316; A61B 5/377; A61B 5/7264; A61B 5/383; A61B 10/00
See application file for complete search history.

(56) References Cited

U.S. PATENT DOCUMENTS 4,570,640 A * 2/1986 Barsa ................... A61B 5/4047
                                                           600/554
9,533,148 B2 * 1/2017 Carcieri ............. A61N 1/36146
(Continued)

FOREIGN PATENT DOCUMENTS

EP        3263026 A1    1/2018
JP    2010-523226 B2   12/2010
(Continued)

OTHER PUBLICATIONS

Babiloni et al. ("Mapping of early and late human somatosensory evoked brain potentials to phasic galvanic painful stimulation", Human Brain Mapping, vol. 12(3), Mar. 2001, pp. 168-179 (Year: 2001).*
(Continued)

*Primary Examiner* — Jacqueline Cheng
*Assistant Examiner* — Tho Q Tran
(74) *Attorney, Agent, or Firm* — Muncy, Geissler, Olds & Lowe, P.C.

(57) ABSTRACT

A method is described for making determinations on or classifying the pain of an estimation subject on the basis of the brainwaves of the estimation subject. This method
(Continued)

includes: (a) stimulating the estimation subject at a plurality of levels of stimulation intensity; (b) acquiring brainwave data for the estimation subject; (c) extracting a brainwave feature quantity from the brainwave data or the analysis data; (d) for plugging the feature quantity into a Sparse model analysis, making the feature quantity approach a quantitative level and/or a qualitative level for pain, and estimating or making a determination on a pain level. Another method is described including comparing of brainwave data or analysis data from the 2,000 msec following the earliest of an induced brainwave component, an initial-event-related voltage component, and 250 msec after a target stimulus has been applied.

5 Claims, 36 Drawing Sheets

(56) References Cited

U.S. PATENT DOCUMENTS

| | | | | |
|---|---|---|---|---|
| 2003/0100931 | A1* | 5/2003 | Mullett | A61N 1/36071 607/46 |
| 2015/0196588 | A1* | 7/2015 | Kevil | A61P 25/04 424/718 |
| 2017/0056642 | A1* | 3/2017 | Moffitt | A61N 1/36071 |
| 2018/0193651 | A1* | 7/2018 | Annoni | A61B 5/4824 |

FOREIGN PATENT DOCUMENTS

| | | |
|---|---|---|
| WO | 2008/124566 A2 | 10/2008 |
| WO | WO2016136361 * | 1/2016 |

OTHER PUBLICATIONS

Pascali et al. ("Pain perception, somatosensory event-related potentials and skin conductance responses to painful stimuli in high, mid, and low hypnotizable subjects: effects of differential pain reduction strategies", Pain, vol. 83(3), Dec. 1999, pp. 499-508 (Year: 1999).*

Stern et al. (Persistent EEG overactivation in the cortical pain matrix of neurogenic pain patients, NeuroImage, vol. 31(2), Jun. 2006, pp. 721-731 (Year: 2006).*

Chen Andrew C.N et al: "Contact heat evoked potentials as a valid means to study nociceptive pathways in human subjects", Neuroscience Letters, vol. 316, No. 2, Dec. 1, 2001 (Dec. 1, 2001), pp. 79-82.

Supplementary European Search Report and European Search Opinion, issued in European Application No. EP18831435.5 dated Mar. 2, 2021, 7 pages.

Lancaster Jenessa, et al., "Decoding Acute Pain with Combined EEG and Physiological Data", 8th International IEEE/EMBS Conference on Neural Engineering (NER), 2017, 521-524.

Massimiliano Valeriani, et al., "Nociceptive contribution to the evoked potentials after painful intramuscular electrical stimulation", Neuroscience Research 60 (2008), 2007, 170-175.

PCT Search Report and Written Opinion issued in connection with corresponding PCT Application No. PCT/JP2018/026489 dated Jan. 17, 2019.

* cited by examiner

Example 2: Change in feature coefficient for model creation data excluding one subject and mean value of coefficients Example 2: Change in intercept for model creation data excluding one subject

FIG.10

Created differentiation model

Estimation value = Σ( Feature coefficient × Feature of each level ) + Intercept  0.0431

$$\begin{Bmatrix} Y1 \\ Y2 \\ Y3 \\ Y4 \end{Bmatrix} = \Sigma \left( \begin{Bmatrix} 0.1050 \\ 0.1891 \\ 0.4206 \\ 0.5317 \\ -2.1632 \\ 2.2206 \\ 0 \\ 0.7450 \\ 1.5147 \\ -0.5718 \\ 0.3920 \\ 2.4975 \\ -2.1362 \\ -1.7142 \\ 0 \\ -2.3888 \\ -2.3798 \\ 0 \\ 2.4303 \\ 0.4921 \\ 0 \\ -0.3525 \\ 0 \\ 0.0199 \end{Bmatrix} \times \begin{Bmatrix} x1 \\ X2 \\ X3 \\ X4 \\ X5 \\ X6 \\ X7 \\ X8 \\ X9 \\ X10 \\ X11 \\ X12 \\ X13 \\ X14 \\ X15 \\ X16 \\ X17 \\ X18 \\ X19 \\ X20 \\ X21 \\ X22 \\ X23 \\ X24 \end{Bmatrix} \right) + 0.0431$$

Classification of pain levels
i. Estimation value ≤ 50%: "weak (1)"
ii. Estimation value > 50%: "strong (2)"

FIG.11

Estimation value    Feature coefficient         Feature of each level                              Intercept $$= \sum \begin{pmatrix} 0.1050 \\ 0.1891 \\ 0.4206 \\ 0.5317 \\ -2.1632 \\ 2.2206 \\ 0 \\ 0.7450 \\ 1.5147 \\ -0.5718 \\ 0.3920 \\ 2.4975 \\ -2.1362 \\ -1.7142 \\ 0 \\ -2.3888 \\ -2.3798 \\ 0 \\ 2.4303 \\ 0.4921 \\ 0 \\ -0.3525 \\ 0 \\ 0.0199 \end{pmatrix} \times \begin{pmatrix} \text{weak 1} & \text{weak 2} & \text{strong 1} & \text{strong 2} \\ 0.5330 & 0.5620 & 0.6200 & 0.4490 \\ 0.7150 & 0.7870 & 0.6140 & 0.5040 \\ 0.7050 & 0.7070 & 0.6620 & 0.4990 \\ 0.7030 & 0.7520 & 0.6120 & 0.5090 \\ 0.9050 & 0.9670 & 0.9400 & 0.9110 \\ 0.9400 & 0.9330 & 0.9710 & 0.9230 \\ 0.9460 & 0.9530 & 0.9360 & 0.8740 \\ 0.9260 & 0.9370 & 0.9470 & 0.9020 \\ 0.5680 & 0.5650 & 0.8680 & 0.8050 \\ 0.9260 & 0.9760 & 0.9310 & 0.9150 \\ 0.9520 & 0.9410 & 0.9750 & 0.9490 \\ 0.9550 & 0.9440 & 0.9460 & 0.9160 \\ 0.9430 & 0.9480 & 0.9420 & 0.9080 \\ 0.6820 & 0.6970 & 0.8960 & 0.8320 \\ 0.9410 & 0.9800 & 0.9220 & 0.8980 \\ 0.9470 & 0.9160 & 0.9870 & 0.9370 \\ 0.9610 & 0.9570 & 0.9370 & 0.8800 \\ 0.8700 & 0.8800 & 0.9680 & 0.9240 \\ 0.6310 & 0.6410 & 0.9080 & 0.8240 \\ 0.9270 & 0.9830 & 0.9370 & 0.9290 \\ 0.9520 & 0.9340 & 0.9680 & 0.9400 \\ 0.9460 & 0.9430 & 0.9400 & 0.9110 \\ 0.9270 & 0.9270 & 0.9650 & 0.9090 \\ 0.6310 & 0.6410 & 0.9080 & 0.8240 \end{pmatrix} \end{pmatrix} + 0.0431$$

$$\begin{pmatrix} -1.2506 \\ -1.3132 \\ -0.5976 \\ -0.7706 \end{pmatrix}$$

Threshold value (50%): -1.011 i. Weak 1 estimation value: -1.2506 → weak (1)
ii. Weak 2 estimation value: -1.3132 → weak (1)
iii. Strong 1 estimation value: -0.5976 → strong (2)
iv. Strong 2 estimation value: -0.7706 → strong (2)

PAIN CLASSIFICATION AND MOMENTARY-PAIN DETERMINATION USING SPARSE MODELING

CROSS-REFERENCE TO RELATED APPLICATION

This application is a national stage application filed under 35 U.S.C. § 371, of International Patent Application No. PCT/JP2018/026489 filed Jul. 13, 2018, which claims the benefit of and priority to Japanese Application No. 2017-137723 filed Jul. 14, 2017 and Japanese Application No. 2017-193501 filed Oct. 3, 2017; the contents of each of which are hereby incorporated by reference in their entirety.

TECHNICAL FIELD

The present invention relates to classification of the quality and quantity of pain with little information by analyzing a biological signal such as a brainwave obtained from an object being estimated with sparse modeling. More specifically, the present invention relates to objective classification or differentiation of pain levels (e.g., weak pain, strong pain, or the like) having individual differences.

The present invention also relates to a technology of differentiating instantaneous pain using brainwaves. More specifically, the present invention relates to a technology of differentiating that instantaneous pain is occurring by differentiating a signal after a specific period of time has elapsed after stimulation.

BACKGROUND ART

Pain is intrinsically subjective, but objective evaluation thereof is desirable for therapy. Patients often suffer from an undesirable experience due to underestimation of pain. In this regard, a method for objectively estimating pain using brainwaves has been proposed (see, for example, Patent Literature 1). However, intensity of pain is subjective such that objective evaluation is challenging. Pain cannot be expressed simply as subjectively "painful" in terms of whether pain is especially unbearable pain or somewhat tolerable pain. Since expression thereof varies among individuals, objective evaluation is challenging. To observe the therapeutic effect, it is desirable to classify pain, but such a technology has not been provided.

Various sensations are often represented by a unidirectional vector. For example, pain is often distinguished as whether the pain is painful or not painful. The differentiation thereof is considered challenging for instantaneous pain.

CITATION LIST

Patent Literature

[PTL 1] Japanese National Phase PCT Laid-open Publication No. 2010-523226

SUMMARY OF INVENTION

Solution to Problem

The present invention provides a pain estimation method and apparatus, which is capable of objectively and accurately estimating pain of an object being estimated and readily classifying the quality and quantity thereof using sparse modeling. The present invention also provides a technology for generating a pain classifier for such pain classification.

The inventors discovered a differentiation technology that can differentiate instantaneous pain as a result of diligent study.

The present invention provides, for example, the following.

(1) A method of differentiating or classifying pain of an object being estimated based on a brainwave of the object being estimated, comprising:
   a) obtaining brainwave data for a model or analysis data thereof corresponding to stimulation intensity for a model;
   b) extracting a brainwave feature for a model from the brainwave data or analysis data thereof;
   c) setting a pain level of interest, introducing the brainwave feature for a model and the pain level into sparse model analysis, finding a suitable $\lambda$ value, and determining a parameter (partial regression coefficient) for the brainwave feature for a model and a constant (intercept) of an algorithm corresponding to the suitable $\lambda$ to generate a regression model;
   d) obtaining brainwave data for measurement or analysis data thereof of the object being estimated;
   e) extracting a brainwave feature for measurement from the brainwave data for measurement or analysis data thereof;
   f) calculating a corresponding pain level by fitting the brainwave feature for measurement to a regression model; and
   g) optionally displaying the pain level.

(2) A method comprising:
   c) providing a regression model for sparse model analysis of a pain level of the object being estimated;
   d) obtaining brainwave data for measurement or analysis data thereof of the object being estimated;
   e) extracting a brainwave feature for measurement from the brainwave data for measurement or analysis data thereof;
   f) calculating a corresponding pain level by fitting the brainwave feature for measurement to a regression model; and
   g) optionally displaying the pain level.

(3) A method for generating a regression model for differentiating or classifying pain of an object being estimated based on a brainwave of the object being estimated, comprising:
   a) obtaining brainwave data for a model or analysis data thereof corresponding to stimulation intensity for a model;
   b) extracting a brainwave feature for a model from the brainwave data or analysis data thereof; and
   c) setting a pain level of interest, introducing the brainwave feature for a model and the pain level into sparse model analysis, finding a suitable $\lambda$, and determining a parameter (partial regression coefficient) for the brainwave feature for a model and a constant (intercept) of an algorithm corresponding to the suitable $\lambda$ to generate a regression model.

(4) The method of any one of items 1 to 3, wherein the regression model is validated by split cross validation.

(5) The method of item 4, wherein the split cross validation is 10-fold cross validation.

(6) The method of any one of items 1 to 5, wherein the brainwave data for a model is brainwave data from an object being estimated.

(7) The method of any one of items 1 to 5, wherein the brainwave data for a model is brainwave data from an object that is different from an object being estimated.

(8) The method of item 7, wherein the regression model, after the generation thereof, further calibrates the object being estimated.

(9) The method of any one of items 1 to 8, wherein the pain level comprises at least two types and/or at least two patterns of pain.

(10) The method of any one of items 1 to 9, wherein the regression model is generated for a large number of subjects.

(11) The method of item 1, wherein there are at least two types of the brainwave features.

(12) An apparatus for differentiating or classifying pain of an object being estimated based on a brainwave of the object being estimated, comprising:
  A) a model data obtaining unit for obtaining brainwave data for a model or analysis data thereof corresponding to stimulation intensity for a model;
  B) a model feature extraction unit for extracting a brainwave feature for a model from the brainwave data or analysis data thereof;
  C) a regression model generation unit for setting a pain level of interest, introducing the brainwave feature for a model and the pain level into sparse model analysis, finding a suitable A, and determining a parameter (partial regression coefficient) for the brainwave feature for a model and a constant (intercept) of an algorithm corresponding to the suitable A to generate a regression model;
  D) a measurement data obtaining unit for obtaining brainwave data (for measurement) or analysis data thereof of the object being estimated;
  E) a measurement feature extraction unit for extracting a brainwave feature for measurement from the brainwave data for measurement or analysis data thereof;
  F) a pain level calculation unit for calculating a corresponding pain level by fitting the brainwave feature for measurement to a regression model; and
  G) optionally a pain level display unit for displaying the pain level.

(13) An apparatus for differentiating or classifying pain of an object being estimated based on a brainwave of the object being estimated, comprising:
  C) a regression model provision unit for providing a regression model for sparse model analysis of a pain level of the object being estimated;
  D) a measurement data obtaining unit for obtaining brainwave data (for measurement) or analysis data thereof of the object being estimated;
  E) a measurement feature extraction unit for extracting a brainwave feature for measurement from the brainwave data for measurement or analysis data thereof;
  F) a pain level calculation unit for calculating a corresponding pain level by fitting the brainwave feature for measurement to a regression model; and
  G) optionally a pain level display unit for displaying the pain level.

(14) An apparatus for generating a regression model for differentiating or classifying pain of an object being estimated based on a brainwave of the object being estimated, comprising:
  A) a model data obtaining unit for obtaining brainwave data for a model or analysis data thereof corresponding to stimulation intensity for a model;
  B) a feature extraction unit for extracting a brainwave feature for a model from the brainwave data or analysis data thereof; and
  C) a regression model generation unit for setting a pain level of interest, introducing the brainwave feature for a model and the pain level into sparse model analysis, finding a suitable A, and determining a parameter (partial regression coefficient) for the brainwave feature for a model and a constant (intercept) of an algorithm corresponding to the suitable A to generate a regression model.

(15) The apparatus of any one of items 12 to 14, comprising a characteristic of any one or more of items 4 to 11.

(16) A program for making a computer execute a method of differentiating or classifying pain of an object being estimated based on a brainwave of the object being estimated, the method comprising:
  a) obtaining brainwave data for a model or analysis data thereof corresponding to stimulation intensity for a model;
  b) extracting a brainwave feature for a model from the brainwave data or analysis data thereof;
  c) setting a pain level of interest, introducing the brainwave feature for a model and the pain level into sparse model analysis, finding a suitable A, and determining a parameter (partial regression coefficient) for the brainwave feature for a model and a constant (intercept) of an algorithm corresponding to the suitable A to generate a regression model;
  d) obtaining brainwave data (for measurement) or analysis data thereof of the object being estimated;
  e) extracting a brainwave feature for measurement from the brainwave data for measurement or analysis data thereof;
  f) calculating a corresponding pain level by fitting the brainwave feature for measurement to a regression model; and
  g) optionally displaying the pain level.

(17) A program for making a computer execute a method of differentiating or classifying pain of an object being estimated based on a brainwave of the object being estimated, the method comprising:
  c) providing a regression model for sparse model analysis of a pain level of the object being estimated;
  d) obtaining brainwave data (for measurement) or analysis data thereof of the object being estimated;
  e) extracting a brainwave feature for measurement from the brainwave data for measurement or analysis data thereof;
  f) calculating a corresponding pain level by fitting the brainwave feature for measurement to a regression model; and
  g) optionally displaying the pain level.

(18) A program for making a computer execute a method for generating a regression model for differentiating or classifying pain of an object being estimated based on a brainwave of the object being estimated, comprising:
  a) obtaining brainwave data for a model or analysis data thereof corresponding to stimulation intensity for a model;
  b) extracting a brainwave feature for a model from the brainwave data or analysis data thereof; and
  c) setting a pain level of interest, introducing the brainwave feature for a model and the pain level into sparse model analysis, finding a suitable A, and determining a parameter (partial regression coefficient) for the brainwave feature for a model and a constant (intercept) of an algorithm corresponding to the suitable A to generate a regression model.

(19) The program of any one of items 16 to 18, comprising a characteristic of any one or more of items 4 to 11.

(20) A recording medium storing a program for making a computer execute a method of differentiating or classifying pain of an object being estimated based on a brainwave of the object being estimated, comprising:
  a) obtaining brainwave data for a model or analysis data thereof corresponding to stimulation intensity for a model;
  b) extracting a brainwave feature for a model from the brainwave data or analysis data thereof;
  c) setting a pain level of interest, introducing the brainwave feature for a model and the pain level into sparse model analysis, finding a suitable A, and determining a parameter (partial regression coefficient) for the brainwave feature for a model and a constant (intercept) of an algorithm corresponding to the suitable A to generate a regression model;
  d) obtaining brainwave data (for measurement) or analysis data thereof of the object being estimated;
  e) extracting a brainwave feature for measurement from the brainwave data for measurement or analysis data thereof;
  f) calculating a corresponding pain level by fitting the brainwave feature for measurement to a regression model; and
  g) optionally displaying the pain level.

(21) A recording medium storing a program for making a computer execute a method of differentiating or classifying pain of an object being estimated based on a brainwave of the object being estimated, the method comprising:
  c) providing a regression model for sparse model analysis of a pain level of the object being estimated;
  d) obtaining brainwave data (for measurement) or analysis data thereof of the object being estimated;
  e) extracting a brainwave feature for measurement from the brainwave data for measurement or analysis data thereof;
  f) calculating a corresponding pain level by fitting the brainwave feature for measurement to a regression model; and
  g) optionally displaying the pain level.

(22) A recording medium storing a program for making a computer execute a method for generating a regression model for differentiating or classifying pain of an object being estimated based on a brainwave of the object being estimated, the method comprising:
  a) obtaining brainwave data for a model or analysis data thereof corresponding to stimulation intensity for a model;
  b) extracting a brainwave feature for a model from the brainwave data or analysis data thereof; and
  c) setting a pain level of interest, introducing the brainwave feature for a model and the pain level into sparse model analysis, finding a suitable $\lambda$, and determining a parameter (partial regression coefficient) for the brainwave feature for a model and a constant (intercept) of an algorithm corresponding to the suitable $\lambda$ to generate a regression model.

(23) The recording medium of any one of items 20 to 22, comprising a characteristic of any one or more of items 4 to 11.

The present invention further provides, for example, the following.

(A1) A method of differentiating or evaluating pain, comprising comparing brainwave data or analysis data thereof from some or all of a period between the earliest point among evoked brainwave potential, early event related potential, and 250 msec and 2000 msec from application of target stimulation with brainwave or analysis data thereof after the same time from application of reference stimulation.

(A2) The method of item A1, comprising, as criteria of determination, whether the brainwave data from a period between the earliest point among evoked brainwave potential, early event related potential, and 250 msec and 2000 msec has a persistent property.

(A3) The method of item A1 or A2, wherein the brainwave data or analysis data thereof comprises brainwave data or analysis data thereof in some or all of a range from an intermediate time frame to 2000 msec.

(A4) The method of item A3, wherein the intermediate time frame comprises a value in a range between 250 msec to 600 msec.

(A5) The method of any one of items A1 to A4, wherein the some or all comprises at least a 100 msec range.

(A6) The method of item A5, wherein if a statistically significant difference is found with at least 100 msec range, it is determined that persistence is found in the at least 100 msec range.

(A7) The method of any one of items A1 to A6, wherein the comparing comprises: measuring whether there is a persistent period where a value of brainwave data or analysis data thereof obtained from the target stimulation is different from a value of brainwave data or analysis data thereof obtained from the reference stimulation and, if there is the different persistent period, whether the values would be the same value again after becoming different; and if there is the persistent period and the values would not be the same value again, determining that there is unpleasant pain.

(A8) The method of any one of items A1 to A7, wherein the brainwave data or analysis data thereof is either potential, a persistent period, or a combination thereof.

(A9) The method of any one of items A1 to A8, wherein the differentiation of pain is differentiation of a degree of unpleasantness of pain.

(A10) The method of any one of items A1 to A9, wherein the brainwave data or analysis data thereof is compared throughout the entire period from the earliest point among evoked brainwave potential, early event related potential, and 250 msec to 2000 msec.

(A11) The method of any one of items A1 to A10, further comprising analyzing the compared data using sigmoid function fitting.

(A12) The method of any one of items A1 to A11, wherein the differentiation judges a positive component of brainwave data or analysis data thereof.

(A13) The method of item A12, wherein it is judged that there is pain when the positive component also persists after an intermediate time frame.

(A14) A program for making a computer execute a method of differentiating or evaluating pain, the method comprising
  comparing brainwave data or analysis data thereof from some or all of a period between the earliest point among evoked brainwave potential, early event related potential, and 250 msec and 2000 msec from application of target stimulation with brainwave or analysis data thereof after the same time from application of reference stimulation.

(A14A) The program of item A14, further comprising one or more features of items A1 to A13.

(A15) A recording medium for storing a program for making a computer execute a method of differentiating or evaluating pain, the method comprising comparing brainwave data or analysis data thereof from some or all of a period between the earliest point among evoked brainwave potential, early event related potential, and 250 msec and 2000 msec from application of target stimulation with brainwave or analysis data thereof after the same time from application of reference stimulation.

(A15A) The recording medium of item A15, further comprising one or more characteristics of items A1 to A13.

(A16) A system or apparatus for differentiating or evaluating pain, comprising:
a brainwave data input unit for inputting brainwave data or analysis data thereof; and
an analysis unit for comparing brainwave data or analysis data thereof from some or all of a period between the earliest point among evoked brainwave potential, early event related potential, and 250 msec and 2000 msec from application of target stimulation with brainwave or analysis data thereof after the same time from application of reference stimulation.

(A16A) The system or apparatus of item A16, further comprising one or more features of items A1 to A13.

The present invention is intended so that one or more of the aforementioned characteristics can be provided not only as the explicitly disclosed combinations, but also as other combinations thereof. Additional embodiments and advantages of the invention are recognized by those skilled in the art by reading and understanding the following detailed description as needed.

Advantageous Effects of Invention

The present invention can classify pain readily with fewer parameters. In a preferred embodiment, the present invention can distinguish the quality of various pain with parameters that are obtained and acquired. With this data, pain can be classified, various treatment can be minimally administered, or therapeutic effects can be classified.

The present invention can also differentiate instantaneous pain. The present invention can differentiate between instantaneous pain and delayed pain, and administer more detailed therapy or surgery matching subjective evaluation, so that the present invention is useful in the medical industry.

BRIEF DESCRIPTION OF DRAWINGS

FIG. 10 shows a multiple regression model for pain differentiation created by 10-fold cross validation in Example 2. A pain index estimated by a differentiation model is categorized into pain levels by a threshold value (e.g., 50%).

FIG. 11 shows pain level differentiation accuracy by threshold value (50%) and pain estimation values of a subject calculated by the pain differentiation model in Example 2.

DESCRIPTION OF EMBODIMENTS

Figure 1A:
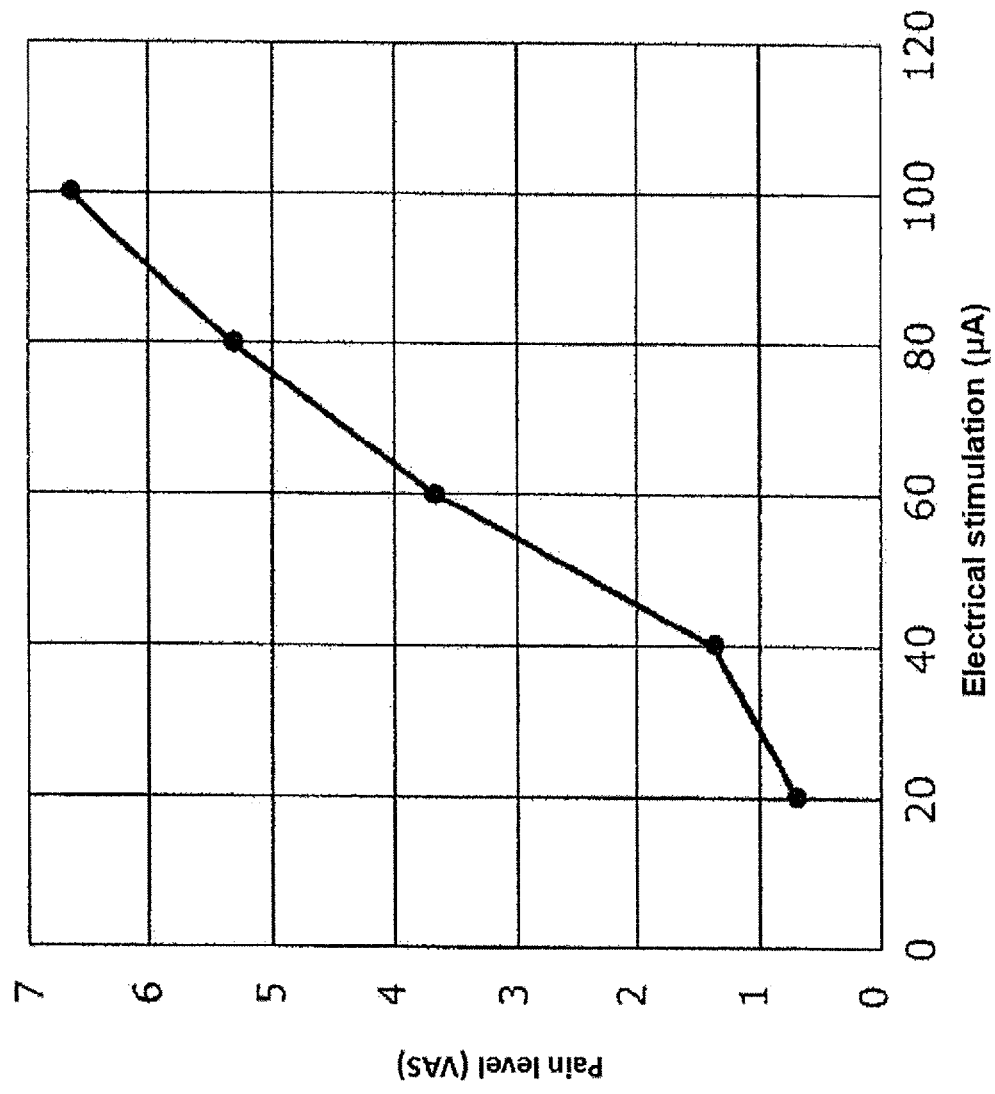
FIG. 1A is a graph showing the relationship between electrical stimulation and pain levels (VAS).

The present invention is explained hereinafter. Throughout the entire specification, a singular expression should be understood as encompassing the concept thereof in the plural form, unless specifically noted otherwise. Thus, singular articles (e.g., "a", "an", "the", and the like in the case of English) should also be understood as encompassing the concept thereof in the plural form, unless specifically noted otherwise. The terms used herein should also be understood as being used in the meaning that is commonly used in the art, unless specifically noted otherwise. Thus, unless defined otherwise, all terminologies and scientific technical terms that are used herein have the same meaning as the general understanding of those skilled in the art to which the present invention pertains. In case of a contradiction, the present specification (including the definitions) takes precedence.

Definition

The terms and the general technologies used herein are first explained.

As used herein, "object" is used synonymously with patient and subject and refers to any organism or animal which is subjected to the technology herein such as pain measurement and brainwave measurement. An object is preferably, but is not limited to, humans. As used herein, an object may be referred to an "object being estimated" when estimating pain, but this has the same meaning as object or the like.

As used herein, "brainwave" has the meaning that is commonly used in the art and refers to a current generated by a difference in potential due to neurological activity of the brain when a pair of electrodes is placed on the scalp.

Brainwave encompasses electroencephalogram (EEG), which is obtained from deriving and recording temporal changes in the current. A wave with an amplitude of about 50 μV and a frequency of approximately 10 Hz is understood to be the primary component at rest. This is referred to as an α wave. During mental activity, it is understood that α waves are suppressed and a fast wave with a small amplitude of 17 to 30 Hz appears, which is referred to as a β wave. During a period of shallow sleep, it is understood that α waves gradually decrease, and θ waves of 4 to 8 Hz appear. During a deep sleep, it is understood that δ waves of 1 to 4 Hz appear. These brainwaves can be denoted by a specific amplitude and frequency (power). Analysis of amplitudes can be important in the present invention.

As used herein, "brainwave data" is any data related to brainwaves (also referred to as "amount of brain activity", "brain feature", or the like), such as amplitude data (EEG amplitude, frequency property, or the like). "Analysis data" from analyzing such brainwave data can be used in the same manner as brainwave data, so that such data is collectively referred to as "brainwave data or analysis data thereof" herein. Examples of analysis data include mean amplitude (e.g., Fz, Cz, C3, C4), frequency power (e.g., Fz(δ), Fz(θ), Fz(a), Fz(β), Fz(γ), Cz(δ), Cz(θ), Cz(a), Cz(β), Cz(γ), C3(δ), C3(θ), C3(α), C3(β), C3(γ), C4(δ), C4(θ), C4(α), C4(β), and C4(γ)) and the like. Of course, this does not exclude other data that are commonly used as brainwave data or analysis data thereof.

As used herein, "amplitude data" is one type of "brainwave data" and refers to data for amplitudes of brainwaves. This is also referred to as simply "amplitude" or "EEG amplitude". Since such amplitude data is an indicator of brain activity, such data can also be referred to as "brain activity data", "amount of brain activity", or the like. Amplitude data can be obtained by measuring electrical signals of a brainwave and is indicated by potential (can be indicated by μV or the like). Amplitude data that can be used includes, but are not limited to, mean amplitude.

As used herein, "frequency power" expresses frequency components of a waveform as energy and is also referred to as power spectrum. Frequency power can be calculated by extracting and calculating frequency components of a signal embedded in a signal contained in noise within a time region by utilizing fast Fourier transform (FFT) (algorithm for calculating discrete Fourier transform (DFT) on a computer at high speeds). FFT on a signal can, for example, use the function periodogram in MATLAB to normalize the output thereof and calculate the power spectrum density PSD or power spectrum, which is the source of measurement of power. PSD indicates how power of a time signal is distributed with respect to frequencies. The unit thereof is watt/Hz. Each point in PSD is integrated over the range of frequencies where the point is defined (i.e., over the resolution bandwidth of PSD) to calculate the power spectrum. The unit of a power spectrum is watt. The value of power can be read directly from power spectrum without integration over the range of frequencies. PSD and power spectrum are both real numbers, so that no phase information is included. In this manner, frequency power can be calculated with a standard function in MATLAB.

As used herein, "pain" refers to a sensation that is generated as stimulation, generally upon intense injury such as damage/inflammation to a body part. In humans, pain is encompassed by common sensations as a sensation accompanying strong unpleasant feeling. In addition, cutaneous pain and the like also has an aspect as an external receptor to a certain degree, which plays a role in determining the quality such as hardness, sharpness, hotness (thermal pain), coldness (cold pain), or spiciness of an external object in cooperation with other skin sensation or taste. The sensation of pain of humans can occur at almost any part of the body (e.g., pleura, peritoneum, internal organs (visceral pain, excluding the brain), teeth, eyes, ears, and the like) besides the skin and mucous membrane, which can all be sensed as a brainwave or a change thereof in the brain. Additionally, internal sensation of pain represented by visceral pain is also encompassed by sensation of pain. The aforementioned sensation of pain is referred to as somatic pain relative to visceral pain. In addition to somatic pain and visceral pain, sensation of pain called "referred pain", which is a phenomenon where pain is perceived at a surface of a site that is different from a site that is actually damaged, is also reported. The present invention is also capable of the classification thereof, as well as classification of various pain types from the viewpoint of pleasant/unpleasant.

For sensation of pain, there are individual differences in sensitivity (pain threshold), as well as qualitative difference due to a difference in the receptor site or how a pain stimulation occurs. Sensation of pain is classified into dull pain, sharp pain, and the like, but sensation of pain of any type can be measured, estimated, and classified in this disclosure. The disclosure is also compatible with fast sensation of pain (A sensation of pain), slow sensation of pain (B sensation of pain), (fast) topical pain, and (slow) diffuse pain. The present invention is also compatible with abnormality in sensation of pain such as hyperalgesia. Two nerve fibers, i.e., "Aδ fiber" and "C fiber", are known as peripheral nerves that transmit pain. For example, when a hand is hit, the initial pain is transmitted as sharp pain from a clear origin (primary pain; sharp pain) by conduction through the Aδ fiber. It is understood that pain is then conducted through the C fiber to be felt as throbbing pain (secondary pain; dull pain) with an unclear origin. Pain is classified into "acute pain" lasting 4 to 6 weeks or less and "chronic pain" lasting 4 to 6 weeks or more.

Pain is an important vital sign along with pulse, body temperature, blood pressure, and breathing, but is difficult to express as objective data. Representative pain scales VAS (Visual Analogue Scale) and faces pain rating scale are subjective evaluation methods that cannot compare pain between patients. Meanwhile, the inventors have focused on brainwaves which are hardly affected by the peripheral circulatory system as an indicator for objectively evaluating pain, arriving at the conclusion that the type of pain can be differentiated and classified by observing the change during latency/amplitude in response to pain stimulation and applying sparse analysis. Observation of the change during latency/amplitude in response to pain stimulation by the inventors lead to classification of types of pain (pleasant/unpleasant). Instantaneous stimulation and persistent stimulation can also be classified in this manner.

As used herein, "instantaneous pain" refers to pain that feels like being pierced by a needle, which is a type of pain wherein a signal appears at evoked potential manifested at 50 to 200 ms in synchronization with isolated stimulation. Meanwhile, breakthrough pain is a term used in palliative care, referring to, unlike instantaneous pain, transient strong pain, which is a concept including persistent pain used herein.

Breakthrough pain is defined as "transient pain or increase in pain that occurs regardless of the presence/absence or degree of persistent pain or the presence/absence of use of analgesic".

Persistent pain generally refers to pain that is not an isolated pain, or pain that is not sensed as isolated due to isolated pain sequentially occurring, where it is difficult to recognize synchronicity of evoked potential with isolated pain, and a signal is not emitted in a form such as event related potential. Most clinical pain is encompassed in this category. The same applies at the animal level. Meanwhile, instantaneous pain can be considered as a change that can be viewed as an increase in amplitude, and persistent pain can be considered as pain which can manifest as a decrease in amplitudes.

Figure 18:
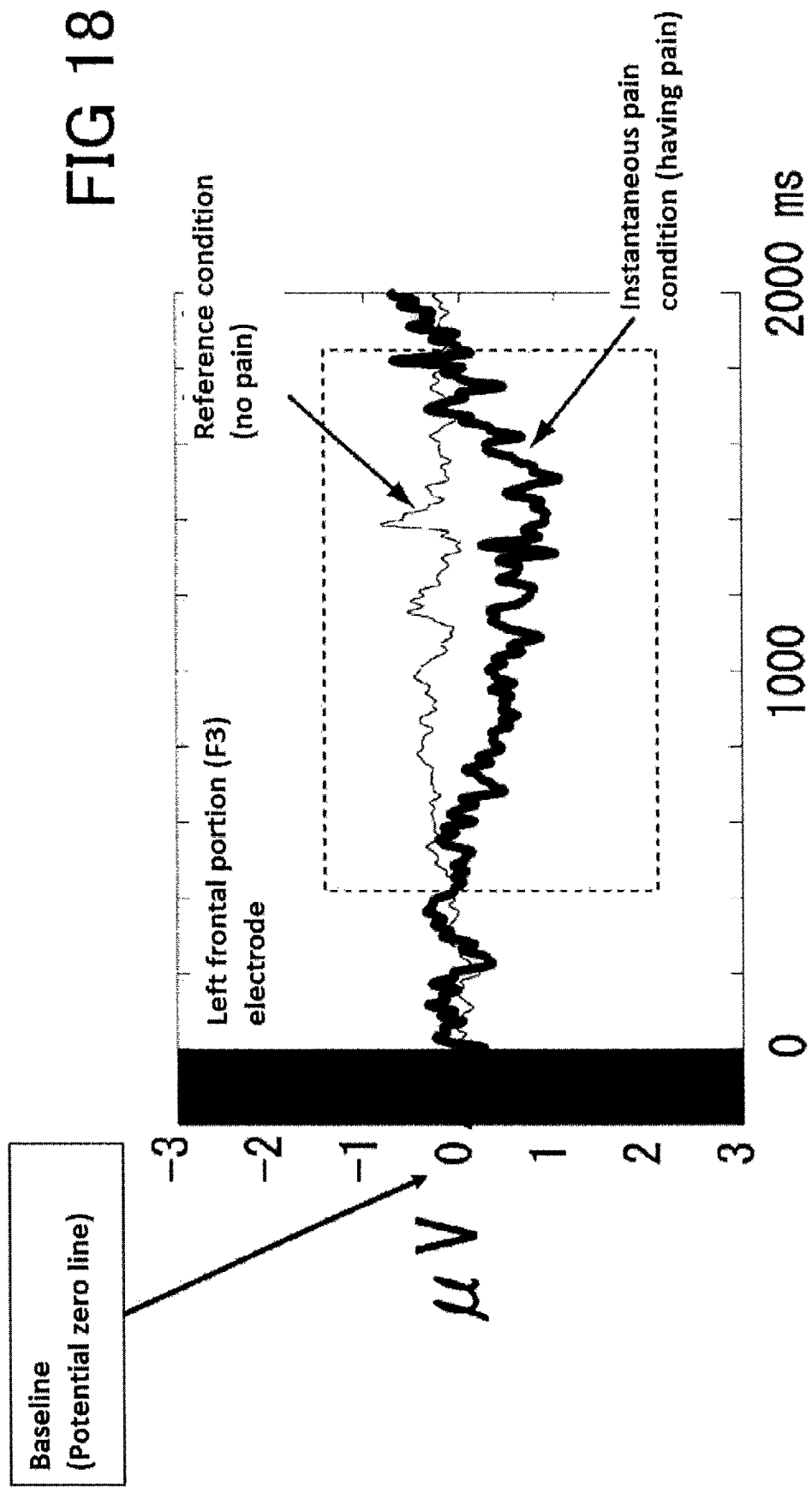
FIG. 18 shows an example of a persistent signal (property) of the left frontal portion (F3) found in the invention. Generally, the peak time for intermediate positive, late positive components, or the like such as P300 can change due to difficult of the task. When there is no persistence, there is a clear peak, returning to the baseline (potential zero line). The persistent component of the invention certainly starts at about 400 msec, but the effect continues for a very long time. A peak is not found in the vicinity of 400 msec, but is shifted to the vicinity of 1500 msec. The persistent component can be used as a template, regressed to the brainwave data online, and a point where an approximation index ($R^2$ or correlation coefficient) is high can be found to identify the point where incidental instantaneous pain occurs.

One of the important points of the invention is that instantaneous pain, which is different from persistent pain, can be distinguished to facilitate judgment on suitable therapy. Therefore, it is important that "pain" can be clearly categorized around the concept of "therapy". As shown in FIG. 18, persistent brainwave feature synchronized with instantaneous pain exhibits a gradual shift to the positive direction in the range of 2000 msec. Thus, the point where instantaneous pain has occurred can be identified by forming a template for the change pattern as shown in FIG. 18, continuously regressing online, and identifying the point with high degree of approximation.

One of the important points of the invention is that pain can be effectively determined and classified with few parameters for the determination of pain.

One of the important points of the present invention is in the ability to distinguish whether pain is pain "requiring therapy", rather than the intensity itself. Therefore, it is important that "pain" can be clearly categorized based on the concept of "therapy". For example, this leads to "qualitative" classification of pain such as "pleasant/unpleasant" or "unbearable". For example, the position of a "pain classifier", inflection point, range of the classification value, and the relationship thereof can be defined. In addition to a case of n=2, cases where n 3 or greater can also be envisioned. When n is 3 or greater, pain can be separated into "not painful", "comfortable pain", and "painful". For example, pain can be differentiated as pain that is "unbearable, need therapy", "moderate", or "painful, but not bothersome". Differentiation using a regression model calculated by sparse modeling of the invention can distinguish "unbearable" and "painful but bearable with no need for therapy".

As used herein, "subjective pain sensation level" refers to the level of sensation of pain of an object, and can be expressed by conventional technology such as computerized visual analog scale (COVAS) or other known technologies such as Support Team Assessment Schedule (STAS-J), Numerical Rating Scale (NRS), Faces Pain Scale (FPS), Abbey pain scale (Abbey), Checklist of Nonverbal Pain Indicators (CNPI), Non-communicative Patient's Pain Assessment Instrument (NOPPAIN), Doloplus 2, or the like. Such a subjective pain level sensation level can be applied to evaluation of instantaneous pain.

As used herein, "stimulation" refers to anything that causes some type of a reaction to an object. If the object is an organism, stimulation refers to a factor resulting in a temporarily change in the physiological activity of the organism or a portion thereof. Events related to sensation of pain presented as specific examples of "stimulation" includes any stimulation that can cause sensation of pain. Examples thereof include electrical stimulation, cold stimulation, thermal stimulation, physical stimulation, chemical stimulation, and the like. In the present invention, stimulation used in generating a pain classifier can be any stimulation, but temperature stimulation (cold or hot stimulation) or electrical stimulation is generally used. 3 or more types of stimulation levels are generally used, preferably 4 or more types, more preferably 5 or more types, and still more preferably 6 or more types, or more types of stimulation can be used. For temperature stimulation such as low temperature stimulation, temperature can be reduced by sense as appropriate, for example, in the range of 10° C. to −15° C. Stimulation of 6 types of temperature levels can be generated by reducing the temperature in 5° C. increments to obtain six temperatures. Evaluation of stimulation can be matched with subjective pain sensation levels using, for example, conventional technology such as computerized visual analog scale (COVAS) or other known technologies such as Support Team Assessment Schedule (STAS-J), Numerical Rating Scale (NRS), Faces Pain Scale (FPS), Abbey pain scale (Abbey), Checklist of Nonverbal Pain Indicators (CNPI), Non-communicative Patient's Pain Assessment Instrument (NOPPAIN), Doloplus 2, or the like. Examples of values that can be employed as stimulation intensity include nociceptive threshold (threshold for generating neurological impulses in the nociceptive fiber), pain detection threshold (intensity of nociceptive stimulation that can be sensed as pain by humans), pain tolerance threshold (strongest stimulation intensity among nociceptive stimulation that is experimentally tolerable by humans), and the like.

For psychological conditions, stimulation can be sensed by, for example, the five senses (sight, hearing, taste, touch, and smell). Examples thereof include any factor that is processed as information in the brain, any factor that can be mentally sensed such as social stress, and the like.

As used herein, "evoked (brainwave) potential" refers to a component of a brainwave evoked in response to exogenous stimulation. There are positive and negative brainwaves. Examples of positive potential include P1 (P100) (wave), and examples of negative potential include N1 (N100) (wave) and N125 (see Donchin, E., Ritter, W., & McCallum, C. (1978). Cognitive psychophysiology: The endogenous components of the ERP. In E. Callaway, P. Tueting, & S. Koslow (Eds.), Brain event-related potentials in man (pp. 349-441). New York: Academic Press). While they reflect the processing procedure in response to physical stimulation, it is understood that event related potential is generated by changes in a higher order processing procedure, particularly memory, expectation, attention, or psychological state.

As used herein, "event-related potential" (ERP) refers to an endogenous brainwave component. There are positive and negative brainwaves. Examples positive potential include P2 (P200) (wave), and examples of negative potential include N2 (N200) (wave). Event related potential chronologically occurs after evoked brainwave potential (Donchin et al., supra). This can be considered as a reaction of brain measured in some form as a result of thought or cognition. More specifically, event-related potential can be considered a typical electrophysiological reaction to internal/external stimulation. ERP is measured by brainwaves. The same concept using magnetoencephalography (MEG) is known as event-related field (ERF), which can be analyzed in the same manner as ERP.

As used herein, "P100" or "P1" refers to a positive evoked brainwave potential and is also known as the first positive evoked brainwave potential.

As used herein, "N100" or "N1" refers to a negative evoked brainwave potential and is also known as the first negative evoked brainwave potential, occurring after P100.

As used herein, "P200" or "P2" is also known as positive early event related potential. This generally occurs after P1 and N1.

As used herein, "N200" or "N2" is an early negative event related potential that occurs after P200.

As used herein, "P300" or "P3" refers to a positive intermediate event related potential. This generally occurs after P200 and N200. Conventional P300 has a peak, observed as a transient potential component. In the present invention, a potential component with a persistent property was found at a position overlapping with P300 or thereafter. This was found to be related to instantaneous pain. This could not be expected from conventional findings. Moreover, an indicator that is useful for therapy is provided. Therefore, the persistent component found in the present invention can be referred to as a "persistent positive component" comprising "persistent P300".

Figure 17:
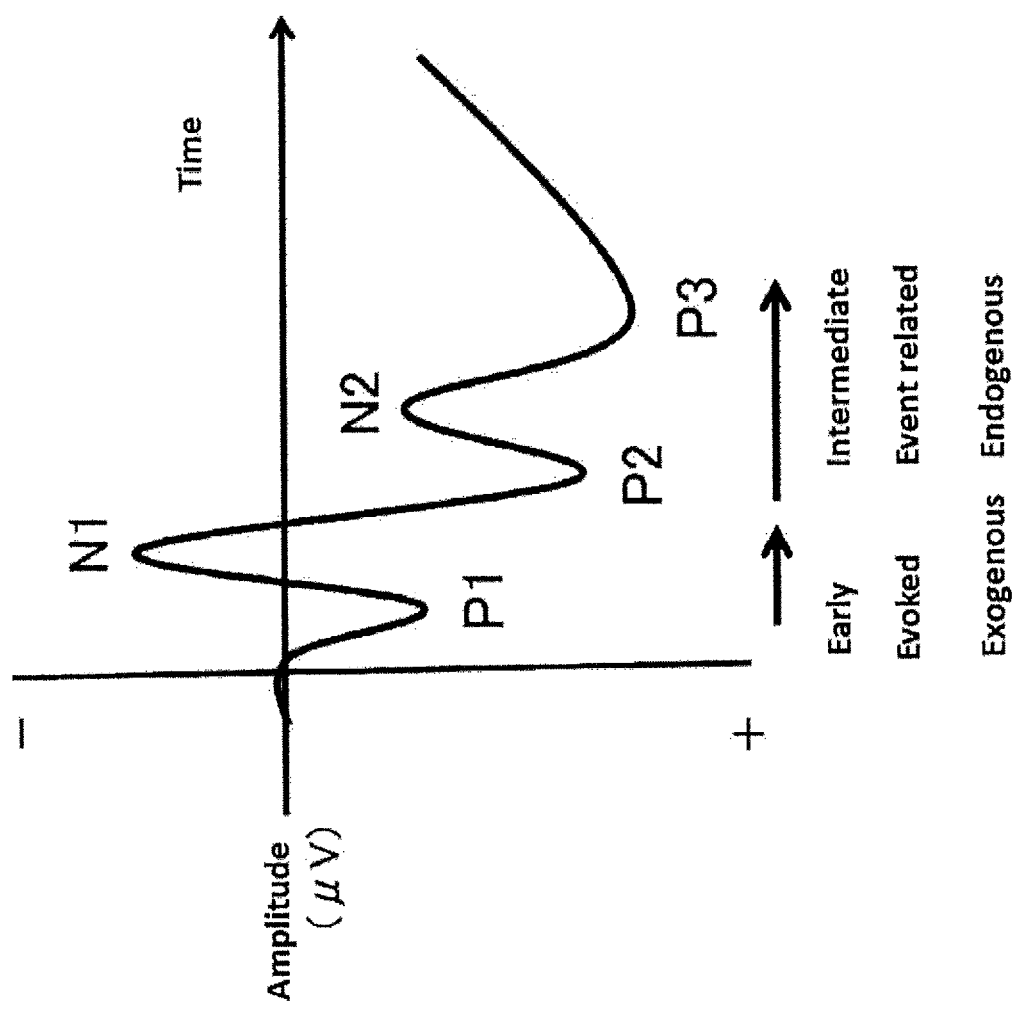
FIG. 17 shows a schematic diagram for evoked brainwave potentials and event related potentials. Examples of P1, P2, N1, N2, and P3 are shown.

Both "evoked brainwave potential" and "early event related potential" often occur before 250 msec. Generally, "evoked brainwave potential" first occurs, and "event related potential" follows. If the potential occurs after 250 msec in relation to the objective of the invention, measurement range can be determined with 250 msec as the starting point (see Cul et al. (2007). Brain Dynamics Underlying the Nonlinear Threshold for Access to Consciousness. PLoS Biol 5(10): e260). Evoked and event related potential such as N100 and P200 may not be observed clearly due to how stimulation had been received, reduction in degree of alertness, or the like, but is present as long as the subject is not in a vegetable state without a functioning cerebral neocortex. Thus, 250 msec can be set as the starting period of measurement when convenience. P200 components are components reflecting selective attention, which are like an entry point of brainwave components of high order cognition that starts manifesting in the intermediate time frame. The temporal relationship of P1, N1, P2, N2, P3, and the like are illustrated in FIG. 17. FIG. 17 is a temporal change in the time frame of event related potential (after P2) from evoked potential. Before the evoked potential before P1 (<100 msec) is a more finely divided reaction of the deeper part of the brain (P50, P25, and the like). Thus, the target of measurement of the invention can be defined as the earliest point among "negative and positive exogenous evoked brainwave potential", "early negative and positive endogenous event related potential" and 250 msec to 2000 msec.

P300 (P3) is considered as the third positive ERP component following P100 and P200. At peak latency, this often appears around 300 msec, but can be delayed several hundreds of milliseconds depending on the cognition load or details of processing. It is conjectured that there are two types of P300, one of which is referred to as P3a that is a reaction to a novel stimulation, i.e., a startle response to novel stimulation, manifesting mainly at the frontal portion. On the other hand, P3b is a conscious response to a target of attention and is not observed unless attention is paid. P3b appears mainly at the central parietal portion and has a peak time that is slightly later than P3a. Although not wishing to be bound by any theory, the persistent positive component used herein and P300 are not directly related. The positive component can be referred to as "persistent P300" in the sense of being the third positive component.

Furthermore, P300 is reported as not having a property of continuously changing with respect to a stimulation property unlike brain activity such as early evoked potential (N100). For example, when the stimulation intensity increases, potential "continuously" changes for excitable component of evoked component N100, whereas P300 exhibits a "sigmoid function pattern" gradually approximating discreteness of having conscious response and no conscious response (Cul et al. (2007). Brain Dynamics Underlying the Nonlinear Threshold for Access to Consciousness. PLoS Biol 5(10): e260). When this finding is applied to the present invention for pain, this is an important finding in that the presence of this component indicates "aware of pain" and indicates a persistent property instead of simple P300 activity.

Intermediate event related potential such as P300 is considered to have a peak potential at about 300 to 400 msec, which varies depending on the details of processed information or load. Generally, non-persistence is exhibited, where a shift to the positive direction starts before 300 msec and reaches a peak at 300 to 400 msec. Meanwhile, as demonstrated in the present invention, persistence can continue unexpectedly without returning to the baseline even after 2000 msec from application of stimulation. This never returned and continued, for example, for 2 seconds in this case is an unexpected event. This was not expected to be usable for differentiation of pain. Persistent positive components being one of the important points is also an unexpected characteristic.

As used herein, "target stimulation" refers to stimulation targeted for measurement (e.g., stimulation that is the origin of pain). In actual diagnosis, target stimulation can be externally or internally generated pain stimulation that occurs irregularly, and external pain stimulation that is artificially applied as a reference for testing purposes.

As used herein, "reference stimulation" refers to stimulation that is a baseline of comparison for measurement of pain or the like. Reference stimulation is, for example, stimulation that does not result in pain while having the same type of physical property as pain stimulation. A biological response signal associated with pain can be identified based on the minimum difference in physical property by using such a biological response as a baseline. For example, 39° C. thermal stimulation used in the Examples herein is used as reference stimulation to find a property of thermal stimulation (e.g., 52° C. high temperature stimulation) resulting in pain. However, reference stimulation is not limited to thermal stimulation. Examples thereof include, but are not limited to, electrical stimulation.

As used herein, "intermediate time frame" refers to the time frame from point where an early event related potential occurs to the point where late event related potential (P600, late positive component, or the like) occurs. This is a time frame that includes values in the range between about 250 msec to 600 msec, a time frame from 250 msec, where the early time frame during which evoked potential (N100 or P100) is observed, to the time frame where cognitive processing components such as P300 or N400 appear, and can include the time frame up to where late positive component or P600 appears (vicinity of 600 msec). Examples of intermediate time frames can include 300 msec, 400 msec, 500 msec, 600 msec, and continuous time frames therebetween (including, for example, 315 msec, 350 msec, and the like).

As used herein, "persistent property" or "persistent ERP" refers to a state without peaks and valleys, or a state where a signal gently continues with a delay in the appearance of a peak for a long period of time. Typically, this refers to a continuation of signals without reaching a peak continuously for at least 100 msec. As repeatedly described below, a persistent component can be identified by the following plurality of technical methods. 1) If there is a deviation from the activity of reference stimulation (brainwave waveform) after application of stimulation from immediately after application of stimulation, the component is not related to pain perception or cognition, but is possible an artifact. 2) If the standard line of a brainwave is shifted significantly upward to downward in view of brainwave waveforms from each application of stimulation, and is eliminated when the standard line is returned to a baseline by linear correction, this is not referred to as a persistent component. 3) If a low frequency band component such as 0.02 Hz, 0.01 Hz, or 0.1 Hz is blocked, a persistent component is eliminated in accordance with the persistent period. Thus, if not falling under 1 or 2 and such a low frequency component is blocked and eliminated, the component can be identified as persistent ERP. 4) If as of offline analysis, a significant correlation is found between features including the amplitude, frequency power, and the like of a persistent component and the behavioral property or psychological property in a test of objects or stimulation property such as pain intensity, the persistent component can be judged to be a signal associated with stimulation.

Figure 19:
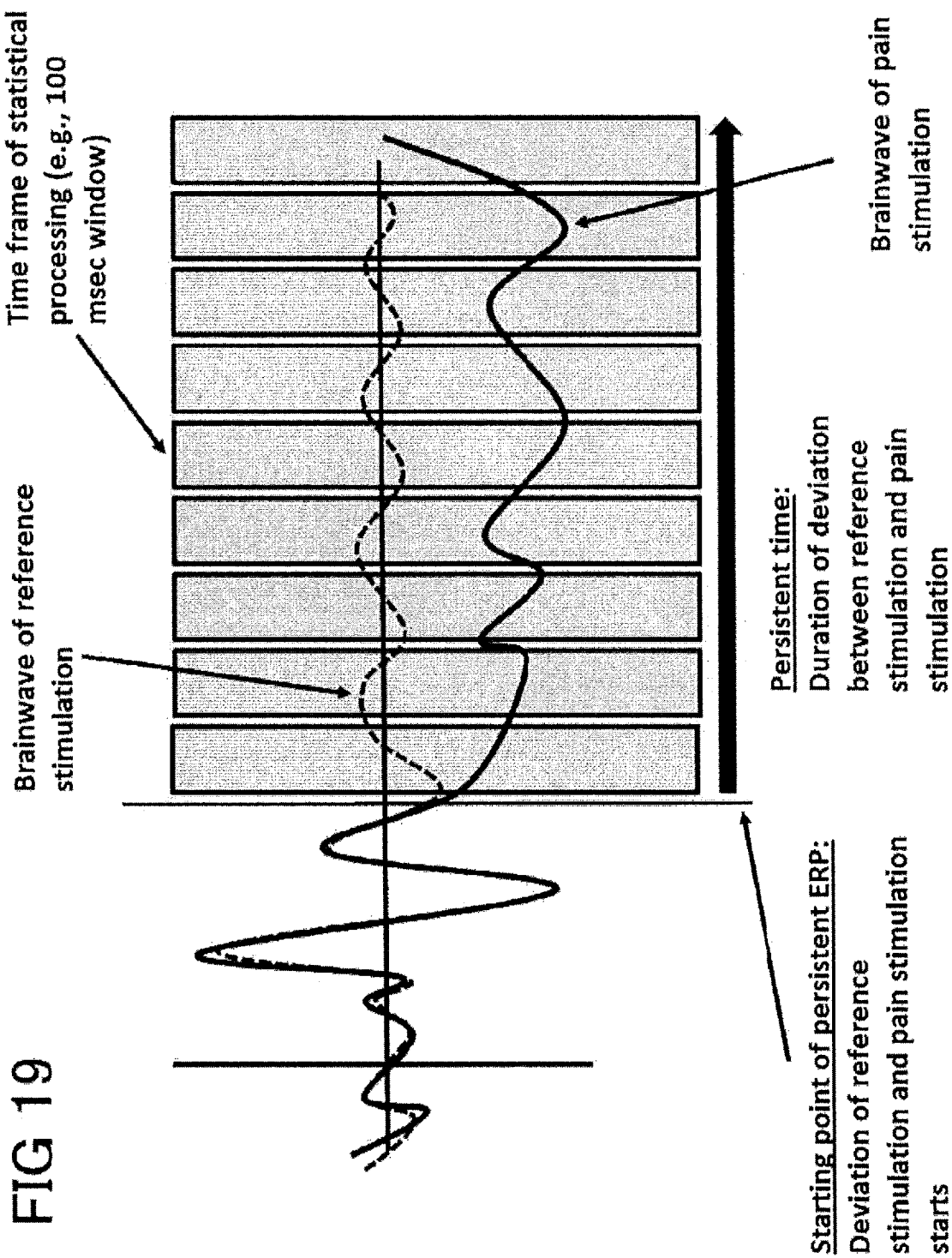
FIG. 19 shows a method of identifying a persistent ERP and a statistical validation method, which have been revealed to be effective for differentiation of instantaneous pain in the present invention. The point where pain stimulation has a persistent divergence from reference stimulation and the persistent period are identified. This segment is divided into, for example, 100 msecs and examined using a comparative method of representative values such as t-test or ANOVA.

Typically, components having a peak in activity like a mountain (e.g., appearing clearly in a range of about 0.2 seconds (200 msec)) are not included in persistent components. In other words, if "an effect is manifested as a steep slope and does not disappear, without a peak or the peak is difficult to identify", a component can be determined as persistent. "Mountain (having a clear peak)" and "persistent" have a clear difference and can be determined, as is apparent in view of the example in FIG. 18 or the like. If, after application of stimulation, an effect appears from at least about 400 msec and a clear peak like a mountain does not appear or appears very slowly, this is empirically referred to as persistent. When shifting and deviating from brain activity under a standard condition and exceeding at least 100 msec and continuing for preferably 200 msec or greater, preferably 300 msec or greater, preferably 500 msec or greater, and still more preferably 1000 msec or greater, this is referred to as a persistent state. If a positive effect is observed for a certain time or longer or at all times in a time segment of the target range of measurement, this can be considered a persistent state. For example, if this segment is divided into about 100 msec segments and a difference in conditions is found in all or majority of segments, this can be interpreted as persistent. For example, if a statistically significant difference is observed with an at least 100 msec range, it can be determined that persistence is observed herein. A persistent component is also sensitive to filtering of frequencies. For example, CNV (contingent negative variation), which is persistent negative ERP reflecting a prediction, continues for 3 seconds or longer, and a low frequency band of 0.02 Hz or greater is generally included in analysis. In other words, when this component is objectively judged, it can be judged by whether the component disappears when the low frequency band to be blocked is raised. Alternatively, as shown in FIG. 19, a method of identifying persistent ERP and statistical investigation can be performed by identifying the point at which pain stimulation has a persistent divergence from reference stimulation and the persistent period thereof, and dividing the segment by for example 100 msec and testing the segments using a method of comparing representative values such as a t-test or ANOVA.

In one embodiment for persistent properties, comparing can measure whether there is a persistent period where a value of brainwave data or analysis data thereof obtained from the target stimulation is different from a value of brainwave data or analysis data thereof obtained from the reference stimulation and, if there is the different persistent period, whether the values would be the same value again after becoming different; and if there is the persistent period and the values would not be the same value again, determining that there is unpleasant pain. Examples of persistent period include, but are not limited to, excess of 100 msec and continuation for preferably 200 msec or greater, preferably 300 msec or greater, preferably 500 msec or greater, and still more preferably 1000 msec or greater. Reference stimulation is stimulation resulting in a known response in an object. Examples include stimulation that can be a standard such as 1000 Hz for audio stimulation, simple stimulation such as figures for visual stimulation, stimulation with weak intensity for electrical stimulation, and stimulation with a physical or psychological property that does not result in unpleasantness or discomfort.

To determine a persistent property for event related potential, the corresponding effect of brain activity to pain is identified based on brain activity of reference stimulation. Thus, if pain already exists and is persistent, further analysis of this feature can be required instead of differentiating only with the feature. Meanwhile, individual differences in sensitivity to pain can be found with this indicator of the invention. For example, before monitoring pain, two types of instantaneous pain stimulation, i.e., "non-painful reference stimulation" and "painful stimulation", are randomly applied about 10 times each, and persistent effects of pain stimulation (converted to a z-value) are inputted into a sigmoid differentiation instrument or the like, which enables identification of which category the pain falls under. It is envisioned that this information can be used for correcting weighting coefficients of a differentiation algorithm used for pain monitoring based on the sensitivity. In a preferred embodiment, a targeted feature is preferably potential, persistent period, or a combination thereof. If pain evaluation of individuals exhibits a significant correlation with this feature, it can be shown that there is an individual difference. In the graph of sigmoid function approximation in the Examples, about 30% of the samples result in error in differentiation of strong pain. Thus, the difference between the error group and correct answer group can be considered as an individual difference.

While it is known that intermediate event related potential such as P300 reaches peak potential at about 300 to 400 msec, this is understood to vary depending on details of processed information or load. Thus, a shift to a positive direction generally exhibits non-persistence, starting before 300 msec and reaching a peak at 300 to 400 msec. Meanwhile, persistence unexpectedly continues without returning to the baseline even after 2000 msec from application of stimulation in some cases, as shown in the Examples (see FIG. 18). It was not previous known that finding such an event can result in finding pain such as instantaneous pain, which is a surprising effect. In a preferred embodiment of the invention, it is desirable to focus on the difference in "polarity" of not being a persistent negative component, but a positive component.

Alternatively, the following is checked to determine whether there is a persistent property. 1) If there is a deviation from the activity of reference stimulation (brainwave waveform) after application of stimulation from immediately after application of stimulation, the component is not related to pain perception or cognition, but is possible an artifact. 2) If the standard line of a brainwave is shifted significantly upward to downward in view of brainwave waveforms from each application of stimulation, and is eliminated when the standard line is returned to a baseline by linear correction, this is not referred to as a persistent component. 3) If a low frequency band component such as 0.02 Hz, 0.01 Hz, or 0.1 Hz is blocked, a persistent component is eliminated in accordance with the persistent period. Thus, if not falling under 1 or 2, and such a low frequency component is blocked and eliminated, the component can be identified as persistent ERP. 4) If as of offline analysis, a significant correlation is found between features including the amplitude, frequency power, and the like of a persistent component and the behavioral property or psychological property in a test of objects or stimulation property such as pain intensity, the persistent component can be judged to be a signal associated with stimulation.

As used herein, "sparse" or "sparse modeling" is a type of scientific mathematical modeling, referring to a methodology of deriving the overall picture from little information. Sparse means scattered or scant. The basic idea is that this is a methodology, which (1) while assuming that there is less (more sparse) explanatory variables of the higher order data than the number of orders, (2) performs regularization, i.e., simultaneously requesting smooth model fitting to data with minimization of the number of explanatory variables by providing a penalty term (e.g., introduction of a λ coefficient in L1 regularization), (3) to enable automatic selection of explanatory variables that does not depend on manual operation.

As used herein, "fitting" to a function refers to a technique of fitting measured values or a curve obtained therefrom to approximate a function of interest, which can be performed based on any approach. Examples of such fitting include least square fitting, nonlinear regression fitting (MATLAB nlinfit function or the like), and the like. A regression coefficient can be calculated for the approximated curve to determine whether the curve can be used or preferable in the present invention. For a regression coefficient, a regression equation model is effective. The adjusted coefficient of determination ($R^2$) is desirable with a numerical value closer to "1" such as 0.5 or greater, 0.6 or greater, 0.7 or greater, 0.8 or greater, 0.85 or greater, 0.9 or greater, or the like. A higher numerical value has higher confidence. The accuracy of fitting can be studied by using a specific threshold value to categorize and compare an estimated value and an actual measurement value (this is referred to as differentiation accuracy in the analysis of the invention).

As used herein, "cross validation" refers to a statistical methodology of dividing sample data, initially analyzing a portion thereof and performing a test on the analysis thereof with the remaining portion, which is applied to validation/verification of the suitability of the analysis itself. Cross validation is referred to as 10-fold cross validation when divided into 10 and 5-fold cross validation when divided into 5. This is a methodology for validating/verifying with excellent approximation how much the analysis of data (and derived estimation/statistical prediction) can actually match the population. The data analyzed first is referred to as "learning data", "training set", or the like, and other data is referred to as the "testing set", "test data", or the like. Division into 10 in 10-fold cross validation exemplified herein is one example. Leave-one-out cross validation can also be used. They are also collectively referred to as "split cross validation". For sparse modeling, a suitable λ (preferably the optimal λ) value used in a penalty term by cross validation is identified, and a parameter of a feature (partial regression coefficient) and a constant (intercept) of an algorithm are determined. In this regard, the "λ value" is a hyperparameter functioning in regularization, used for improving the smoothness of compatibility of the model and generalization capability. While regularization is categorized into L1 regularization and L2 regularization, LASSO (Least absolute shrinkage and selection operator) used in one of the preferred embodiments in the present invention uses L1 regularization. A λ coefficient is a positive coefficient, and a suitable (preferably optimal) solution is determined by cross validation. As a specific example, the LASSO function in MATLAB solves the following minimization problem.

$$\text{Min}(\text{Dev}(\beta_0,\beta)+\lambda\Sigma|\beta_j|)$$ [Numeral 1]

Min: minimization

Dev: degree of deviation (discrepancy of a regression model estimation value using intercept $\beta_0$ and regression coefficient $\beta$ from an observed value)

N: number of samples

λ: regularization parameter with a positive value wherein a partial regression coefficient refers to a coefficient of each explanatory variable in a regression equation obtained by regression analysis, and the intercept refers to an intersection of graph such a curve on a coordinate plane and a coordinate axis.

Sparse modeling is explained by Ozeki et al (2015 Osaka City University Denshi Butsuri Kogaku Tokubetsu Kogi [Physics and Electrical Engineering Special Lecture] (revised edition: Sep. 9, 2015)). The sparse model analysis and LASSO explained therein can be applied herein. The entire document is incorporated herein by reference.

Compressed sensing can be used to determine whether a resulting solution is a sparse solution in norm selection used in sparse model analysis. In this regard, noise containing pressure sensing can be used when noise is observed. Noise-containing pressure sensing can use a methodology referred to as LASSO (Least Absolute Shrinkage and Selection Operators; R. Tibshirani: J. R. Statist. Soc. B, 581a (1996)26).

In sparse model analysis, data input, algorithm determination of a differentiation/estimation unit, and output of differentiation/estimation can be performed a plurality of times (e.g., 1000 times or less or more) to arrive at a suitable value (preferably optimized) such as 2000, 3000, 5000, or 10000 times.

A parameter (coefficient) of a feature and constant (intercept) of an algorithm are determined using a suitable (preferably optimal) λ coefficient, which is repeated 1000 times when differentiating and estimating a test data. The mean thereof is the differentiation accuracy. The stringency is vastly different from accuracy differentiation of conventional art. When using a regression model generated for general use, it is preferable to perform calibration for each individual. A technology for correcting the parameter (coefficient) of a feature and constant (intercept) of an algorithm used in this model can be added.

The following point should be noted when performing sparse model analysis upon modeling in the present invention. For example, features used need to be used in the same unit because each coefficient is similarly multiplied by the λ value for regularization in LASSO. Therefore, features need to be kept consist by normalization.

As used herein, "classification" of pain can be performed from various viewpoints. Representative examples include, but are not limited to, classification by whether pain is "painful" or "not painful" for the object being estimated, as well as whether pain is felt, and quantitative distinction between strong pain and weak pain, and also qualitative distinction ("bearable" pain or "unbearable" pain).

Preferred Embodiments

The preferred embodiments of the present invention are described hereinafter. It is understood that the embodiments provided hereinafter are provided to facilitate better understanding of the present invention, so that the scope of the invention should not be limited by the following descriptions. Thus, it is apparent that those skilled in the art can refer to the descriptions herein to make appropriate modifications within the scope of the invention. It is also understood that the following embodiments of the invention can be used individually or as a combination.

Each of the embodiments described below provides a comprehensive or specific example. The numerical values, shapes, materials, constituent elements, positions of arrangement and connection forms of the constituent elements, steps, order of steps, and the like in the following embodiments are one example, which is not intended to limit the Claims. Further, the constituent elements in the following embodiments that are not recited in the independent claims showing the most superordinate concept are described as an optional constituent element.

In this regard, the inventors elucidated the relationship between pain and brainwaves by evaluating a plurality of types of pain by a plurality of methods. The relationship between pain and brainwaves elucidated by the inventors is described hereinafter with reference to the drawings.

First, the relationship between pain due to electrical stimulation and brainwaves is described. The data provided hereinafter shows data for one representative subject from a plurality of subjects.

Figure 1B:
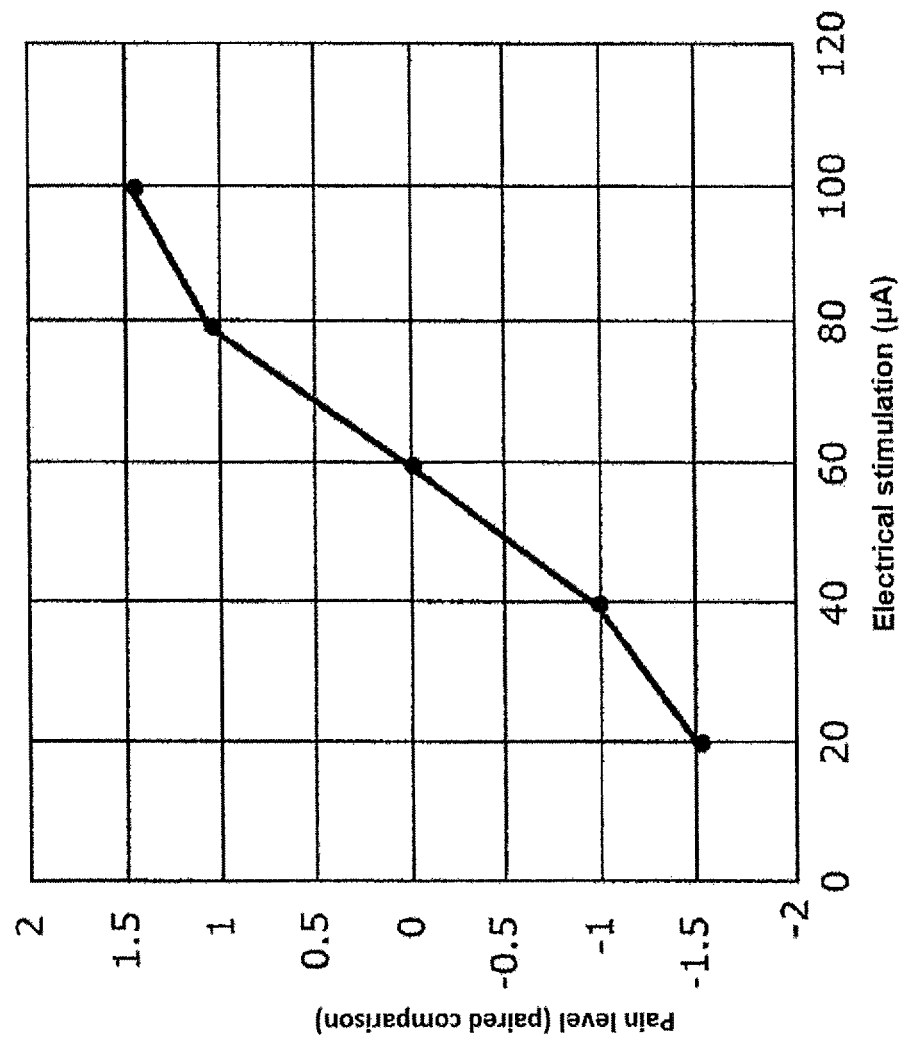
FIG. 1B is a graph showing the relationship between electrical stimulation and pain levels (paired comparison).
Figure 1C:
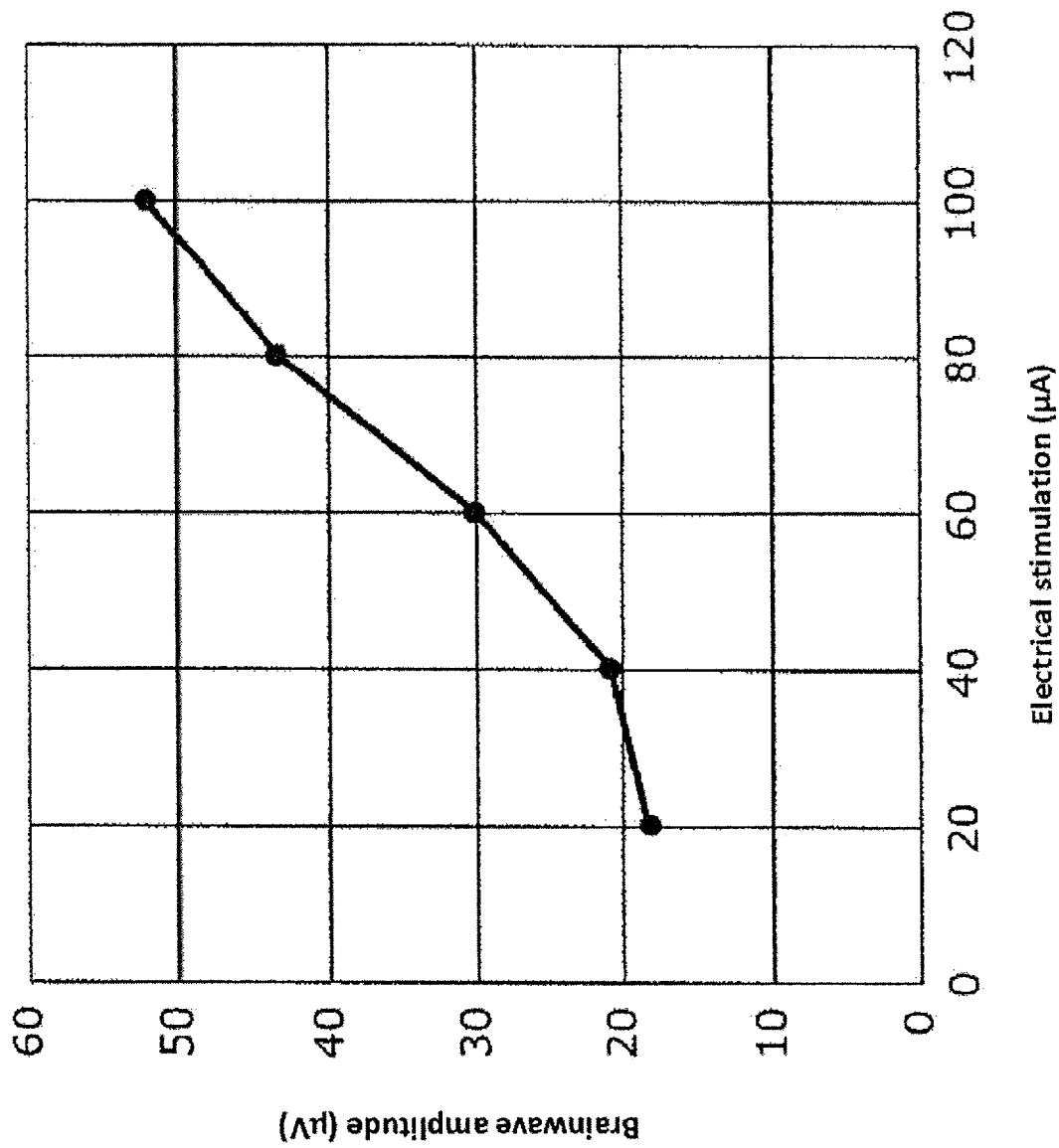
FIG. 1C is a graph showing the relationship between electrical stimulation and brainwave amplitude.
Figure 1D:
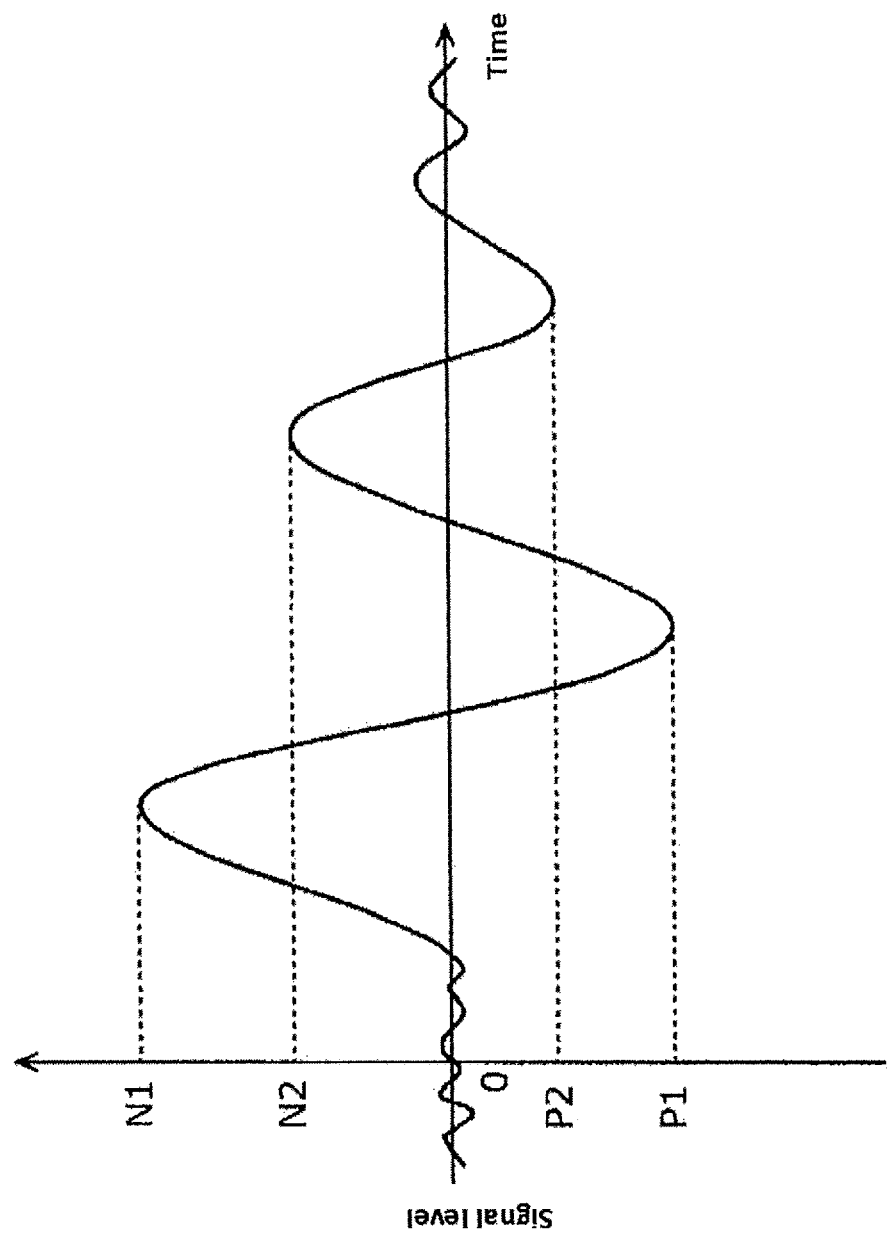
FIG. 1D is a graph showing an example of a waveform of a brainwave.

FIG. 1A is a graph showing the relationship between electrical stimulation and pain levels (VAS). FIG. 1B is a graph showing the relationship between electrical stimulation and pain level (paired comparison). FIG. 1C is a graph showing the relationship between electrical stimulation and brainwave amplitude. FIG. 1D is a graph showing an example of a waveform of a brainwave.

The horizontal axes of FIGS. 1A, 1B, and 1C indicate the value of current of electrical stimulation. The vertical axis of FIG. 1A indicates the pain level reported by the subject in accordance with VAS. The vertical axis of FIG. 1B indicates the pain level reported by the subject in accordance with paired comparison. The vertical axis of FIG. 1C indicates the value of brainwave amplitude. In FIG. 1D, the horizontal axis indicates time, and the vertical axis indicates signal levels.

Paired comparison is a method of using two magnitudes of electrical stimulation as a set and having a subject report which electrical stimulation is how much more painful by a numerical value for each of a plurality of sets of electrical stimulation. In such a case, pain levels are reported by comparing two pains, so that the effect of past experience of a subject with respect to pain levels can be mitigated.

As shown in FIGS. 1A and 1B, the relationship between the value of current of electrical stimulation (i.e., intensity of stimulation) and pain level is represented roughly by a sigmoid (S-shaped) curve, regardless of which of VAS or paired comparison method is used. The shape of the sigmoid curve (e.g., the upper limit value and lower limit value, and the like) varies depending on the subject.

As shown in FIG. 1C, the relationship between the value of current of electrical stimulation and the value of brainwave amplitude is also roughly represented by a sigmoid curve. In this regard, the difference between the maximum peak value and minimum peak value (i.e., peak-to-peak value) is used as the value of brainwave amplitude. For example, in FIG. 1D, the maximum value of difference (N1-P1) among three differences (N1-P1, N2-P2, and N1-P2) is used as the value of amplitude.

In this manner, the relationship between the intensity of electrical stimulation and pain level and the relationship between the intensity of electrical stimulation and the value of brainwave amplitude are both expressed by a sigmoid curve. In other words, pain levels and brainwave amplitude both have an upper limit and lower limit to electrical stimulation and exhibit a similar change with respect to the intensity of electrical stimulation. In this regard, the relationship between the value of brainwave amplitude and pain level, when analyzed, was represented as shown in FIGS. 1E and 1F.

Figure 1E:
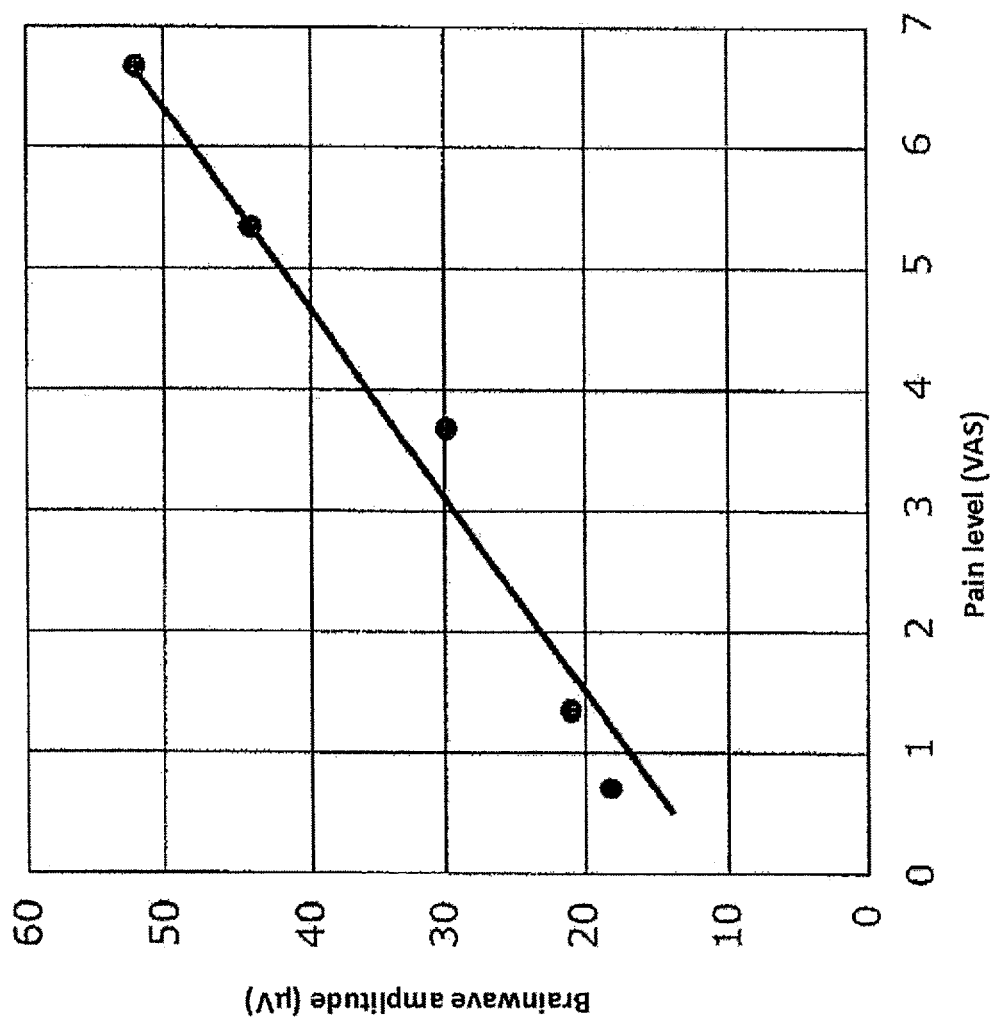
FIG. 1E is a graph showing the relationship between pain level due to electrical stimulation (VAS) and brainwave amplitude.

FIG. 1E is a graph showing the relationship between pain level due to electrical stimulation (VAS) and brainwave amplitude. FIG. 1F is a graph showing the relationship between pain level due to electrical stimulation (paired comparison) and brainwave amplitude. In FIGS. 1E and 1F, the horizontal axis indicates the brainwave amplitude, and the vertical axis indicates the pain level.

Figure 1F:
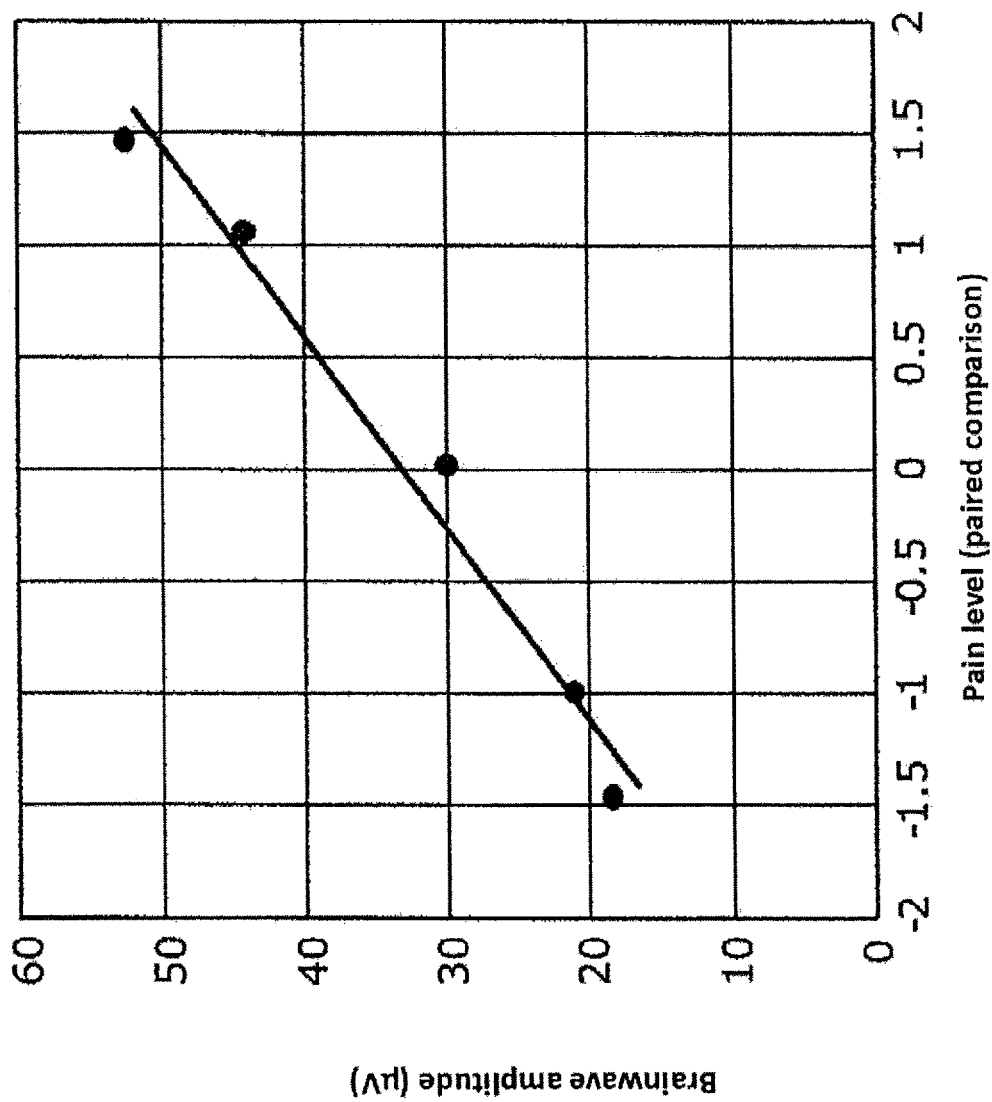
FIG. 1F is a graph showing the relationship between pain level due to electrical stimulation (paired comparison) and brainwave amplitude.

As shown in FIGS. 1E and 1F, the pain level due to electrical stimulation and the value of brainwave amplitude have linearity for both VAS and paired comparison. In other words, the value of brainwave amplitude is proportional to the pain level.

As used herein, linearity includes strict linearity as well as substantial linearity. In other words, linearity includes relationships that can be approximated to linearity within a given range of error. A given range of error is defined, for example, by a coefficient of determination $R^2$ in regression analysis. The coefficient of determination $R^2$ is a value found by subtracting 1 from a result of dividing the Residual Sum of Squares by Total Sum of Squares of the difference in the observed value from the mean value. The give range of error is, for example, a range where $R^2$ is 0.5 or greater.

For the relationship between pain due to thermal stimulation and brainwaves, the pain level and brainwave amplitude also have linearity in the same manner as electrical stimulation.

Figure 1G:
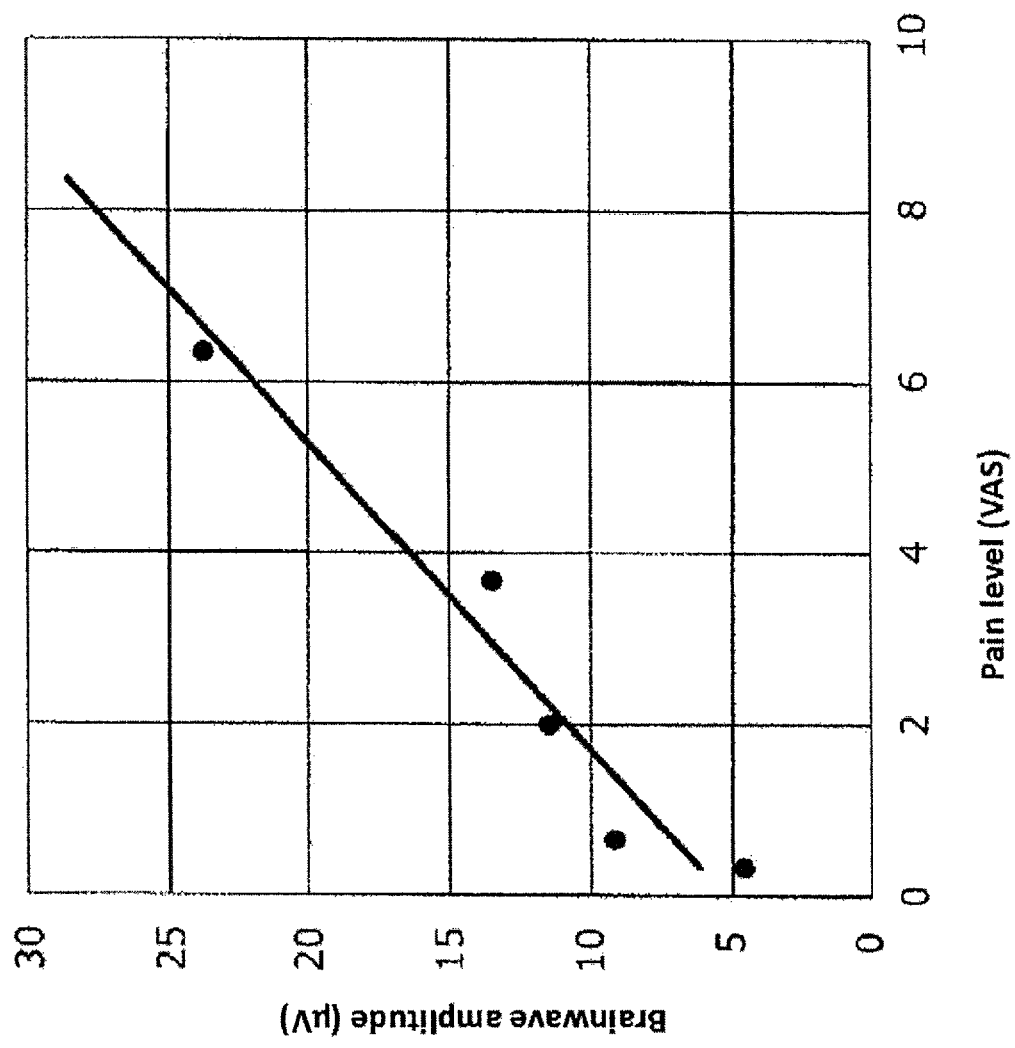
FIG. 1G is a graph showing the relationship between pain level due to thermal stimulation (VAS) and brainwave amplitude.
Figure 2:
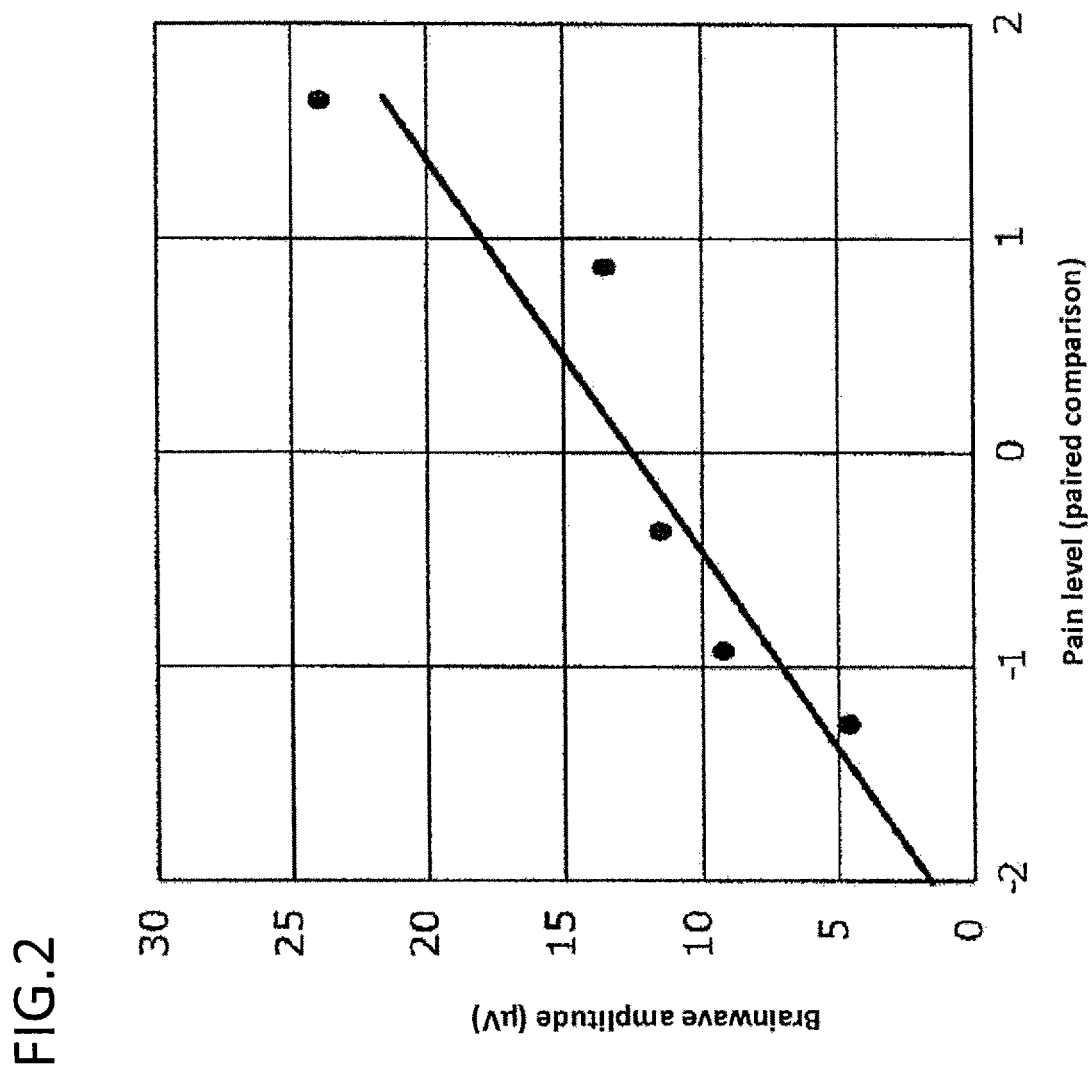
FIG. 2 is a graph showing the relationship between pain level due to thermal stimulation (paired comparison) and brainwave amplitude.
Figure 3:
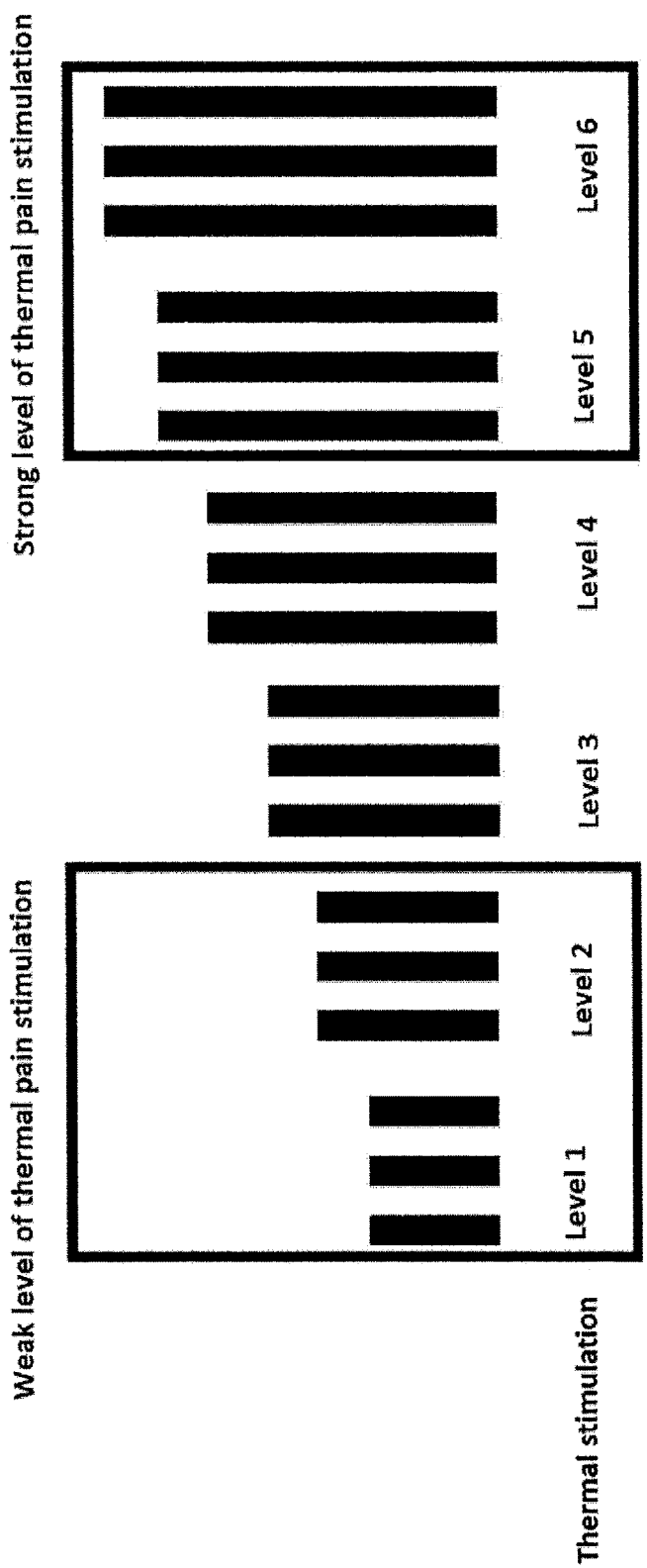
FIG. 3 shows a thermal stimulation experiment paradigm of Example 1. Thermal stimulation was increased by 2° C. from level 1 at 40° C. to level 6 at 50° C., with the baseline temperature of 35° C. Each temperature level included three stimulations, and each stimulation lasted 15 seconds.

FIG. 1G is a graph showing the relationship between the pain level due to thermal stimulation (VAS) and brainwave amplitude. FIG. 2 is a graph showing the relationship between the pain level due to thermal stimulation (paired comparison) and brainwave amplitude. In FIGS. 1G and 2, the horizontal axis indicates the brainwave amplitude, and the vertical axis indicates the pain level.

As shown in FIGS. 1G and 2, the pain level due to thermal stimulation and the value of brainwave amplitude have linearity for both VAS and paired comparison. While the upper limit value and lower limit value of the value of brainwave amplitude have variations depending on the subject, the inventors found through experiments that the upper limit value of amplitude does not exceed about 60 μV.

In this manner, the inventors have elucidated that brainwave amplitudes and pain have a specific relationship as a result of analyzing the relationship between values of brainwave amplitude and pain levels from evaluation of a plurality of types of pain by a plurality of methods. In addition, the present invention found that sparse modeling for estimating the magnitude of pain based on the specific relationship between brainwave amplitudes and pain can be utilized.

<Pain Differentiation/Classification>

In one aspect, the present invention provides a method of differentiating or classifying pain of an object being estimated based on a brainwave of the object being estimated. This method comprises: a) obtaining brainwave data for a model or analysis data thereof corresponding to stimulation intensity for a model; b) extracting a brainwave feature for a model from the brainwave data or analysis data thereof; c)

setting a pain level of interest, introducing the brainwave feature for a model and the pain level into sparse model analysis, finding a suitable A (preferably the optimal λ) (methodology of reducing error by the least square method, preferably a methodology that minimizes the error), and determining a parameter (partial regression coefficient) for the brainwave feature for a model and a constant (intercept) of an algorithm corresponding to the suitable A (preferably the optimal λ) to generate a regression model; d) obtaining brainwave data (for measurement) or analysis data thereof of the object being estimated; e) extracting a brainwave feature for measurement from the brainwave data for measurement or analysis data thereof; f) calculating a corresponding pain level by fitting the brainwave feature for measurement to a regression model; and g) optionally displaying the pain level. a) to c) are stages for generating a regression model. d) to f) are stages for calculating a pain level by fitting brainwave data or analysis data thereof from a subject (object) based on the generated regression model. Pain can be differentiated with good accuracy through such procedures. When using the technology of the invention as medical equipment, the calculated pain level is preferably displayed in a manner that is readily understood by users as needed. The numerical value of error that is tolerable as the suitable λ value can be appropriately determined by those skilled in the art in accordance with each case. For example, the value can be determined to be within the range of a specific λ value (e.g., 0.0001 to 0.01, or 0.00001, 0.0001, 0.001, 0.01, or the like, or range between any of these values) by cross validation. The optimal λ is a value calculated or can be determined so that the error would be the minimum value by the least square method, and can be readily determined by those skilled in the art using any known methodology.

In one aspect, the present invention provides an apparatus for differentiating or classifying pain of an object being estimated based on a brainwave of the object being estimated. The apparatus comprises: a) a model data obtaining unit for obtaining brainwave data for a model or analysis data thereof corresponding to stimulation intensity for a model; b) a model feature extraction unit for extracting a brainwave feature for a model from the brainwave data or analysis data thereof; c) a regression model generation unit for setting a pain level of interest, introducing the brainwave feature for a model and the pain level into sparse model analysis, finding a suitable A (preferably the optimal λ), and determining a parameter (partial regression coefficient) for the brainwave feature for a model and a constant (intercept) of an algorithm corresponding to the suitable A (preferably the optimal λ) to generate a regression model; d) a measurement data obtaining unit for obtaining brainwave data (for measurement) or analysis data thereof of the object being estimated; e) a measurement feature extraction unit for extracting a brainwave feature for measurement from the brainwave data for measurement or analysis data thereof; f) a pain level calculation unit for calculating a corresponding pain level by fitting the brainwave feature for measurement to a regression model; and g) optionally a pain level display unit for displaying the pain level.

In another aspect, the present invention provides a program for making a computer execute a method of differentiating or classifying pain of an object being estimated based on a brainwave of the object being estimated. The method executed by the program comprises: a) obtaining brainwave data for a model or analysis data thereof corresponding to stimulation intensity for a model; b) extracting a brainwave feature for a model from the brainwave data or analysis data thereof; c) setting a pain level of interest, introducing the brainwave feature for a model and the pain level into sparse model analysis, finding a suitable λ (preferably the optimal λ), and determining a parameter (partial regression coefficient) for the brainwave feature for a model and a constant (intercept) of an algorithm corresponding to the suitable λ (preferably the optimal λ) to generate a regression model; d) obtaining brainwave data (for measurement) or analysis data thereof of the object being estimated; e) extracting a brainwave feature for measurement from the brainwave data for measurement or analysis data thereof; f) calculating a corresponding pain level by fitting the brainwave feature for measurement to a regression model; and g) optionally displaying the pain level. Alternatively, the present invention provides a recording medium storing the program described above. Typically, A) a model data obtaining unit performs step a), B) a model feature extraction unit performs step b), C) a regression model generation unit performs step c), D) a measurement data obtaining unit (can be the same as the brainwave data obtaining unit) performs step d), a measurement brainwave feature extraction unit (can be the same as the model brainwave feature extraction unit) performs step e), a pain level calculation unit (can have the function of the regression model generation unit and is also referred to as a pain classifier generation unit) performs step f), and a pain level display unit performs step g).

In another aspect, the present invention provides a method of estimating pain of an object being estimated based on a brainwave of the object being estimated, comprising: a) providing at least one approximation amount of a quantitative or qualitative level of pain obtained by inputting a brainwave feature into sparse model analysis; b) obtaining brainwave data or analysis data thereof from the object being estimated; c) extracting a brainwave feature from the brainwave data or analysis data thereof; and d) differentiating or estimating a pain level of the object being estimated from the brainwave feature based on the approximation amount.

When differentiating pain of an object, it is preferable that data is not collected to make a regression model from scratch using such data when actually differentiating, but instead actual data of the object is inputted into a base regression model that is made from model data or clinical data in advance for differentiation/estimation. In such a case, it is preferable that reference stimulation with strong pain and weak pain is first applied a plurality of times (10 times×2 types or the like), which is estimated with a differentiation model, and a parameter (partial regression coefficient) of a feature and a constant (intercept) of an algorithm are corrected while checking the accuracy.

The data obtaining step is very important in model creation, so that it is preferable to obtain data that is useable for clinical groups from a large number of subjects with variation in age groups as much as possible.

In the present invention, pain of a subject can be "estimated" or "differentiated" by calculating a pain level with a regression model (perform fitting). In doing so, a pain classifier can be generated from the regression model. It is understood that knowing the pain level or weak/strong attains an effect of the ability to administer treatment without inflicting strong stimulation, and objectively knowing the therapeutic effect of an analgesic or the like.

As used herein, "pain classifier" refers to a value or range of brainwave data (e.g., amplitude) or analysis value thereof identified for classifying types of pain. In this disclosure, a unit, apparatus, or instrument for generating a "pain classifier" (and thus predicting pain) can also be referred to as a "pain classification instrument", "pain prediction instrument", or the like. In this disclosure, this can be determined by, for example, but not limited to, utilizing a point where a certain change is found or the like based on a regression model curve obtained by stimulating the object being estimated and plotting, and applying and fitting into a regression model, stimulation intensity or a subjective pain sensation level corresponding thereto from data such as amplitude data of brainwaves obtained therefrom. A pain classifier, once generated, can be improved by calibration. A pain classifier can be denoted as pain classifier, pain predictor, or the like, which are synonymous. It is possible to distinguish whether it is a "change within the strong level of pain" or "qualitative change indicating low level of pain, which is a deviation from the strong level of pain" by using a "pain classifier". If there is a reaction with a deviation beyond a change within the strong level of pain, this can be distinguished from a change within the strong level of pain using the pain classifier of the invention. If there is a change within the strong level of pain, a change that is not an error can be identified, and anything beyond this can be processed as a deviant reaction.

Figure 12:
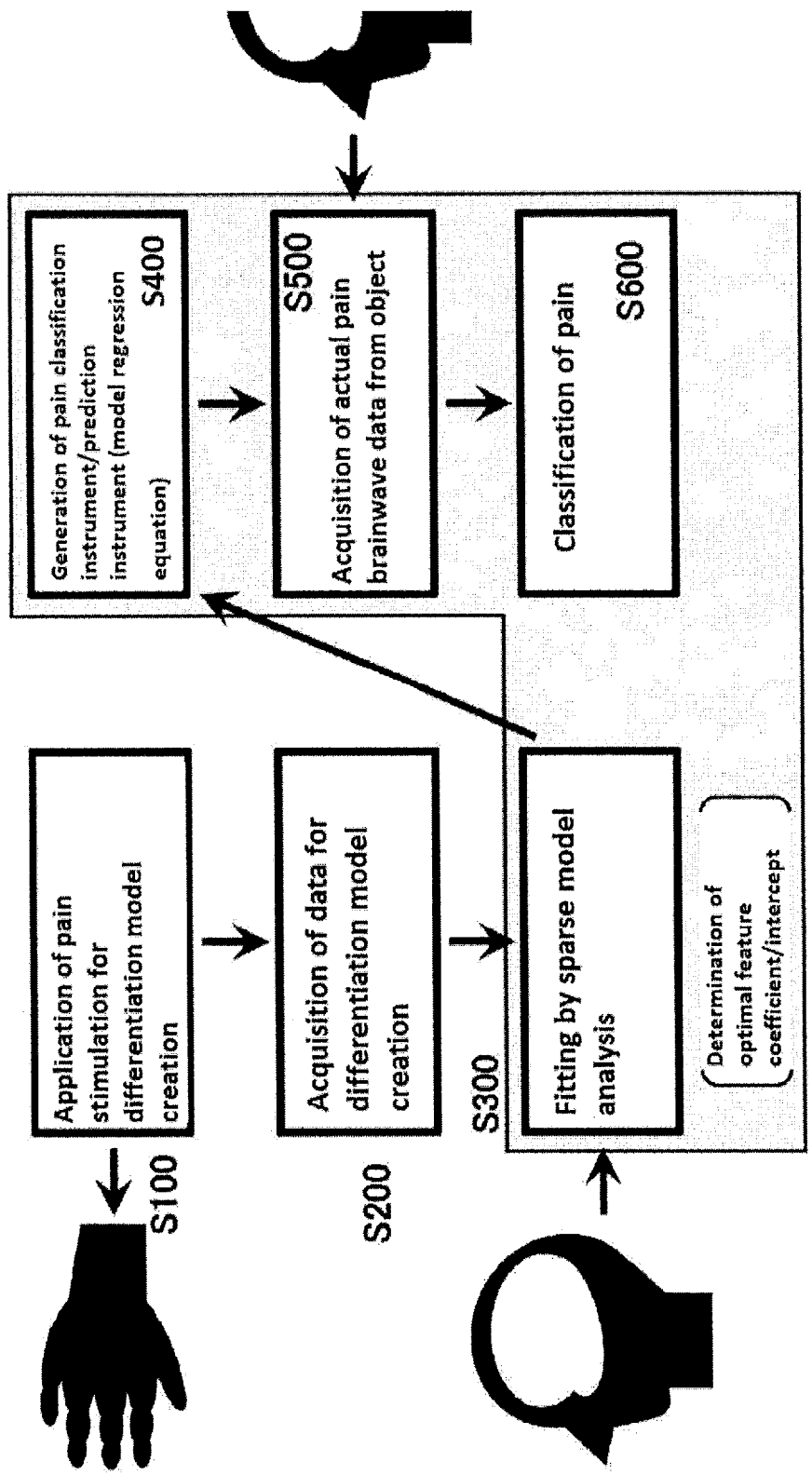
FIG. 12 is an example of a flowchart showing the flow of the invention.

The methodology of calculating a pain level is described using the following schematic diagram (FIG. 12).

In step a) which is the (obtain data for differentiation model creation) step (S200) for obtaining brainwave data for a model or analysis data thereof corresponding to stimulation intensity for a model (apply pain stimulation for differentiation model creation, S100), an object being estimated is stimulated with a plurality of levels (intensity or magnitude) of stimulation (e.g., cold temperature stimulation, electrical stimulation, or the like) to obtain a brainwave. The number of types of stimulation intensity can be a number required for creating a function pattern, e.g., generally at least three types that are weak/moderate/strong. Such number of types is not necessarily required because one or two types can be applied to sparse modeling in combination with information obtained in advance. Meanwhile, it can be advantageous to stimulate with generally at last three types, preferably four types, five types, six types, or more types of levels when newly applying. Three types are preferable because weak/moderate/strong can be found. A greater number is ideal because a function pattern can be found in more detail, but the number is not limited thereto. In this regard, burden to an object being estimated should be minimized, so that the number of stimulation intensities that are highly invasive to the object being estimated (in other words, intensity that is unbearable to the subject) is preferable kept at a minimum or zero. Meanwhile, stimulation that is highly invasive to an object being estimated can be necessary for more accurate fitting, so that a minimum number can be included depending on the objective. For example, the number of types of such highly invasive stimulation can be at least one type, at least two types, or at least three types, or, if tolerable by the object being estimated, 4 types or more. Brainwave data or analysis data thereof is also referred to as brain activity data, amount of brain activity, or the like. Examples thereof include amplitude data ("EEG amplitude"), frequency amplitude, and the like. Such brainwave data can be obtained using any methodology that is well known in the art. Brainwave data can be obtained by measuring electrical signals of a brainwave and is displayed by potential (can be displayed by μv or the like) as amplitude data or the like. Frequency properties are displayed as power spectrum density or the like.

In a preferred embodiment, brainwave data is preferably collected by a simple method, which can 1) use fewest possible number of electrodes (about two), 2) avoid the scalp with hair as much as possible, and 3) record while sleeping, to carry out the invention, but the number of electrodes can be increased as needed (e.g., can be 3, 4, 5, or the like).

Step b) is a step for extracting a brainwave feature for a model from the brainwave data or analysis data thereof. As the brainwave feature, a mean amplitude ((Fz, Cz, C3, C4), Fz: δ (1 to 3 Hz), θ (4 to 7 Hz), α (8 to 13 Hz), β (14 to 30 Hz), γ (30 to 100 Hz), Cz: 5 bands <δ (1 to 3 Hz), θ (4 to 7 Hz), α (8 to 13 Hz), β (14 to 30 Hz), γ (30 to 100 Hz)>, C3: 5 bands <δ (1 to 3 Hz), θ (4 to 7 Hz), α (8 to 13 Hz), β (14 to 30 Hz), γ (30 to 100 Hz)>, C4: 5 bands <δ (1 to 3 Hz), θ (4 to 7 Hz), α (8 to 13 Hz), β (14 to 30 Hz), γ (30 to 100 Hz)> or the like can be used. The frequency power or the like described above can also be used.

Step c) is a step (S300) for setting a pain level of interest, introducing the brainwave feature for a model and the pain level into sparse model analysis, finding a suitable λ value (preferably the optimal λ), and determining a parameter (partial regression coefficient) for the brainwave feature for a model and a constant (intercept) of an algorithm corresponding to the suitable λ (preferably the optimal λ) to generate a regression model. In this regard, a pain level is set, and a regression model (pain classification instrument/prediction instrument (model regression equation)) is created using the brainwave feature obtained in step b) (S400). Any methodology that is known in the art can be used for a regression model. Such a specific analysis methodology includes LASSO, which solves the following optimization problem for model fitting.

For sparse modeling, a suitable λ (preferably the optimal λ) value used in a penalty term by cross validation is identified, and a parameter (partial regression coefficient) of a feature and a constant (intercept) of an algorithm are determined. In this regard, the "λ value" is a hyperparameter functioning in regularization, used for improving the smoothness of compatibility of the model and generalization capability. While regularization is categorized into L1 regularization and L2 regularization, LASSO uses L1 regularization. A λ coefficient is a positive coefficient, and a suitable (preferably optimal) solution is determined by cross validation. As a specific example, the LASSO function in MATLAB solves the following equation by cross validation.

$$\text{Min}(\text{Dev}(\beta 0,\beta)+\lambda \Sigma|\beta j|)$$ [Numeral 2]

Min: minimization
Dev: degree of deviation (discrepancy of a regression model estimation value using intercept β0 and regression coefficient β from an observed value)
N: number of samples
λ: regularization parameter with a positive value Step (d) is a step for obtaining brainwave data (for measurement) or analysis data thereof of the object being estimated. Data for measurement is obtained by the same methodology as step c) (S500).

Step e) is a step for extracting a brainwave feature for measurement from the brainwave data for measurement or analysis data thereof. Step e) extracts a brainwave feature for measurement by the same methodology as step b). In this regard, the feature is extracted, as a premise, by processing of a brainwave signal (filter or the like) or secondary processing (signal processing).

Step f) is a step for calculating a corresponding pain level by fitting the brainwave feature for measurement to a regression model. In this regard, the brainwave feature for measurement can be inputted into the regression model to calculate a value for classifying or calculating a pain level corresponding to the value (S600).

Step g) is a step for optionally displaying the pain level. In this regard, the calculated pain level can be displayed by using a number or a graphic, or provided by audio. If the same subject is targeted, the step can comprise a step of succeeding or updating a classifier by using previous classifier data.

In the apparatus of the invention, A) a model data obtaining unit for obtaining brainwave data for a model or analysis data thereof corresponding to stimulation intensity for a model is configured to perform step a). In other words, the apparatus has means or a function that can provide a plurality of types of stimulation intensities and is configured to be able to apply such stimulation to an object. The apparatus is also configured to obtain brainwave data of an object being estimated. The brainwave data obtaining unit can perform step a) and have other functions (e.g., step d)).

B) a model feature extraction unit for extracting a brainwave feature for a model from the brainwave data or analysis data thereof is configured to obtain a model feature. The model feature extraction unit can perform step b) and have other functions (e.g., step e)).

C) a regression model generation unit for setting a pain level of interest, introducing the brainwave feature for a model and the pain level into sparse model analysis, finding a suitable λ value (preferably the optimal λ), and determining a parameter (partial regression coefficient) for the brainwave feature for a model and a constant (intercept) of an algorithm corresponding to the suitable λ (preferably the optimal λ) to generate a regression model can have function for generating a regression model. Generally, C) the regression model generation unit performs step c) and optionally step f). These two functions can be materialized by separate apparatuses, devices, CPUs, terminals, or the like, or materialized as a single unit. Generally, the unit is configured to incorporate, or configured to be capable of incorporating a program that materializes such calculation in a single CPU or computer.

Figure 4:
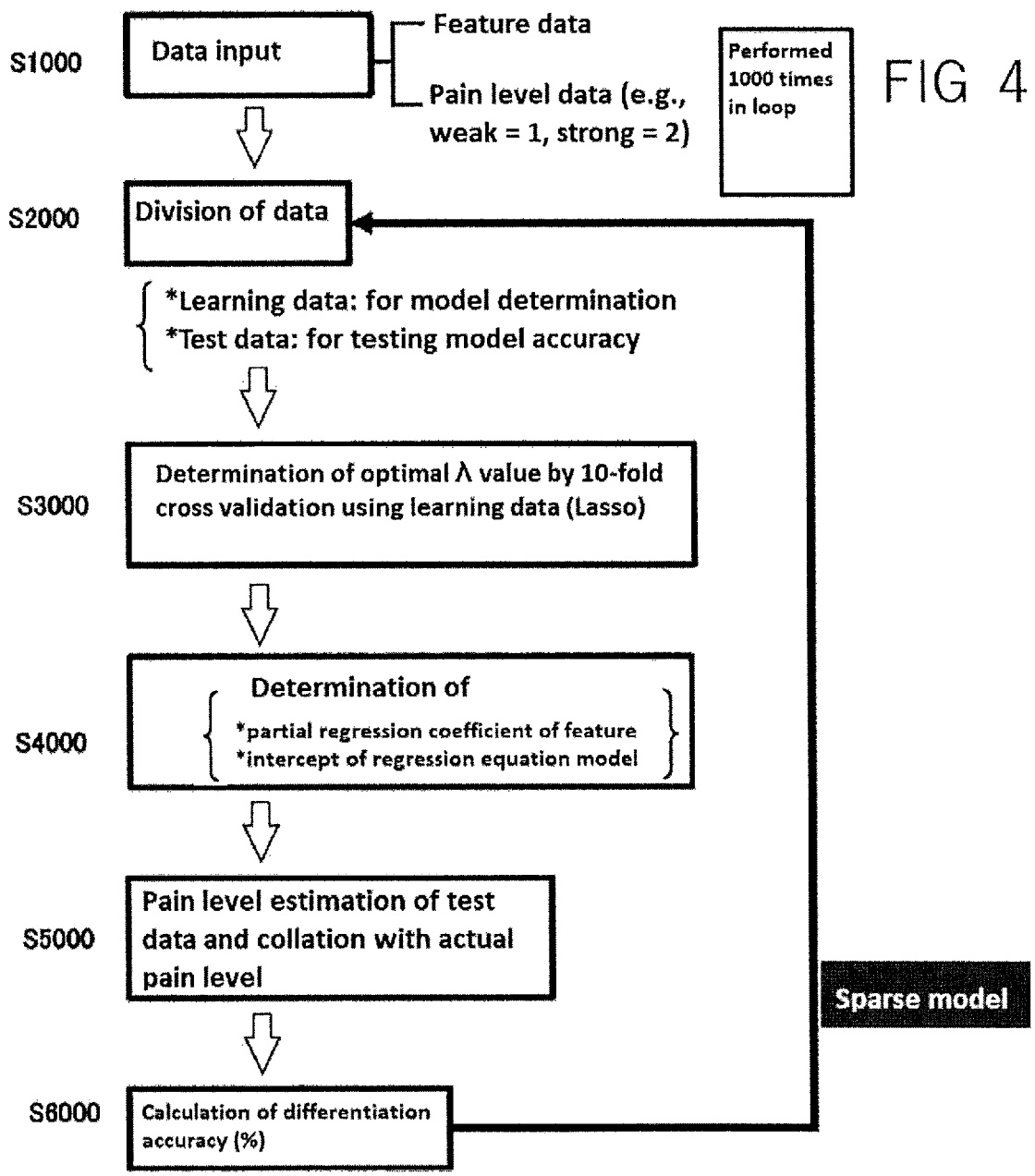
FIG. 4 is an example of a flowchart showing the flow of the invention, depicting the flow of sparse model analysis.

FIG. 4 is an example of FIG. 12 and is a more detailed procedure of sparse modeling exemplified in the Examples.

At S1000, data is inputted. Feature data and pain level data are inputted.

At S2000, data is divided, where the data is divided into learning data and test data. The learning data is used for determining a model, and the test data is used for testing model accuracy.

At S3000, a suitable (preferably optimal) λ value is determined by cross validation (the figure shows 10-fold cross validation) using the learning data (e.g., LASSO analysis).

At S4000, a parameter (partial regression coefficient) of a feature and a constant (intercept) of an algorithm are determined.

At S5000, the pain level of the test data is estimated, and collated with the actual pain level. An example of collation involves an existing regression model, where the estimation value thereof is strong pain ≥0.3 and weak pain <0.3, wherein the value is "2" when ≥0.3 and "1" when <0.3. In this regard, the actual pain levels are also expressed as "strong=2" and "weak=1". Thus, if they are collated and match, differentiation accuracy is calculated as correct.

At S6000, differentiation accuracy (%) is calculated. The procedure returns to S2000 from S6000 to repeatedly calculate accuracy a plurality of times (1000 times in FIG. 4) thereafter.

Figure 13:
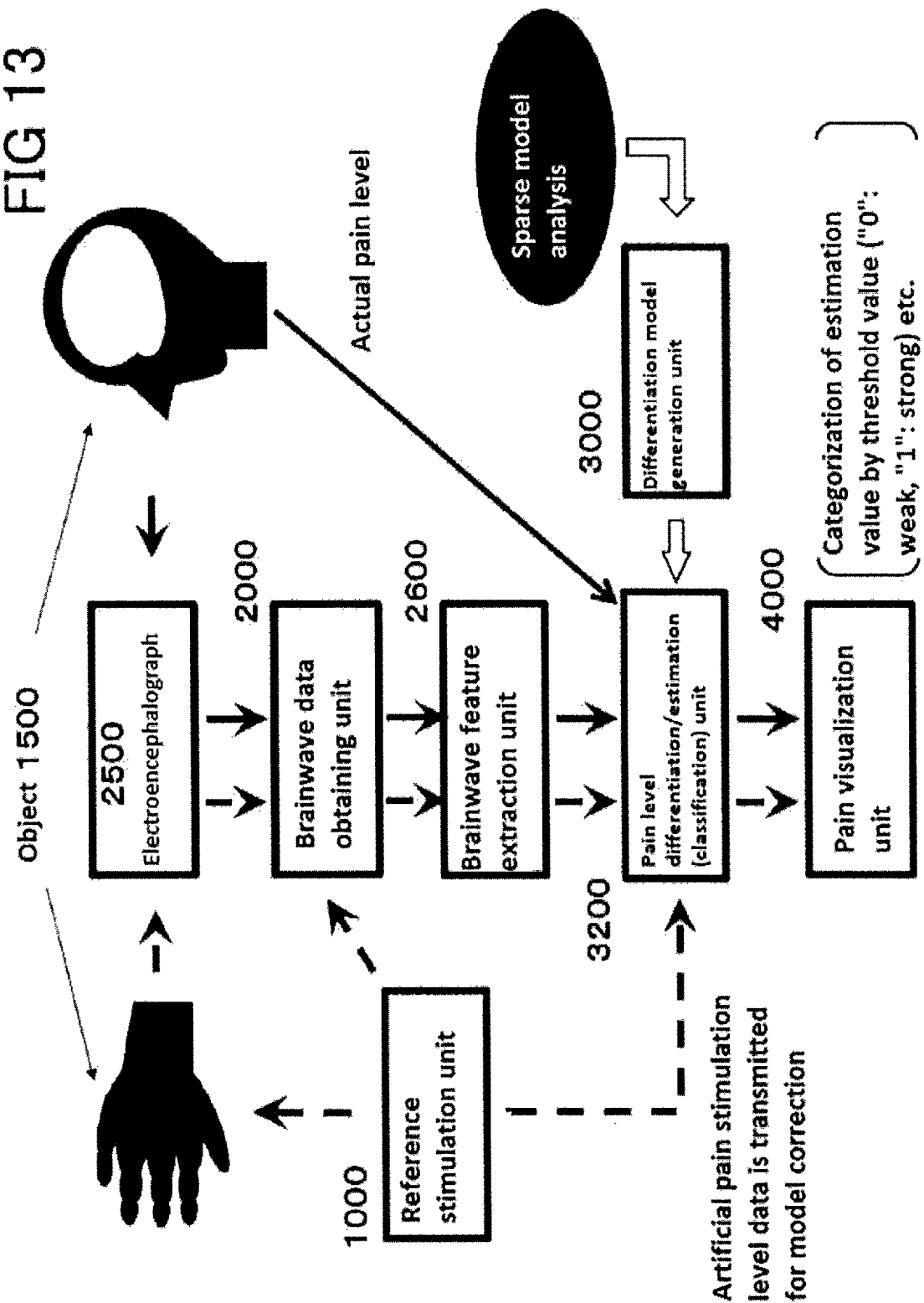
FIG. 13 is an example of a block diagram showing the functional configuration of the invention.

FIG. 13 describes a schematic diagram of the apparatus of the invention. An embodiment of a measurement apparatus therein is described. A reference stimulation unit 1000 is provided together with or separately from a brainwave data obtaining unit 2000. In regards to an actual pain differentiation/estimation process (solid line), the brainwave data obtaining unit performs step a) for obtaining brainwave data from an electroencephalograph 2500. A brainwave feature is extracted from raw data of a brainwave at a brainwave feature extraction unit 2600. At a pain level differentiation/estimation unit 3200, a pain level is fitted or estimated by a differentiation model obtained in advance by sparse model analysis of a differentiation model generation unit 3000. For a correction process or a verification of the installed differentiation algorithm (dotted line arrow), brainwave data synchronized with stimulation emitted to an object (1500) from the reference stimulation unit 1000 is acquired at the brainwave data obtaining unit 2000. The reference stimulation unit 1000 also transmits reference stimulation intensity level data to a (pain level) differentiation/estimation unit 3200 to correct the differentiation algorithm. An estimation value at the pain level differentiation/estimation unit 3200 is made visible at a pain visualization unit 4000. For example, estimation values are categorized (0=weak, 1=strong) by a threshold value or the like.

Figure 14:
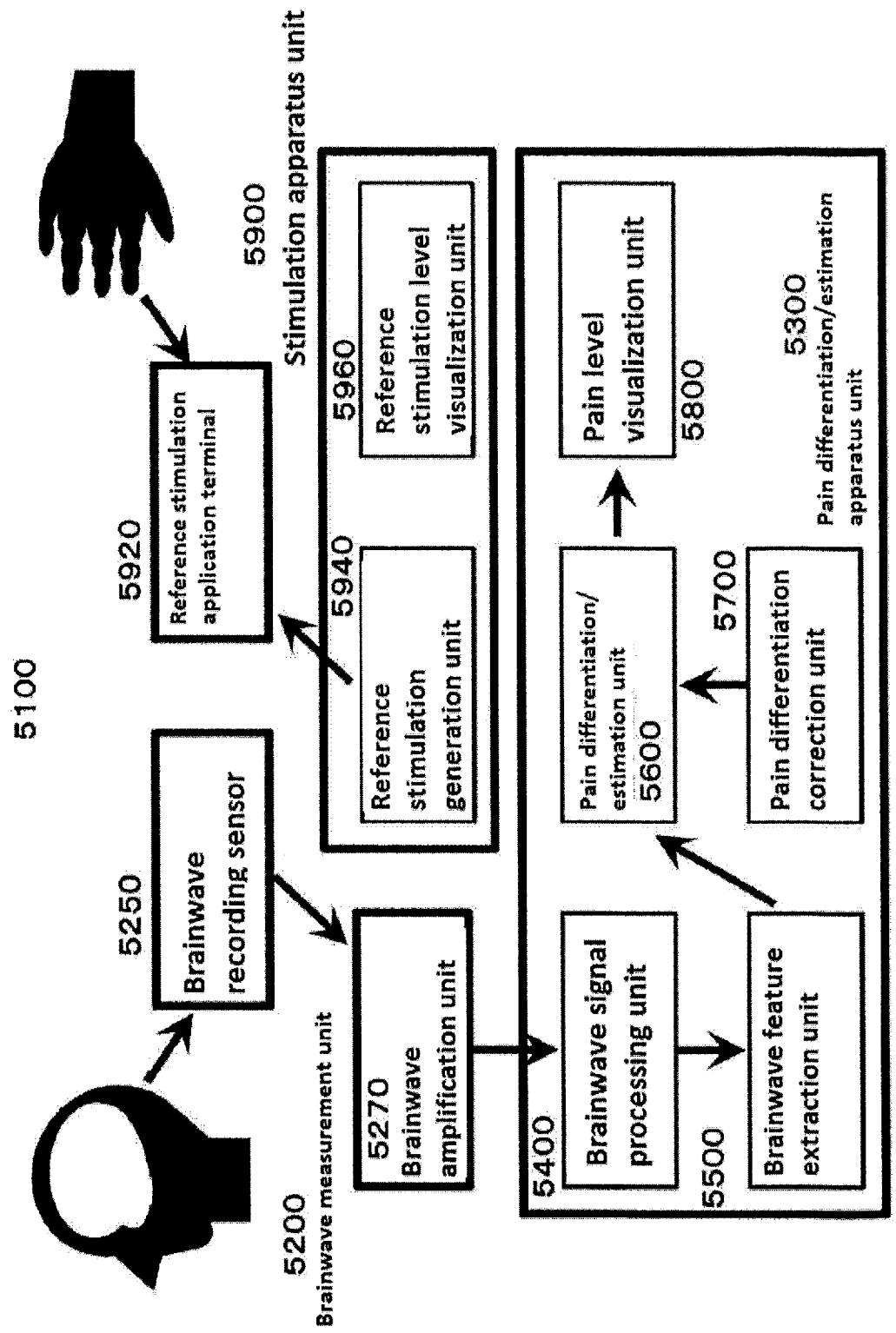
FIG. 14 is an example of a block diagram showing the functional configuration of the invention.

FIG. 14 is a block diagram showing a functional configuration of a pain differentiation/classification system 5100 of one embodiment (it should be noted that some of the configuration diagrams are optional constituents that can be omitted). The system 5100 comprises a brainwave measurement unit 5200, which internally comprises or externally connects to a brainwave recording sensor 5250 and optionally a brainwave amplification unit 5270. Signal processing of a pain regression model and differentiation/estimation are performed at a pain differentiation/estimation apparatus unit 5300. In the pain differentiation/estimation apparatus unit 5300, brainwave signals are processed at a brainwave signal processing unit 5400 (and a brainwave feature is extracted at a brainwave feature extraction unit 5500 as needed), pain is differentiated/estimated at a pain level differentiation/estimation unit 5600, and pain is (optionally) made visible at a pain level visualization unit 5800. The pain level differentiation/estimation unit 5600 is installed with an algorithm identified by a differentiation model creation unit using existing database and sparse model analysis to differentiate/estimate the real-time pain level. The system also comprises a stimulation apparatus unit 5900 internally or externally. The stimulation apparatus unit 5900 comprises a reference stimulation application apparatus unit (terminal) 5920, contributing to differentiation of the pain level of a patient. The stimulation apparatus unit also comprises a reference stimulation generation unit 5940 and optionally a reference stimulation level visualization unit 5960. The sparse model analysis of the invention, or a regression model for differentiation obtained thereby, is stored inside a differentiation unit. FIG. 4 shows a specific chart.

Figure 15:
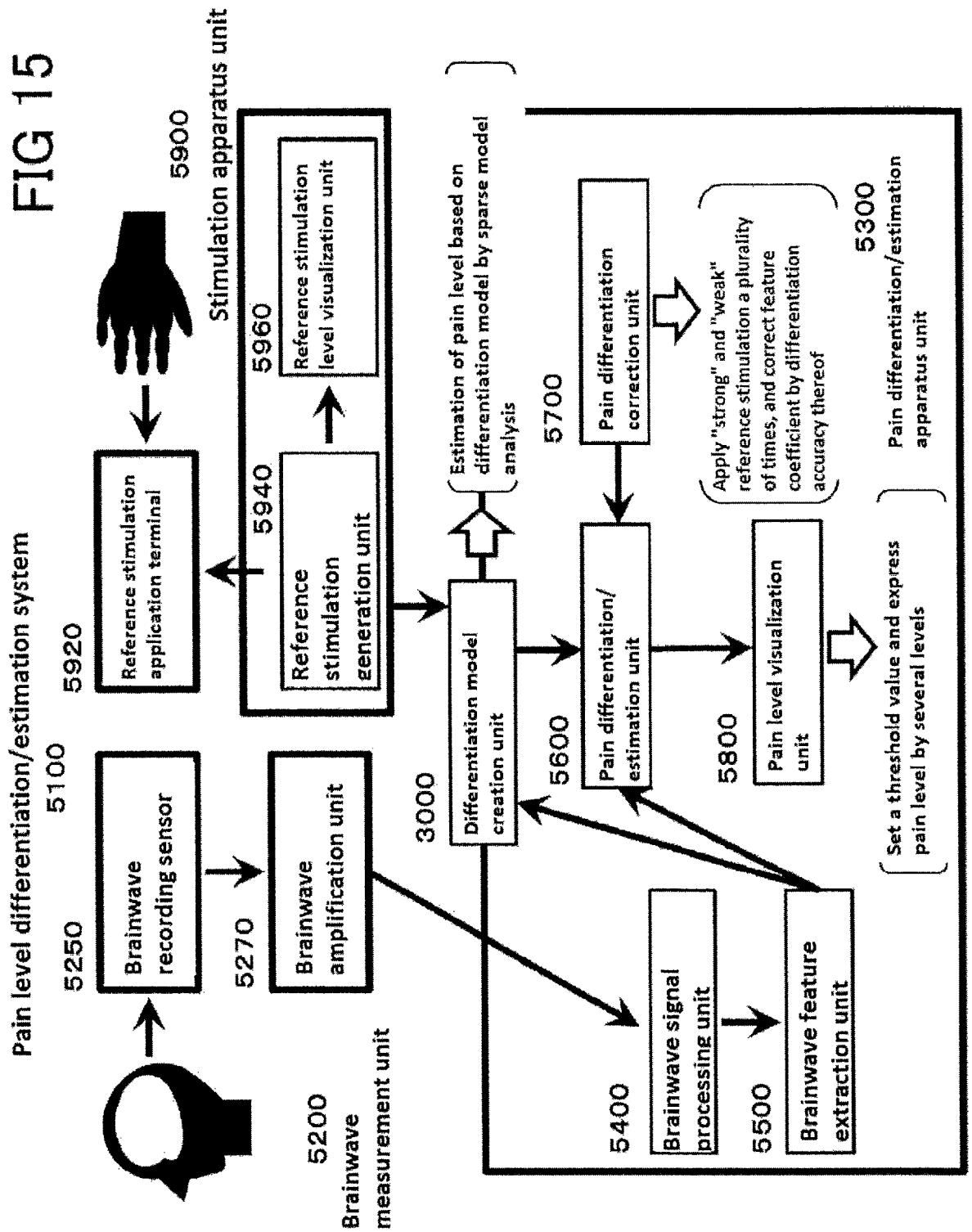
FIG. 15 is a diagram showing the link with the sparse model analysis in FIG. 14.

FIG. 15 shows the involvement of sparse modeling in more detail.

In this manner, the pain differentiation/classification system 5100 comprises the brainwave measurement unit 5200 and the pain differentiation/estimation apparatus unit 5300 and optionally the stimulation apparatus unit (reference stimulation unit) 5900. The pain level differentiation/estimation unit 5600 is materialized, for example, by a computer comprising a processor and a memory. In such a case, the pain level differentiation/estimation unit 5600 makes a processor function optionally as the brainwave amplification unit 5270, brainwave signal processing unit 5400, (optionally) pain level differentiation/estimation unit 5600, (optionally) pain level visualization unit 5800, and the like when a program (differentiation algorithm) created by the differentiation model generation unit 3000 is executed by the processor. The pain level differentiation/estimation unit also optionally makes the processor perform reference stimulation vocalization and visualization. The system 5100 or apparatus 5300 of the invention can be materialized, for example, with a dedicated electrical circuit. A dedicated electrical circuit can be a single integrated circuit or a plurality of electrical circuits. A brainwave data obtaining unit and pain classifier generation unit can have the same configuration as the pain estimation apparatus.

The brainwave measurement unit 5200 obtains a plurality of brainwave data by measuring a brainwave a plurality of times from an object being estimated via an electroencephalograph (brainwave recording sensor 5250). An object being estimated is an organism in which a change in brainwave is induced by pain, which does not need to be limited to humans.

The pain level differentiation/estimation unit 5600 generates or stores a regression model for differentiation/estimation created by the differentiation model generation unit 3000 that is internal or external to the apparatus. A differentiation algorithm generated by sparse model analysis (regression model) is for estimating or classifying the magnitude of pain from amplitudes of a plurality of brainwave data. In other words, the pain level differentiation/estimation unit 5600 can generate or store a regression model for estimating or classifying pain of an object from brainwave data.

The brainwave recording sensor 5250 measures electrical activity generated in the brain of an object being estimated with an electrode on the scalp. The brainwave recording sensor 5250 then outputs the result of measurement, brainwave data. Brainwave data can be amplified as needed.

Next, the processing or method of an apparatus configured in the manner described above is described. FIG. 12 is a flowchart showing a series of processing. The model regression equation generation aspect involves S100 to S400. A pain level differentiation/classification apparatus is generated at S400.

Stimulation of a plurality of levels (magnitude) of stimulation intensities is applied to an object through the reference stimulation unit 1000 (see FIG. 13) (S100).

Next, brainwave data (brainwave amplitude standard data such as amplitude data) is obtained (S200). Brainwave data is obtained by the brainwave data obtaining unit 2000 in FIG. 13. In the context of FIG. 14, a plurality of brainwave data is obtained as brainwave data (e.g., amplitude data) by measuring a brainwave a plurality of times from an object being estimated via the electroencephalograph (brainwave recording sensor) 5250 by the brainwave measurement unit 5200. The brainwave measurement unit 5200 can measure brainwaves at a plurality of different times. Sparse model analysis is performed at the differentiation model generation unit 3000 (see FIG. 13) (S300). When a regression coefficient is optionally judged to be a suitable value after fitting by sparse model analysis, the pain level differentiation/estimation unit 3200 (see FIG. 13) can classify pain levels by using the regression model (also known as a differentiation model) (S400). After generating a regression model, calibration can be performed by the reference stimulation unit 1000 (see FIG. 13) as needed.

The sparse modeling of the invention can be expressed as follows. Specifically, in one aspect, the present invention provides a differentiation algorithm for classifying pain of an object being estimated based on a brainwave of the object being estimated, comprising: a) stimulating the object being estimated with a plurality of levels of stimulation intensity; b) obtaining brainwave data of the object being estimated corresponding to the stimulation intensity; c) extracting a brainwave feature from the brainwave data; and d) inputting the feature into the sparse model analysis, approximating the feature to quantitative and qualitative levels of pain, estimating and differentiating a pain level, and determining an algorithm (including a feature coefficient and intercept).

Alternatively, the present invention provides an apparatus for differentiating or classifying pain of an object being estimated based on a brainwave of the object being estimated, the apparatus comprising: a) a stimulation unit for stimulating the object being estimated with a plurality of levels of stimulation intensity; b) a data obtaining unit for obtaining brainwave data or analysis data thereof of the object being estimated corresponding to the stimulation intensity; c) a brainwave feature extraction unit for extracting a brainwave feature from the brainwave data or analysis data thereof; and d) a pain level differentiation/estimation unit for inputting the feature into sparse model analysis and approximating the feature to at least one of a quantitative level and a qualitative level of pain to estimate or differentiate a pain level.

In another aspect, the present invention provides a program for making a computer execute a method of differentiating or estimating pain of an object being estimated based on a brainwave of the object being estimated. The method executed by the program comprises: a) stimulating the object being estimated with a plurality of levels of stimulation intensity; b) obtaining brainwave data or analysis data thereof of the object being estimated corresponding to the stimulation intensity; c) extracting a brainwave feature from the brainwave data or analysis data thereof; and d) inputting the feature into sparse model analysis, and approximating the feature to at least one of a quantitative level and a qualitative level of pain to estimate or differentiate a pain level. Alternatively, the present invention provides a recording medium storing the program described above.

The present invention would have generality that is compatible with various pain types and pain patterns from its use. The present invention is not only effective in differentiating a pain level of a known object, but also capable of differentiating, predicting, and classifying pain of an unknown object by providing a known differentiation algorithm created or installed above. In such a case, an estimation value is obtained using real-time pain feature of an unknown object and parameters of a differentiation/estimation algorithm (regression coefficient, intercept, threshold value, and the like) determined based on pain database of known objects, and a specific threshold value is used to determine pain levels thereof. For example, the following known differentiation algorithm can be adapted to the unknown object measurement data in a regression model identified by a LASSO analysis method.

$$Est_i = \Sigma(Test_i \times \beta_j) + C \qquad \text{[Numeral 3]}$$

i. pain level low: $Est_i <$ Threshold
ii. pain level high: $Est_i >$ Threshold
Est: estimation value
Test: measurement feature
$\beta$: partial regression coefficient
C: intercept
i: number of observations
j: number of features The present invention can differentiate, classify, or predict pain of known and unknown objects with fewest possible brainwave features for differentiating pain levels of known objects by providing a differentiation algorithm.

Examples of such features include the following.

(Representative Features)

Mean amplitude (Fz, Cz, C3, C4)

Fz: δ (1 to 3 Hz), θ (4 to 7 Hz), α (8 to 13 Hz), β (14 to 30 Hz), γ (31 to 100 Hz)

Cz: 5 bands <δ (1 to 3 Hz), θ (4 to 7 Hz), α (8 to 13 Hz), β (14 to 30 Hz), γ (31 to 100 Hz)>

C3: 5 bands <δ (1 to 3 Hz), θ (4 to 7 Hz), α (8 to 13 Hz), β (14 to 30 Hz), γ (31 to 100 Hz)>

C4: 5 bands <δ (1 to 3 Hz), θ (4 to 7 Hz), α (8 to 13 Hz), β (14 to 30 Hz), γ (31 to 100 Hz)> and the like The frequency power and the like described above can also be used.

In another aspect of the invention, a technology for differentiating/estimating a pain level can be provided while presuming that a regression model is not created every time. In such a case, the method of the invention comprises: c) providing a regression model for sparse model analysis of a pain level of the object being estimated; d) obtaining brainwave data (for measurement) or analysis data thereof of the object being estimated; e) extracting a brainwave feature for measurement from the brainwave data for measurement or analysis data thereof; f) calculating a corresponding pain level by fitting the brainwave feature for measurement to a regression model; and g) optionally displaying the pain level. In this regard, a regression model for sparse model analysis on a pain level of an object being estimated can be prepared by calculating a regression model for sparse model analysis on a pain level in advance for the object being estimated and storing the model in an appropriate recording apparatus or a recording medium. Alternatively, such a regression model can be provided as a model that is standardized to a certain extent. In such a case, sparse model analysis for the same object being estimated is not always required. A regression model calculated for a similar age group or for other subjects with a similar or same attribute. In such a case, a method of generating a regression model described below in <Regression model generation> can be used.

Alternatively, the present invention provides an apparatus for differentiating or classifying pain of an object being estimated based on a brainwave of the object being estimated, provided with a regression model (also referred to as a differentiation model) in advance. The apparatus comprises: c) a regression model provision unit for providing a regression model for sparse model analysis of a pain level of the object being estimated; d) a measurement data obtaining unit for obtaining brainwave data (for measurement) or analysis data thereof of the object being estimated; e) a measurement feature extraction unit for extracting a brainwave feature for measurement from the brainwave data for measurement or analysis data thereof; f) a pain level calculation unit for calculating a corresponding pain level by fitting the brainwave feature for measurement to a regression model; and g) optionally a pain level display unit for displaying the pain level.

Alternatively, the present invention provides a program for making a computer execute a method of differentiating or classifying pain of an object being estimated based on a brainwave of the object being estimated. The method provided by the program comprises: c) providing a regression model for sparse model analysis of a pain level of the object being estimated; d) obtaining brainwave data (for measurement) or analysis data thereof of the object being estimated; e) extracting a brainwave feature for measurement from the brainwave data for measurement or analysis data thereof; f) calculating a corresponding pain level by fitting the brainwave feature for measurement to a regression model; and g) optionally displaying the pain level. Alternatively, the present invention provides a recording medium storing the program described above. While a regression model can be calculated by any methodology described in the section of <Regression model generation>, the regression model can be generated by another methodology or generated in advance (case where steps up to S400 are performed separately in FIG. 12).

Step d) is a step for obtaining brainwave data (e.g., amplitude data) of the object being estimated (S500). This step is a step for obtaining brainwave data from an object being estimated on which measurement is intended, regardless of whether some type of simulation or treatment is applied. Any methodology can be used as long as it is a methodology that can obtain brainwave data. The same methodology as obtaining brainwave data used in step a) can be used. Generally, the same methodology is used.

Subsequently, a brainwave feature is extracted in step e) in the present invention. The same or different methodology from brainwave feature extraction used in step b) can be used. Generally, the same methodology is used.

Step f) is a step for calculating a corresponding pain level by fitting the brainwave feature for measurement to a regression model (pain classification, S600). A regression model is referred to as a "pain classification instrument" or "pain prediction instrument" in association with the pain level of an object being estimated. For example, when a brainwave amplitude associated with pain exhibits a decreasing pattern, and pain classifier classifies "strong pain" and "weak pain", brainwave data (e.g., amplitude data) detected to be lower than such a value is classified as "strong pain", and greater brainwave data (e.g., amplitude data) detected is classified as "weak pain". For example, if a value of a pain classification instrument exhibits a standardized brainwave absolute amplitude of "0.7", brainwave amplitude data recorded online is converted to an absolute value and standardized based on existing data, and then "0.8" is classified as feeling "weak pain", and "0.2" is classified as feeling "strong pain".

In one embodiment, brainwave data (e.g., amplitude data) can be fitted to the regression model with the original mean value or normalized mean value. Such a mean value can be, for example, a mean value between 15 seconds to 120 seconds.

This aspect is described based on FIG. 13. The brainwave data obtaining unit 2000 in addition to the pain level differentiation/estimation unit 3200 are referenced in FIG. 13. In such a case, brainwave data can be obtained via the electroencephalograph 2500 from the object 1500 as described in the section of <Regression model generation>. Specifically, the brainwave data obtaining unit 2000 is configured to be connectable to the object (1500), and the brainwave data obtaining unit 2000 is configured to comprise or to be connected to an electroencephalograph that is or can be connected to the object 1500, so that brainwave data obtained from the object (1500) can be obtained (2500). The pain level differentiation/estimation unit 3200, which is also referred to as a pain level calculation unit, is configured to store a regression model produced by the differentiation model generation unit 3000 or receive a regression model generated separately, and optionally configured to be capable of referencing. Such a connection configuration can be wired or wireless connection. An artificial pain stimulation level data can be transmitted to the pain level differentiation/estimation (classification) unit 3200 for model correction from the reference stimulation unit 1000. A differentiation model from the sparse model analysis of the invention can be introduced or calculated at the differentiation model generation unit 3000.

FIG. 14 is a block diagram showing a functional configuration of the pain level differentiation/estimation or regression model generation system 5100 in one embodiment. The system 5100 comprises the brainwave measurement unit 5200, which internally comprises or externally connects to the brainwave recording sensor 5250 and optionally the brainwave amplification unit 5270. Signal processing and differentiation/estimation of pain are performed at the pain level differentiation/estimation apparatus unit 5300. In the pain level differentiation/estimation apparatus unit 5300, brainwave signals are processed at the brainwave signal processing unit 5400, (optionally) a regression model is stored and pain is differentiated/estimated based thereon at the pain level differentiation/estimation unit 5600, and (optionally) pain is made visible at the pain level visualization unit 5800. The system also comprises the stimulation apparatus unit 5900 internally or externally. The stimulation apparatus unit 5900 comprises the reference stimulation application apparatus unit (terminal) 5920, contributing to correction of a patient pain level differentiation/estimation instrument. The stimulation apparatus unit also (optionally) comprises the reference stimulation generation unit 5940.

In this manner, the pain level differentiation/estimation system 5100 comprises the brainwave measurement unit 5200 and the pain differentiation/estimation apparatus unit 5300. The pain differentiation/estimation apparatus unit 5300 that stores a regression model is materialized, for example, by a computer comprising a processor and a memory. In such a case, the pain differentiation/estimation apparatus unit 5300 makes a processor function optionally as the brainwave amplification unit 5270, brainwave signal processing unit 5400, (optionally) pain differentiation/estimation unit 5600, (optionally) pain level visualization unit 5800, and the like when a program stored in the memory is executed by the processor. The pain differentiation/estimation apparatus unit can also optionally make the processor perform reference stimulation generation and visualization. The system 5100 or apparatus 5300 of the invention can be materialized for example, with a dedicated electrical circuit. A dedicated electrical circuit can be a single integrated circuit or a plurality of electrical circuits. A brainwave data obtaining unit and pain classifier generation unit can have the same configuration as the pain level estimation apparatus.

The brainwave measurement unit 5200 obtains a plurality of brainwave data by measuring a brainwave plurality of times from an object being estimated via a brainwave meter (brainwave recording sensor 5250). An object being estimated is an organism in which a change in brainwave is induced by pain, which can be an organism having a pain sensing nerve (e.g., vertebrate such as mammals and avian (including livestock animals, pet animals, and the like) and is not limited to humans.

The pain level differentiation/estimation unit 5600 differentiates or classifies a pain level from amplitudes of a plurality of brainwave data based on a regression model. In other words, the pain differentiation/estimation unit 5600 differentiates or classifies pain of an object from brainwave data based on a regression model.

The brainwave recording sensor (electroencephalograph) 5250 measures electrical activity generated in the brain of an object being estimated with an electrode on the scalp. The brainwave recording sensor 5250 then outputs the result of measurement, brainwave data. Brainwave data can be amplified as needed.

FIG. 15 shows a diagram with additional descriptions of the relationship between a pain differentiation/estimation apparatus and sparse model analysis described as a basic block diagram in FIG. 14. In this regard, the differentiation model creation unit 3000 is depicted, where an estimation base of a pain level based on a differentiation model (also referred to as a regression model) according to sparse model analysis is provided. The pain differentiation correction unit 5700 is an optional part, but is capable of applying "strong" and "weak" reference stimulation a plurality of times and correcting a coefficient of a feature depending on the differentiation accuracy therein. At the pain level visualization unit 5800, pain levels can be expressed in several levels by setting a threshold value.

Next, a process or method of an apparatus configured in the above manner is described. FIG. 12 is a flowchart showing a series of processes. In this aspect, processes from S400 to S600 can be involved. They are steps after generating a regression model (also referred to as a differentiation model, or pain classification instrument/pain prediction instrument) at S400. Alternatively, if a regression model is available separately (the model is obtained and stored in advance, etc.), the process starts from S400.

A regression model can be generated at a different differentiation model creation unit 3000 (see FIG. 13), and stored in advance in the pain level differentiation/estimation unit 3200 (see FIG. 13), and the pain level differentiation/estimation unit 3200 can be configured to be able to receive value data. Alternatively, if the differentiation model generation unit 3000 is installed, a model can be stored in the generation unit. A recording medium can be provided separately. This value can be received through communication.

Next, brainwave data is obtained from an object (S500). The brainwave data can be obtained using the same technology described for S200. While the same embodiment can be employed, the same apparatus or device as S200 does not need to be used, which can be the same or different.

Figure 16:
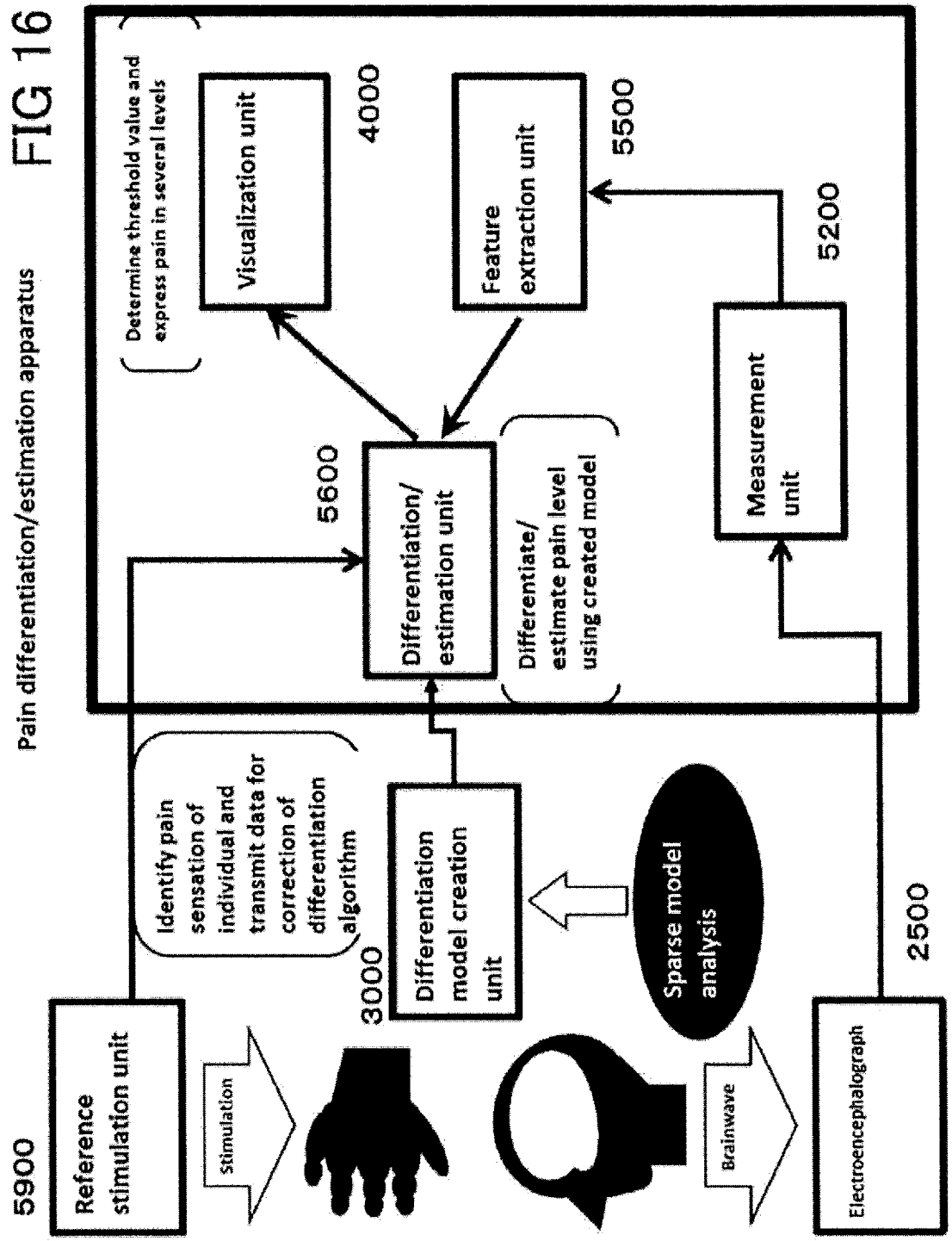
FIG. 16 is another example of a block diagram showing the functional configuration of the invention.

Next, brainwave data (e.g., amplitude data) obtained at S500 is fitted to a regression model generated by sparse model analysis, and pain levels corresponding to the brainwave data are classified (S600). Such pain classification can be configured so that a certain phrase (strong pain, weak pain, or the like) is displayed or vocalized when a predetermined value is outputted, or configured so that an actual value and a regression model are displayed in juxtaposition to allow a user (clinician) to review the value. FIG. 16 shows an exemplary embodiment. As shown in FIG. 16, a regression model generated by sparse model analysis is stored in the differentiation model generation unit 3000 and used in the pain differentiation/estimation apparatus. A result obtained by the sparse model analysis of the invention is introduced into the differentiation model generation unit 3000. Pain sensitivity of an individual is identified from the reference stimulation unit 5900, and data for correcting a differentiation algorithm is transmitted. At the differentiation/estimation unit 5600, a pain level is differentiated/estimated using the created model. The visualization unit 5800 can express pain as several levels after determining any threshold value.

<Regression Model Generation>

In another aspect, the present invention provides a technology for creating a regression model. In this regard, the present invention provides a method for generating a regression model for differentiating or estimating pain of an object being estimated based on a brainwave of the object being estimated. The method comprises: a) obtaining brainwave data for a model or analysis data thereof corresponding to stimulation intensity for a model; b) extracting a brainwave feature for a model from the brainwave data or analysis data thereof; and c) setting a pain level of interest, introducing the brainwave feature for a model (independent variable) and the pain level (dependent variable) into sparse model analysis, finding a suitable λ (preferably the optimal λ), and determining a parameter (partial regression coefficient) for the brainwave feature for a model and a constant (intercept) of an algorithm corresponding to the suitable λ (preferably the optimal λ) to generate a regression model.

Alternatively, the present invention provides an apparatus for generating a regression model for differentiating or classifying pain of an object being estimated based on a brainwave of the object being estimated. The apparatus comprises: a) a model data obtaining unit for obtaining brainwave data for a model or analysis data thereof corresponding to stimulation intensity for a model; b) a feature extraction unit for extracting a brainwave feature for a model from the brainwave data or analysis data thereof; and c) a regression model generation unit for setting a pain level of interest, introducing the brainwave feature for a model and the pain level into sparse model analysis, finding a suitable λ (preferably the optimal λ), and determining a parameter (partial regression coefficient) for the brainwave feature for a model and a constant (intercept) of an algorithm corresponding to the suitable λ (preferably the optimal λ) to generate a regression model.

Alternatively, the present invention provides a program for making a computer execute a method for generating a regression model for differentiating or classifying pain of an object being estimated based on a brainwave of the object being estimated. The method executed by the program comprises: a) obtaining brainwave data for a model or analysis data thereof corresponding to stimulation intensity for a model; b) extracting a brainwave feature for a model from the brainwave data or analysis data thereof; and c) setting a pain level of interest, introducing the brainwave feature for a model and the pain level into sparse model analysis, finding a suitable λ (preferably the optimal λ), and determining a parameter (partial regression coefficient) for the brainwave feature for a model and a constant (intercept) of an algorithm corresponding to the suitable λ (preferably the optimal λ) to generate a regression model. Alternatively, the present invention provides a recording medium storing the program described above.

This aspect is described based on FIG. 13. The brainwave data obtaining unit 2000 in addition to the differentiation model creation unit 3000 are referenced in FIG. 13. In such a case, brainwave data can be obtained via the electroencephalograph from the object as described in the section of <Regression model generation>. Specifically, the brainwave data obtaining unit 2000 is configured to be connectable to the object 1500, and the brainwave data obtaining unit 2000 is configured to comprise or to be connected to an electroencephalograph that is or can be connected to the object (1500), so that brainwave data obtained from the object (1500) is obtained (2500).

In the embodiment described above, the range of the value of magnitude of pain is set so that the value of Pmax, which is the magnitude of pain corresponding to the upper limit value Amax of a brainwave amplitude, would be 1, or the value of Pmin, which is the magnitude of pain corresponding to the lower limit value Amin of the brainwave amplitude, would be 0, but the range of values is not limited thereto. For example, the magnitude of pain can be represented by 0 to 100. In such a case, the pain level differentiation/estimation unit 3200 can estimate the value Px of magnitude of pain by the following equation.

$$Px = P\max \times (Ax - A\min)/(A\max - A\min) \quad \text{[Numeral 4]}$$

While Amax and Amin are brainwave amplitudes, they can be an estimation value calculated with a regression model as follows.

$$Px = P\max \times (\text{Est}x - \text{Mod}\min)/(\text{Mod}\max - \text{Mod}\min) \quad \text{[Numerical 5]}$$

Estx: model estimation value calculated from a feature
Modmin: minimum value for differentiation/estimation determined with an existing model
Modmax: maximum value for differentiation/estimation determined with an existing model Curve fitting was described above as an example of generating a pain classifier by analyzing a plurality of brainwave data, but this is not a limiting example. For example, a value corresponding to large stimulation can be identified using a learning model for estimating a brainwave amplitude in response to large simulation from a brainwave amplitude corresponding to small stimulation. In such a case, large stimulation does not need to be applied to an object being estimated, so that physical burden on an object being estimated can be mitigated. Further, a predetermined value can be used as the upper limit value of brainwave amplitudes. The predetermined value is for example 50 µV to 100 µV, which can be experimentally or empirically determined. In such normal analysis, data from about plus or minus 50 µV to 100 µV is eliminated as an artifact removal method. Such artifact removal can also be performed in the present invention as needed.

Stimulation applied to an object being estimated by the stimulation apparatus unit 5900 (see FIG. 14) is not limited to electrical stimulation and thermal stimulation. Any type of stimulation can be applied as long as the magnitude of pain sensed by the object being estimated changes in accordance with the magnitude of stimulation.

Some or all of the constituent elements of the pain estimation apparatus in each of the embodiments described above can be comprised of a single system LSI (Large Scale Integration). For example, the pain differentiation/estimation apparatus unit 5300 can be comprised of a system LSI having optionally the (brainwave) measurement unit 5200 and optionally the stimulation application unit 5900.

In each of the embodiments described above, each constituent element can be materialized by being configured with a dedicated hardware or by executing software program that is suited to each constituent element. Each constituent element can be materialized by a program execution unit such as a CPU or a processor reading out and executing a software program recorded on a recording medium such as a hard disk or semiconductor memory. In this regard, software materializing the pain estimation apparatus of each of the embodiments described above or the like can be a program such as those described below.

Specifically, the program makes a computer execute a method of differentiating or classifying pain of an object being estimated based on a brainwave of the object being estimated, comprising: a) obtaining brainwave data for a model or analysis data thereof corresponding to stimulation intensity for a model; b) extracting a brainwave feature for a model from the brainwave data or analysis data thereof; c) setting a pain level of interest, introducing the brainwave feature for a model and the pain level into sparse model analysis, finding a suitable λ (preferably the optimal λ), and determining a parameter (partial regression coefficient) for the brainwave feature for a model and a constant (intercept) of an algorithm corresponding to the suitable λ (preferably the optimal λ) to generate a regression model; d) obtaining brainwave data (for measurement) or analysis data thereof of the object being estimated; e) extracting a brainwave feature for measurement from the brainwave data for measurement or analysis data thereof; f) calculating a corresponding pain level by fitting the brainwave feature for measurement to a regression model; and g) optionally displaying the pain level.

Alternatively, the program makes a computer execute a method of differentiating or classifying pain of an object being estimated based on a brainwave of the object being estimated, comprising: a) stimulating the object being estimated with a plurality of levels of stimulation intensity; b) obtaining brainwave data or analysis data thereof of the object being estimated corresponding to the stimulation intensity; c) extracting a brainwave feature from the brainwave data or analysis data thereof; and d) inputting the feature into the sparse model analysis, and approximating the feature to at least one of quantitative and qualitative levels of pain to estimate or differentiate a pain level.

Alternatively, the program makes a computer execute a method of differentiating or classifying pain of an object being estimated based on a brainwave of the object being estimated, comprising: c) providing a regression model for sparse model analysis of a pain level of the object being estimated; d) obtaining brainwave data (for measurement) or analysis data thereof of the object being estimated; e) extracting a brainwave feature for measurement from the brainwave data for measurement or analysis data thereof; f) calculating a corresponding pain level by fitting the brainwave feature for measurement to a regression model; and g) optionally displaying the pain level.

Alternatively, the program makes a computer execute a method of generating a regression model for differentiating or estimating pain of an object being estimated based on a brainwave of the object being estimated, comprising: a) obtaining brainwave data for a model or analysis data thereof corresponding to stimulation intensity for a model; b) extracting a brainwave feature for a model from the brainwave data or analysis data thereof; and c) setting a pain level of interest, introducing the brainwave feature for a model and the pain level into sparse model analysis, finding a suitable λ value (preferably the optimal λ), and determining a parameter (partial regression coefficient) for the brainwave feature for a model and a constant (intercept) of an algorithm corresponding to the suitable λ (preferably the optimal λ) to generate a regression model.

(Determination of Instantaneous Pain)

In one aspect, the present invention provides a method of differentiating or evaluating pain, comprising comparing brainwave data or analysis data thereof from some or all of a period between the earliest point among evoked brainwave potential, early event related potential, and 250 msec and 2000 msec from application of target stimulation with brainwave or analysis data thereof after the same time from application of reference stimulation. Conventionally, pain was generally determined by observing up to a P300 component after observing an evoked brainwave potential (P100). One of the important points of the present invention is that observation of regions later than intermediate event related potential P300 enables detailed analysis of pain, so that occurrence and level of instantaneous pain can be distinguished using a brainwave feature whose synchronicity is difficult to find in persistent pain.

One embodiment, comprises, as criteria of determination, whether the brainwave data from a period between the earliest point among evoked brainwave potential, early event related potential, and 250 msec and 2000 msec has a persistent property. If there is a potential component with a peak after the early event related potential, it is determined as conventional P300.

In one embodiment, the brainwave data or analysis data thereof comprises brainwave data or analysis data thereof in some or all of a range from intermediate time to 2000 msec.

In an embodiment of the invention, an intermediate time frame roughly falls under event related potential and includes the range where P200, N200, and P300 occur. Typically, the intermediate time frame can comprise a value in a range between 250 msec to 600 msec. The intermediate time frame can be continuously or comprehensively included, or extended from 250 to 600 msec or 300 to 600 msec. Alternatively, the intermediate time frame can be any numerical range, as long as the range starts after P200.

In one embodiment, some or all of brainwave data or analysis data thereof between the earliest point among evoked brainwave potential, early event related potential and 250 msec and 2000 msec comprises at least a 100 msec range. In one embodiment, an intermediate time frame is a time frame continuously covering from 300 msec or before to the vicinity of 600 msec.

In one embodiment, if a statistically significant difference is found with the at least 100 msec range, it is determined that persistence is found in the at least 100 msec range. It can be determined that there is a difference when there is a difference by visual inspection but no statistically significant difference. Meanwhile, it is advantageous to have a statistically significant difference in a preferred embodiment. In another embodiment, if the appearance is clearly persistence at 250 to 2000 msec, pain can be considered persistent even if there is a significant difference only fragmentally.

In one embodiment, the comparing comprises: measuring whether there is a persistent period where a value of brainwave data or analysis data thereof obtained from the target stimulation is different from a value of brainwave data or analysis data thereof obtained from the reference stimulation and, if there is the different persistent period, whether the values would be the same value again after becoming different; and if there is the persistent period and the values would not be the same value again, determining that there is unpleasant pain. Specifics are described below. For example, the following signal processing is first performed for verification in order to acknowledge a persistent component.

1) Whether there is a deviation from the activity of reference stimulation after application of stimulation. If there is from the time of application of stimulation, the component is not related to pain perception or cognition, but is possibly an artifact. 2) If the standard line of a brainwave is shifted significantly upward or downward in view of brainwave waveforms from each application of stimulation, and is eliminated when the standard line is returned to a baseline by linear correction, this is not referred to as a persistent component. 3) If a low frequency band component such as 0.02 Hz, 0.01 Hz, or 0.1 Hz is blocked, a persistent component is eliminated in accordance with the persistent period. Thus, if not falling under 1 or 2, and such a low frequency component is blocked and eliminated, the component can be identified as persistent ERP. After the persistent component is verified in the process described above, a time frame is set to determine the persistent period and starting point of persistent ERP, and an inferential statistical test such as t-test or ANOVA is performed to identify a significant difference between reference stimulation and pain stimulation, as shown in FIG. 19.

In one embodiment, the brainwave data or analysis data thereof is potential, a persistent period, or a combination thereof.

In another embodiment, the differentiation of pain is differentiation of a degree of unpleasantness of pain. Although not wishing to be bound by any theory, the present invention falls under "identifiable pain", or possibly can distinguish pain originating from a specific body part, pain due to external stimulation, and the like.

In one embodiment, the brainwave data or analysis data thereof is compared throughout the entire period from the earliest point among evoked brainwave potential, early event related potential, and 250 msec to 2000 msec.

In one of the preferred embodiments, the method of the invention further comprises analyzing the compared data using sigmoid function fitting. In other words, sample data of all subjects (standardized among individuals) are arranged in the order of no instantaneous pain and having instantaneous pain. A function approximated to sample data (e.g., sigmoid function or step function) is created. nlinfit of MATLAB code or the like can be used for the function approximation.

In one embodiment, the differentiation judges a positive component of brainwave data or analysis data thereof. In a specific embodiment, it is judged that there is pain when the positive component also persists after an intermediate time frame. In particular, a delayed persistent effect is understood as reflecting unpleasant pain that slowly arrives later, and is presumed to be a neurological reaction of *C fiber*.

Generally, intermediate event related potential such as P300 reaches peak potential at about 300 to 400 msec. However, this can vary depending on details of processed information or load. Thus, a shift to a positive direction generally exhibits non-persistence, starting before 300 msec and reaching a peak at 300 to 400 msec. However, persistence unexpectedly continues without returning to the baseline even after 2000 msec from application of stimulation in some cases, as shown in the present invention. Pain can be differentiated in detail using this as an indicator. It was unexpected to observe an example where it never returns and continues for two seconds in the present invention. The discovery of a persistent positive component as an important indicator for pain was unexpected. In particular, ERP component that persists even after the intermediate period shows that even isolated pain stimulation is unpleasant and unpleasant feeling consciously continues even after the disappearance of stimulation. Acute pain such as nociceptive pain and pain stress associated therewith can be determined.

Each step is described below.

Figure 27:
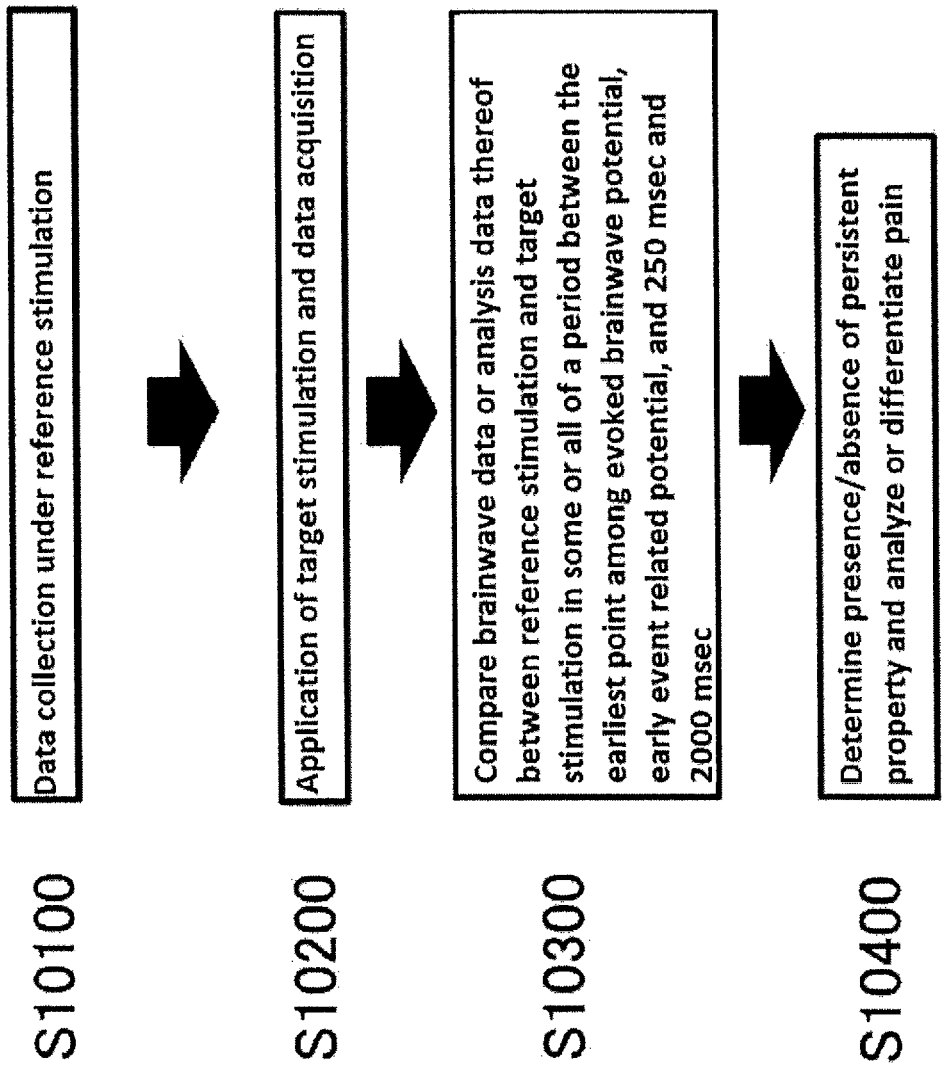
FIG. 27 is a representative flowchart in the implementation of the invention.

The methodology of the invention is described using the following schematic diagram (FIG. 27).

Step S10100: Data collection under reference stimulation

S10100 is an optional step, which provides data used as the baseline (standard). To extract a brainwave feature associated with instantaneous pain, it is desirable to set the pain stimulation type and stimulation property to be the same as much as possible, and pain properties such as having pain/no pain or strong/weak have as small of a difference as possible. For example, when using high temperature stimulation, reference stimulation that is the standard for evaluation of pain is applied a plurality of times using, for example, stimulation that is not painful or has weak pain to collect brainwave data or analysis data thereof. Reference stimulation is standard (background) stimulation applied together with target stimulation described below. In order for an object to form short-term memory of standard stimulation, the frequency must be overwhelmingly greater, accounting for about 70% of the whole. Providing brainwave data or analysis data thereof obtained in advance or reading out stored data is also deemed equivalent to the step of data collection.

Step S10200: Application of target stimulation and data acquisition

S10200 is a step for randomly mixing and applying target stimulation and reference stimulation a plurality of times, or considering naturally applied stimulation as target stimulation, and collecting brainwave data or analysis data thereof in response to the stimulation. This step applies some type of stimulation (e.g., stimulation inducing pain) to an object, or considers a naturally generated stimulation as target stimulation, and measures or obtains model-use or actual brainwave data or analysis data thereof of an object being measured. In applying stimulation, a model system stimulates with a variety of stimulation (e.g., cold temperature stimulation, electrical stimulation, or the like) to obtain brainwave data (also referred to as brain activity data, amount of brain activity, or the like, including for example, amplitude data (EEG amplitude), frequency properties, and like) of the object being estimated corresponding to the stimulation intensity. Such brainwave data can be obtained using any methodology that is well known in the art. Brainwave data can be obtained by measuring an electrical signal of a brainwave, and displayed by potential (can be displayed by µV or the like) as amplitude data or the like. Frequency properties are displayed as power spectrum density or the like. Brainwave data or analysis data thereof can associate a difference with a conditional parameter (e.g., degree of unpleasantness of pain stimulation or the like) including a parameter related to stimulation of environment such as stimulation type or stimulation application environment based on an appropriate methodology.

Step S10300: Comparing brainwave data or analysis data thereof for reference stimulation and target stimulation in some or all of the period between the earliest point among evoked brainwave potential, early event related potential, and 250 msec and 2000 msec (see FIG. 19)

In some or all of the range between the earliest point among evoked brainwave potential, early event related potential, and 250 msec and 2000 msec, the point at which reference stimulation deviates for target stimulation is identified, and brainwave data or analysis data thereof are compared. In other words, this is a step of comparing brainwave data or analysis data thereof from some or all of a period between the earliest point among evoked brainwave potential, early event related potential, and 250 msec and 2000 msec with brainwave or analysis data thereof after the same time from application of reference stimulation. Preferably, it is determined whether brainwave data between the earliest point among evoked brainwave potential, early event related potential, and 250 msec and 2000 msec has a persistent property. If a persistent property is statistically confirmed, it can be differentiated that there is a specific type of pain for which unpleasantness of pain continues even after pain stimulation is physically eliminated. Miserable pain and instantaneous pain can be distinguished. Preferred measurement measures brainwave data or analysis data thereof in all or some of the range from the intermediate time frame to 2000 msec. Such measurement can be adjusted by an optionally equipped controlling mechanism in a system or program materializing the method of the invention. The intermediate time frame can be set to 250 msec to 600 msec, but there can be individual differences as well as a difference even within the same person, so that the time frame can be appropriately calibrated or appropriately changed after a measurement. An intermediate time frame is a range of event related potential, which can be calculated using any methodology that is known in the art.

Judgment of a difference can be materialized by a statistical methodology (see FIG. 19). Such a methodology can be optionally integrated into a system or program materializing the present invention, or provided externally. For example, the step of measuring whether there is a persistent period where a value of brainwave data or analysis data thereof obtained from the target stimulation is different from a value of brainwave data or analysis data thereof obtained from the reference stimulation and, if there is the different persistent period, whether the values would be the same value again after becoming different; and if there is the persistent period and the values would not be the same value again, determining that there is unpleasant pain is performed. This can also be optionally integrated into a system or program materializing the present invention or provided externally. Brainwave data or analysis data thereof is preferably potential, a persistent period, or a combination thereof, but other parameters can also be used. The present invention can be configured to allow any choice.

Comparative data can be further analyzed using sigmoid function fitting. A differentiation/estimation model is created for two, three, or more classifications in accordance with conditional parameters using a brainwave feature. One method is to create a plot diagram and fitting the diagram to an appropriate fitting function such as a sigmoid function pattern. Any methodology that is known in the art can be used for fitting. Specific examples of such fitting functions include, but are not limited to, a step function, Boltzmann function, double Boltzmann function, Hill function, logistic dose response, sigmoid Richards function, sigmoid Weibull function, and the like. A standard logistic function is particularly called a sigmoid function. A standard function or a modified form thereof is common and preferred. Optionally, a threshold value for determining pain can be set based on the sigmoid curve or the like when a regression coefficient for fitting to an appropriate function pattern such as the sigmoid function pattern is equal to or greater than a predetermined value. In this regard, this can be generated based on an inflection point for a sigmoid curve, but this is not a limiting example. Optionally, a pain classifier can be calibrated to maximize pain types or level classifications. A threshold value can be applied to level calculation or classification and used for determination of a therapeutic effect.

Thus, in a specific embodiment, the associating comprises setting a difference in pain and finding a feature associated with the difference based on conditions such as the environment and the stimulation, and generation of the pain determination means comprises applying a label that distinguishes a difference in the stimulation using the feature. In a specific embodiment, the generation of the pain determination means is achieved by sigmoid function fitting or machine learning.

Step S10400: Determine the presence/absence of persistent property, and analyze and differentiate pain.

This is an optional step for determining the presence/absence of a persistent property and analyzing pain. It was unexpected that pain can be determined by measuring and analyzing brainwave data or analysis data thereof in a range after the intermediate time frame. It was also unexpected that the presence of a persistent property in this range is related to specific pain.

A brainwave feature used has a temporal, spatial, or complex property comprised of the interaction thereof, such as amplitude, latency, persistent period of effect, distribution, or frequency power. Therefore, the relationship between stimulation or environment condition and feature can be identified by statistically comparing features (t-test or analysis of variance (ANOVA)) or by examining a continuous relationship (correlation or regression).

Obtained brainwave data can be optionally subjected to basic signal processing such as filtering, eye movement correction, or artifact removal. The data can be associated with a conditional parameter and a signal of the corresponding portion can be extracted to create a brainwave feature. For example, a mean value (arithmetic mean or geometric mean), other representative value (median or mode), entropy, frequency power, wavelet, mean, single run event related potential component, and the like can be used.

If a feature such as a persistent property is found, the feature can be associated with pain to create means for determining pain of an object. In this regard, a threshold value or a determination index can be set on a model curve obtained by fitting using the associated brainwave feature, and a threshold value can be set with a numerical value such as the quantity or level of threshold value potential or positive potential and used as a determination index.

Optionally, a model for differentiating/estimating pain from known or unknown stimulation or environment can be created using a feature identified by association.

A differentiation/estimation model for two, three, or more classifications of pain in accordance with conditional parameters can be created using a brainwave feature. For example, a plot diagram can be created and fitted to an appropriate fitting function such as a sigmoid function pattern as one method. Any methodology that is known in the art can be used for fitting. Specific examples of such fitting functions include, but are not limited to, a step function, Boltzmann function, double Boltzmann function, Hill function, logistic dose response, sigmoid Richards function, sigmoid Weibull function, and the like. A standard logistic function is particularly called a sigmoid function. A standard function or a modified form thereof is common and preferred.

Optionally, when a regression coefficient for fitting to an appropriate function pattern such as a sigmoid function pattern is equal to or greater than a predetermined value, a threshold value for determining pleasantness/unpleasantness can be set based on the sigmoid curve or the like. In this regard, a threshold value can be generated based on an inflection point for a sigmoid curve, but this is not a limiting example. Optionally, a pain classifier can be calibrated to maximize classification of levels of pleasantness/unpleasantness. A threshold value can be applied to distinguishing pain or calculating or classifying levels, and can be used in determining a therapeutic effect.

Therefore, in one specific embodiment, the associating can determine classification or difference in pain based on conditions such as certain stimulation, and find a feature associated with the classification or difference. In addition, generation of the pain determination means include applying a label for distinguishing a difference in the stimulation using the feature. In a specific embodiment, the generation of the pain determination means can be achieved by sigmoid function fitting or machine learning.

An actual medical apparatus can be configured to perform one or more steps of S10100 to S10400, but a determination instrument or determination value can be set in advance. In such a case, S10300 determines a feature as a standard using an existing data set of reference stimulation. This method calculates a z-value of a feature associated with reference stimulation based on the amount of activity in a rest segment where reference stimulation is not applied and the z-value is stored as data in advance. When data for target stimulation is newly recorded, z-value of the target stimulation is similarly calculated and compared with data for an existing reference stimulation value.

If the same subject is targeted, the step can comprise a step of succeeding or updating a determination instrument or determination value by using the previous pain determination means (value or the like).

Further, pain of an object can be determined by obtaining brainwave data or analysis data thereof associated with an unknown condition for testing from the object and applying the data to the pain determination means. In such a case, from a measurement value such as brainwave data or analysis data thereof associated with an unknown condition of an object actually measured based on a determination instrument or threshold value, a numerical value corresponding to the threshold value or determination instrument thereof can be calculated to determine the presence/absence of pain and distinction of type and level thereof in comparison with the determination instrument or threshold value.

A step of obtaining brainwave data (e.g., amplitude data) of the object obtains brainwave data for an unknown condition of an object from an object on which measurement is intended, regardless of whether some type of simulation or treatment is applied. Any methodology can be used as long as it is a methodology that can obtain brainwave data. The same methodology as the step of obtaining brainwave data used in the present invention can be used. Generally, the same methodology is used. In addition, this is applied to a pain determination instrument or determination value to determine pain of the object. A predetermined pain determination means or value is referred to as a "pain determination instrument" or "no pain determination prediction instrument" in association with the level differentiated/estimated for an object. It is determined or predicted that there is pain (or specific type of pain) with a numerical value toward the strong pain side than the threshold value and determined or predicted that there is no pain (or specific type of pain) with a numerical value on the weak side.

In one embodiment, the brainwave data or analysis data thereof comprises, as data recording positions, frontal-parietal portions such as F3, F4, C3, C4, P3, and P4 in compliance with the international 10-20 system or expanded standard thereof, and positions on the scalp over the occipital portion as electrode positions. Alternatively, a position at a specific uniform distance (e.g., 2.5 cm or the like) can be covered or recorded. The brainwave data or analysis data thereof comprises at least one brainwave feature selected form these combinations.

In still another embodiment, the brainwave feature comprises at least one selected from the group consisting of Fp1, Fp2, Fpz, F3, F4, Fz, C3, C4, Cz, P3, P4, and Pz, such as mean amplitudes Fz, C3, and C4, and frequencies Fz (α), Fz(β), Cz(δ), C3(θ), and C4(β). It is preferable that the feature comprises, but not limited to, Cz (amplitude), C3(α), Cz(β), Fz(δ), and Cz(γ).

Figure 28:
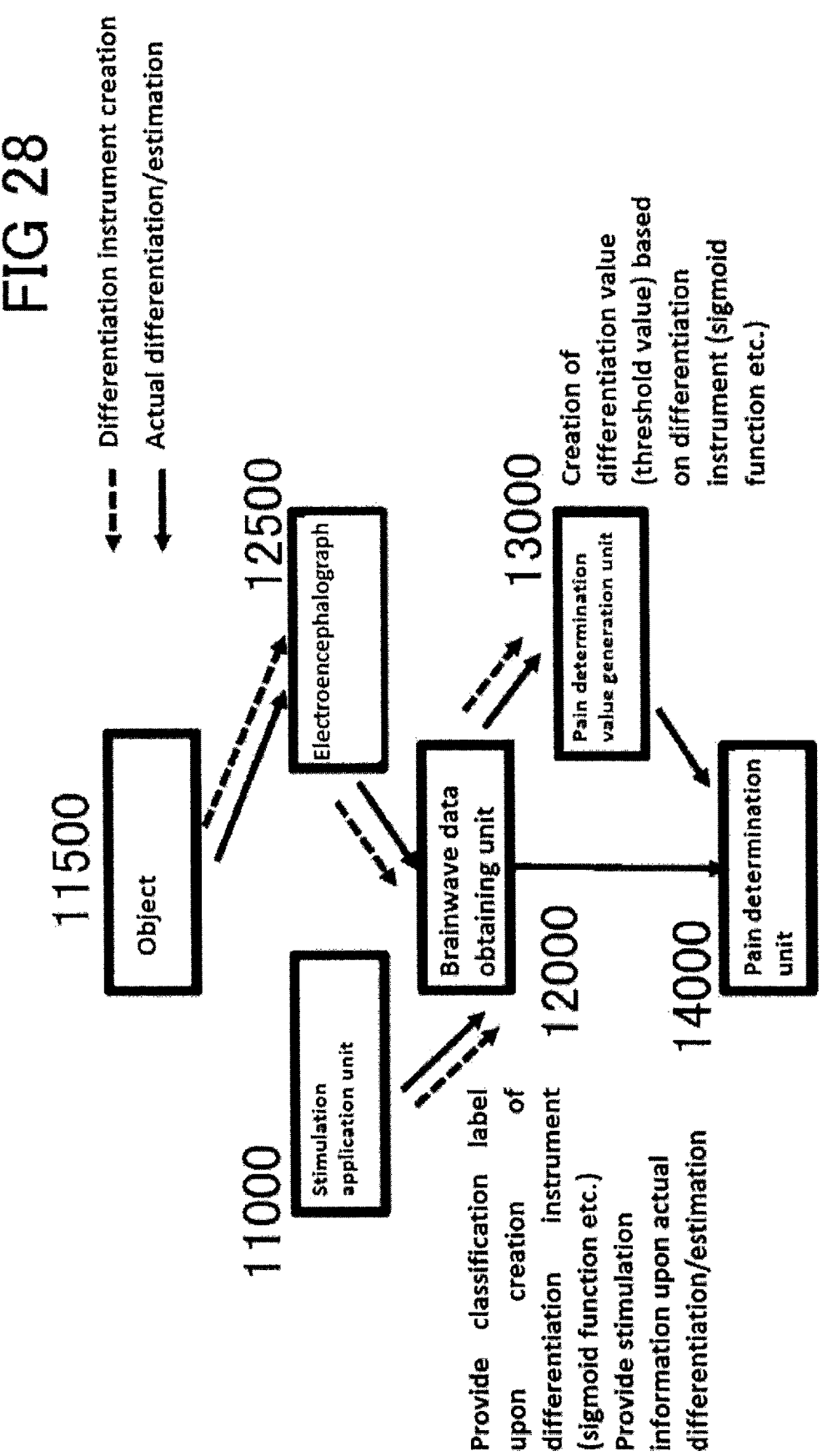
FIG. 28 is an example of a block diagram showing the function configuration of the invention.

FIG. 28 describes a schematic diagram of the apparatus of the invention. This embodiment is for generation of a pain determination instrument (means) therein involving 11000 to 13000. A stimulation application unit 11000 corresponds to A), where information related to environment for applying stimulation or stimulation type is communicated to a brainwave data obtaining unit 12000 and a pain determination value generation unit 13000. The brainwave data obtaining unit 12000 is configured to comprise or to be connected to an electroencephalograph that is or can be connected to an object (11500), so that brainwave data synchronized with stimulation emitted from a stimulation application unit to the object (11500) is obtained (12500).

Figure 29:
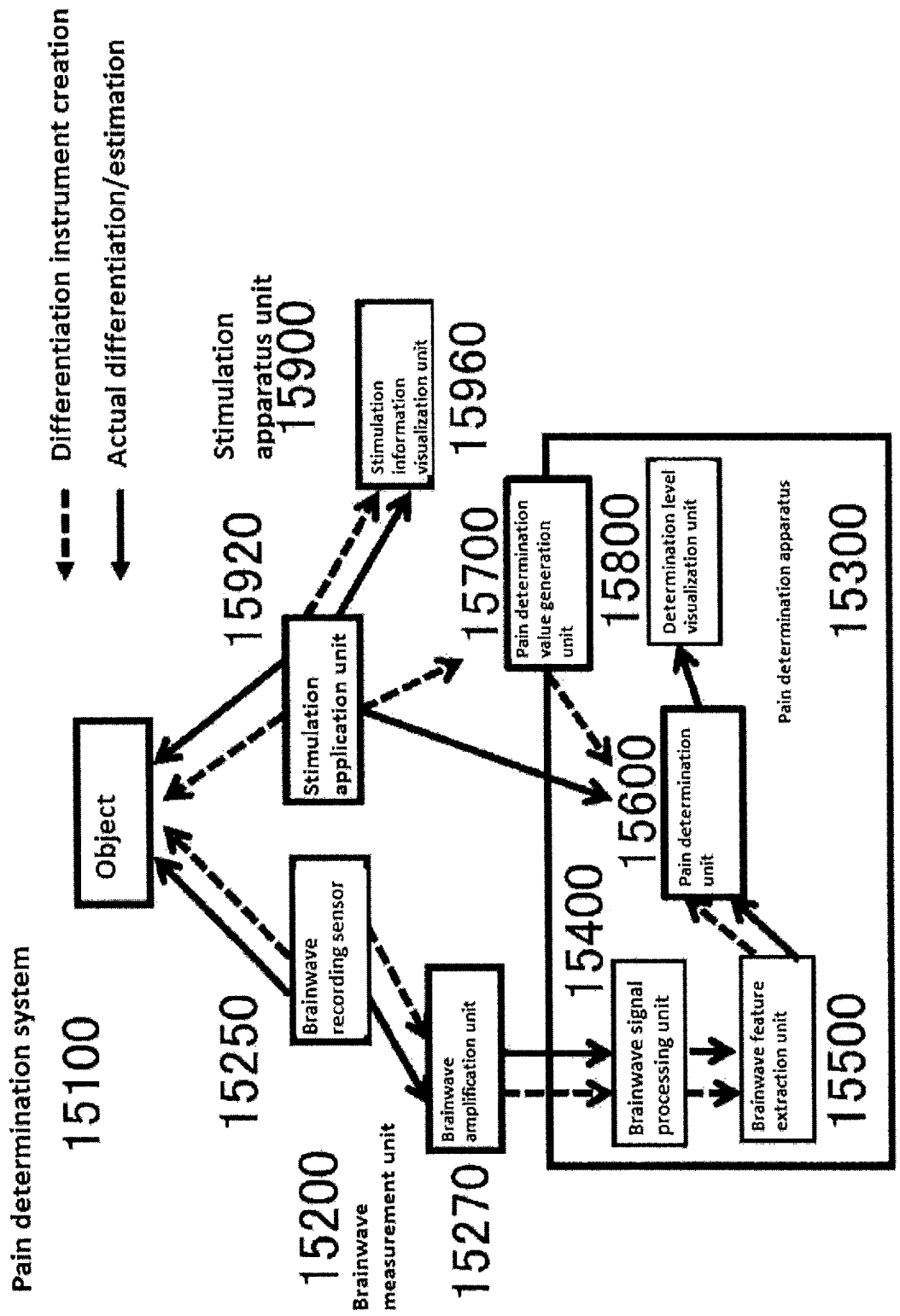
FIG. 29 is an example of a block diagram showing the function configuration of the invention.

FIG. 29 is a block diagram showing functional configurations of a pain determination system 15100 of one embodiment (it should be noted that some of the configuration diagrams are optional constituents that can be omitted). The system 15100 comprises a brainwave measurement unit 15200, which internally comprises or externally connects to a brainwave recording sensor 15250 and optionally a brainwave amplification unit 15270. Signal processing and differentiation/estimation of pain is performed at a pain determination apparatus 15300. In the pain determination apparatus 15300, brainwave signals are processed at a brainwave signal processing unit 15400 (and a brainwave feature is extracted at a brainwave feature extraction unit 15500 as needed), pain, pain level or type, or the like is differentiated/estimated at a pain determination unit 15600, and the degree of unpleasantness is (optionally) made visible at a determination level visualization unit 15800. The system also comprises a stimulation apparatus unit 15900 internally or externally. The stimulation apparatus unit 15900 transmits stimulation information (stimulation type, environment information, or the like) for differentiating actual unknown pain levels and generating a pain differentiation instrument and pain of an object. The stimulation apparatus unit 15900 comprises a stimulation application unit 15920 and optionally a stimulation information visualization unit 15960 to display information such as an image or number associated with stimulation or environment. The pain determination system can also comprise a generation unit 15700 for generating a differentiation instrument or a differentiation value externally or internally to the apparatus 15300.

Such a pain determination system 15100 comprises the brainwave measurement unit 15200 and the pain determination apparatus 15300, and optionally the stimulation apparatus unit 15900. The pain determination apparatus 15300 is materialized, for example, by a computer comprising a processor and a memory. In such a case, the pain determination apparatus 15300 makes a processor function optionally as the brainwave amplification unit 15270, brainwave signal processing unit 15400, (optionally) pain determination unit 15600, (optionally) differentiation level visualization unit 15800, and the like when a program stored in the memory is executed by the processor. The stimulation or environmental information is also made visible as needed. The system 15100 or pain determination apparatus 15300 of the invention can be materialized for example, with a dedicated electrical circuit. A dedicated electrical circuit can be a single integrated circuit or a plurality of electrical circuits. A brainwave data obtaining unit and pain classifier generation unit can have the same configuration as the pain estimation apparatus.

The measurement unit 15200 obtains a plurality of brainwave data by measuring a brainwave from an object being estimated via an electroencephalograph (brainwave recording sensor 15250). The object being estimated is an organism in which a change in brainwave is induced by stimulation or environment, which is not limited to humans.

The pain determination unit 15600 differentiates/estimates pain using a determination value. A differentiation instrument or differentiation value is also generated when not generated externally or internally in advance. A part generating a differentiation instrument or differentiation value can be comprised externally or internally to the apparatus 15300 as the pain determination value generation unit 15700. A pain determination value is for estimating or classifying pain from amplitudes of a plurality of brainwave data. Specifically, the pain determination unit 15600 or the pain determination value generation unit 15700 can generate a determination value for estimating or classifying pain of an object from brainwave data.

The brainwave recording sensor 15250 measures electrical activity generated in the brain of an object being estimated with an electrode on the scalp. The brainwave recording sensor 15250 then outputs the result of measurement, brainwave data. Brainwave data can be amplified as needed.

This is further explained based on FIG. 28. The aspect comprising a determination unit is described. FIG. 28 references the brainwave data obtaining unit 12000 in addition to the pain determination unit 14000. The dotted lines indicate the procedure for creating a differentiation model, and the solid lines indicate the procedure for differentiating/estimating an actual pain level. In this case, as described in the section of (Generation of pain determination value), brainwave data can be obtained via an electroencephalograph from the object 11500. Specifically, the brainwave data obtaining unit 12000 is configured to be connectable to the object 11500, and the brainwave data obtaining unit 12000 is configured to comprise or to be connected to an electroencephalograph that is or can be connected to the object (11500), so that brainwave data obtained from the object (11500) can be obtained (12500). The pain determination unit 14000 is configured to store a pain determination value in advance or receive data generated separately, and optionally configured to be capable of referencing. Such a connection configuration can be wired or wireless connection. A pain determination value stored in advance is generated based on, for example, a differentiation instrument of a feature (sigmoid fitting or the like) in the pain determination value generation unit 13000.

FIG. 29 is a block diagram showing the functional configurations of the pain determination system 15100 in one embodiment. The system 15100 comprises the brainwave measurement unit 15200, which internally comprises or externally connects to the brainwave recording sensor 15250 and optionally the brainwave amplification unit 15270. Signal processing and differentiation/estimation of pain are performed at the pain determination apparatus 15300. In the pain determination apparatus 15300, brainwave signals are processed at the brainwave signal processing unit 15400, pain is (optionally) differentiated/estimated at the pain determination unit 15600, and pain is (optionally) made visible at the differentiation level visualization unit 15800. The system also comprises the stimulation apparatus unit 15900 internally or externally. The stimulation apparatus unit 15900 contributes to the creation of a pain differentiation instrument of an object. A differentiation value can be created in advance at the pain determination value generation unit 15700.

In this manner, the pain determination system 15100 comprises the brainwave measurement unit 15200 and the pain determination apparatus 15300. The pain determination apparatus 15300 is materialized, for example, by a computer comprising a processor and a memory. In such a case, the pain determination apparatus 15300 makes a processor function optionally as the brainwave amplification unit 15270, brainwave signal processing unit 15400, (optionally) pain determination unit 15600, (optionally) differentiation level visualization unit 15800, and the like when a program stored in the memory is executed by the processor. Reference stimulation is also made visible and vocalized as needed. The system 15100 or apparatus 15300 of the invention can be materialized, for example, with a dedicated electrical circuit. A dedicated electrical circuit can be a single integrated circuit or a plurality of electrical circuits. A brainwave data obtaining unit and pain determination value generation unit 13000 (see FIG. 28) can have the same configuration as the pain estimation apparatus or can be configured as an external unit.

The brainwave measurement unit 15200 obtains a plurality of brainwave data by measuring a brainwave a plurality of times from an object being estimated via an electroencephalograph (brainwave recording sensor 15250). The object being estimated is an organism in which a change in brainwave is induced by pain, which is not limited to humans.

The pain determination unit 15600 estimates or classifies the magnitude of pain from amplitudes of a plurality of brainwave data based on a pain classifier created by the pain determination value generation unit 13000 (see FIG. 28). Specifically, the pain determination unit 15600 estimates or classifies pain of an object from brainwave data based on a determination value.

The brainwave recording sensor 15250 measures electrical activity generated in the brain of an object being estimated with an electrode on the scalp. The brainwave recording sensor 15250 then outputs the result of measurement, brainwave data. Brainwave data can be amplified as needed.

Next, the process or method of an apparatus configured in the above manner is described. FIG. 27 is a flowchart showing a series of processing. In this aspect, S10100 to S10400 are involved.

A pain determination value, after creation, can be stored in the pain determination unit 14000 in advance (FIG. 28), or the pain determination unit 14000 can be configured to be able to receive value data. Alternatively, if the pain determination value generation unit 13000 is installed, the value can be stored in the generation unit. A recording medium can be provided separately. This value can be received through communication.

Next, brainwave data is obtained from an object (S10200) (see FIG. 27). The brainwave data can be obtained using the same technology as the reference data or the like. While the same embodiment can be employed, the same apparatus or device does not always need to be used, which can be the same or different.

Next, brainwave data (e.g., amplitude data) obtained in S10200 is fitted to a pain determination value, and pain corresponding to the brainwave data is differentiated/estimated (S10300) (see FIG. 27). Such pain determination can be configured so that a certain phrase (comfortable pain, unpleasant pain, or the like) is displayed or vocalized when a predetermined value is outputted, and an actual value and a pain determination value are displayed in juxtaposition to allow a user (clinician) to review the values.

Figure 30:
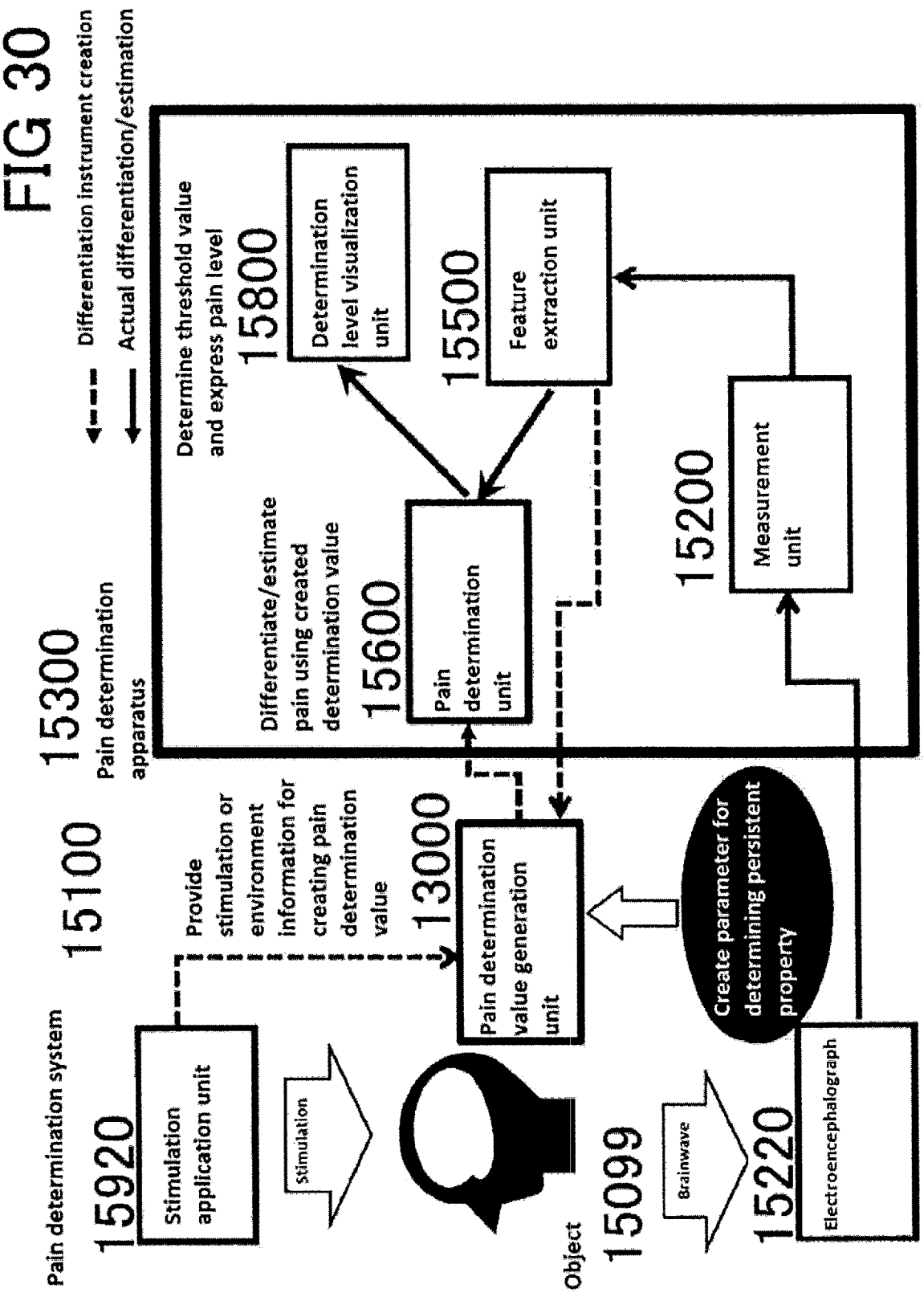
FIG. 30 is another example of a block diagram showing the function configuration of the invention.

FIG. 30 is a diagram of the pain determination system 15100 describing the details of the operation, extending the block diagram of FIG. 29 to include the process of generating a differentiation instrument (e.g., determination of a differentiation value by sigmoid function fitting). The system 15100 comprises the brainwave measurement unit 15200, connected to the electroencephalograph 15220, and obtains a brainwave feature such as a mean value at the feature extraction unit 15500 from the collected brainwave data as needed. When a pain determination value is generated in advance, a pain determination value is generated by a differentiation instrument, e.g., generation of a parameter for determining a persistent property or a sigmoid function fitting, at the pain determination value generation unit 13000 external or internal to the pain determination apparatus 15300. The pain determination value is transmitted to and stored in the pain determination unit 15600. In determining pain of actual unknown stimulation type or environment, brainwave data synchronized with the application or display of stimulation at the stimulation application unit 15920 is transmitted from the electroencephalograph 15220 to the measurement unit 15200, then a brainwave feature is created at the feature extraction unit 15500 and transmitted to the pain determination unit 15600, and pain of unknown stimulation or environment is differentiated/estimated using the pain determination value. Pain is (optionally) made visible at the differentiation level visualization unit 15800. Such a series of processes can be materialized by a computer or mobile terminal comprising a processor and a memory, or a dedicated electrical circuit. A dedicated electrical circuit can be a single integrated circuit or a plurality of electrical circuits. The processes can be materialized by a software or by controlling a required hardware.

Other Embodiments

The pain estimation apparatus according to one or more embodiments of the invention has been described based on the embodiments, but the present invention is not limited to such embodiments. Various modifications applied to the present embodiments and embodiments constructed by combining constituent elements in different embodiments that are conceivable to those skilled in the art are also encompassed within the scope of one or more embodiments of the invention, as long as such embodiments do not deviate from the intent of the inventions.

For example, a peak to peak value can be used as the amplitude value of brainwave data in each of the embodiments described above, but the amplitude value is not limited thereto. For example, a simple peak value can be used as the amplitude value.

In accordance with the embodiment described above, the range of the value of magnitude of pain can be envisioned to be set so that the value of Pmax, which is the magnitude of pain corresponding to the upper limit value Amax of a brainwave amplitude, would be 1, or the value of Pmin, which is the magnitude of pain corresponding to the lower limit value Amin of the brainwave amplitude, would be 0 and display determination values at the visualization unit 15800, but the range of values is not limited thereto. For example, the magnitude of pain can be represented by 0 to 100. In such a case, the pain determination unit 5600 can estimate the value Px of magnitude of pain by the following equation.

$$Px = Pmax \times (Ax - Amin)/(Amax - Amin)$$

Curve fitting was described above as an example of generating a determination value of unpleasant pain by analyzing a plurality of brainwave data, but this is not a limiting example. For removing external or biological artifacts in the process of calculating an event related brainwave feature associated with instantaneous pain, a predetermined value can also be used as the upper limit value of a brainwave amplitude. The predetermined values that are excluded is for example 50 μV to 100 μV, which can be experimentally or empirically determined. In such normal analysis, data from about plus or minus 50 μV to 100 μV is eliminated as an artifact removal method. Such artifact removal can also be performed in the present invention as needed.

If the magnitude of pain felt by an object 15099 changes depending on the stimulation type or application environment, stimulation applied to an object 15099 by the stimulation application unit 15920 (see FIG. 30) can be any type of stimulation. However, a testing paradigm (pain oddball paradigm) that applies reference stimulation which is the standard and background stimulation and strong pain or unpleasant pain stimulation at, for example, a ratio of 7 to 3 is used to extract a brainwave feature of instantaneous pain in the invention.

Some or all of the constituent elements of the pain determination apparatus in each of the embodiments described above can be comprised of a single system LSI (Large Scale Integration). For example, as shown in FIG. 30, the pain determination apparatus 15300 can be comprised of a system LSI having optionally the measurement unit 15200 and optionally the stimulation application unit 15920.

System LSI is ultra-multifunctional LSI manufactured by integrating a plurality of constituents on a single chip, or specifically a computer system comprised of a microprocessor, ROM (Read Only Memory), RAM (Random Access Memory) and the like. A computer program is stored in a ROM. The system LSI accomplishes its function by the microprocessor operating in accordance with the computer program.

The term system LSI is used herein, but the term IC, LSI, super LSI, and ultra LSI can also be used depending on the difference in the degree of integration. The methodology for forming an integrated circuit is not limited to LSI. An integrated circuit can be materialized with a dedicated circuit or universal processor. After the manufacture of LSI, a programmable FPGA (Field Programmable Gate Array) or reconfigurable processor which allows reconfiguration of the connection or setting of circuit cells inside the LSI can be utilized.

If a technology of integrated circuits that replaces LSI by advances in semiconductor technologies or other derivative technologies becomes available, functional blocks can obviously be integrated using such technologies. Application of biotechnology or the like is also a possibility.

One embodiment of the invention can be not only such a pain determination value generation, pain determination apparatus, but also a pain classifier generation, pain differentiation/classification method using characteristic constituent units contained in a pain estimation apparatus as steps. Further, one embodiment of the invention can be a computer program for making a computer execute each characteristic step in pain determination value generation, pain determination methods. One embodiment of the invention can also be a computer readable non-transient recording medium on which such a computer program is recorded.

In each of the embodiments described above, each constituent element can be materialized by being configured with a dedicated hardware or by executing software program that is suited to each constituent element. Each constituent element can be materialized by a program execution unit such as a CPU or a processor reading out and executing a software program recorded on a recording medium such as a hard disk or semiconductor memory. In this regard, software materializing the pain estimation apparatus of each of the embodiments described above or the like can be a program such as those described above herein.

Thus, the present invention provides a program for making a computer execute a method of differentiating or evaluating pain, the method comprising comparing brainwave data or analysis data thereof from some or all of a period between the earliest point among evoked brainwave potential, early event related potential, and 250 msec and 2000 msec from application of target stimulation with brainwave or analysis data thereof after the same time from application of reference stimulation.

In another aspect, the present invention provides a recording medium for storing a program for making a computer execute a method of differentiating or evaluating pain, the method comprising comparing brainwave data or analysis data thereof from some or all of a period between the earliest point among evoked brainwave potential, early event related potential, and 250 msec and 2000 msec from application of target stimulation with brainwave or analysis data thereof after the same time from application of reference stimulation.

In another aspect, the present invention provides a system for differentiating or evaluating pain, comprising: a brainwave data input unit for inputting brainwave data or analysis data thereof; and an analysis unit for comparing brainwave data or analysis data thereof from some or all of a period between the earliest point among evoked brainwave potential, early event related potential, and 250 msec and 2000 msec from application of target stimulation with brainwave or analysis data thereof after the same time from application of reference stimulation. The system can function as a medical apparatus or a part thereof.

(Note)

As used herein, "or" is used when "at least one or more" of the listed matters in the sentence can be employed. When explicitly described herein as "within the range of two values", the range also includes the two values themselves.

Reference literatures such as scientific literatures, patents, and patent applications cited herein are incorporated herein by reference to the same extent that the entirety of each document is specifically described.

As described above, the present invention has been described while showing preferred embodiments to facilitate understanding. The present invention is described hereinafter based on Examples. The above descriptions and the following Examples are not provided to limit the present invention, but for the sole purpose of exemplification. Thus, the scope of the present invention is not limited to the embodiments or the Examples specifically described herein and is limited only by the scope of claims.

EXAMPLES

Examples are described hereinafter. The objects used in the following Examples were handled, as needed, in compliance with the standards set forth by the Osaka University, and the Declaration of Helsinki and ICH-GCP in relation to clinical studies.

Example 1: Sparse Model Analysis with Thermal Pain Stimulation

This Example conducted sparse model analysis on data from a thermal pain stimulation experiment.
(Participants)
40 healthy adult subjects in their 20s to 70s participated in this experiment. Informed consent was obtained from the participants prior to the experiment. All participants self-reported as having no history of a neurological and/or psychiatric illness, or acute and/or chronic pain under clinical drug therapy conditions. This study was in compliance with the Declaration of Helsinki and conducted under approval of the Osaka University Graduate School ethics committee.
(Procedure)

The inventors used a thermal stimulation application paradigm. This paradigm used thermal stimulation, which was increased by 2° C. from level 1 at 40° C. to level 6 at 50° C., with a baseline temperature of 35° C. A trial block at each stimulation level consisted of three stimulations. Each stimulation had had a plateau lasting 5 seconds, and a waiting period for increase and decrease of about 5 seconds. There was a 5 second interval between stimulations. The rest between blocks was fixed at 100 seconds. The participants wore a thermal stimulation probe on the inside left forearm, and received thermal stimulation while lying down on an armchair. The participants continuously evaluated pain intensities in the range of 0 to 100 (0: "no pain"; 100: "unbearable pain") on a computerized visual analog scale (COVAS). COVAS data was simultaneously recorded with changes in stimulation intensities.
(EEG Data Record)

Intervals between blocks for rest were fixed to 100 seconds. In both paradigms, commercially available Bio-Amplifier (EEG 1200: Nihon Koden) was used to record EEG from five scalp Ag/AgCl scalp electrodes (Fp1, Fz, Cz, C3, and C4). The front-most electrode Fp1 was used for recording EOG activity. Reference electrodes were attached to both earlobes, and an outside electrode was placed on the center of the forehead. The sampling rate was 1000 Hz and amplified using a band pass filter in the range of 0.3 to 120 Hz. The impedance of all electrodes was less than 15 kU.
(EEG Analysis)

Four electrodes on the scalp (Fz, Cz, C3, and C4) were subjected to brainwave analysis. The Fp1 forehead electrode was used for processing eye movement. From the brainwave data, EOG was removed from an analysis electrode using the following regression filter before sampling for each condition. Since Fp1 data is the closest to the left eye and heavily affected by eye movement, Fp1 data was used as EOG data.

$$\text{Raw EEG} = \beta \times \text{EOG} + C$$

$$\text{EEG estimate} = \text{raw EEG} - \beta \times \text{EOG}$$

$\beta$: partial regression coefficient
$C$: intercept
EEG estimate: estimated EEG After VEOG was diminished, a 60 Hz notch filter was applied to eliminate external electrical noise. Any time frame with potential exceeding 100 µV was excluded from the data. Brainwave data was then sampled from 5 seconds before applying each stimulation to 15 seconds after application of stimulation (18 epochs), and baseline correction was performed using potential before application of stimulation. After the baseline correction, amplitudes were converted to absolute values, and potential was standardized using the maximum value of all stimulation under all conditions for each electrode. Finally, a mean amplitude for 15 seconds after application of stimulation was calculated, and mean potential of levels 1 and 2 was extracted as features of weak pain levels and mean potential of levels 5 and 6 was extracted as features of strong pain levels.

(Frequency Analysis)

Four electrodes on the scalp (Fz, Cz, C3, and C4) were subjected to brainwave analysis. First, a 60 Hz notch filter was applied to reduce external electrical noise. Brainwave data was sampled for 15 seconds after application of stimulation (18 epochs), subjected to Fourier transform and then the frequency power (log value of real number portion) was calculated in δ (1 to 3 Hz), θ (4 to 7 Hz), α (8 to 13 Hz), β (14 to 30 Hz), and γ (31 to 100 Hz).

Frequency power=log(abs(FFT)) [Numeral 6]

log: log 10
abs: absolute value
FFT: Fourier transform data for each band

The value was standardized using the maximum value of frequency power for all stimulation under all conditions for each electrode. Frequency power of levels 1 and 2 was extracted as features of weak pain levels and frequency power of levels 5 and 6 was extracted as features of strong pain levels. With these EEG and frequency analysis, a total of 24 features used in modeling were obtained at Fz, Cz, C3, and C4.

(Sparse Model Analysis Distinguishing Strong and Weak Thermal Pain Stimulation)

24 features (4 time-domain data, 20 frequency domain data) and labels for two levels of thermal pain stimulation (1="weak"; 2="strong"; n=160) were used by the inventors to perform sparse model analysis (multiple regression analysis) using a LASSO algorithm. As shown in FIG. 4, data was divided into model creation data and test data at a ratio of 8:2. 10-fold cross validation was performed using the model data, and the optimal λ was calculated to determine the feature coefficient (partial regression coefficient) and intercept of the regression equation. After determining the λ value, partial regression coefficient, and intercept, an estimation value of a pain level was calculated using a feature of the test data. An estimation value equal to or less than 50% of the whole was determined as "1", i.e., "weak pain", and an estimation value greater than 50% of the whole was determined as "2" (strong pain). The estimation value was collated with actual pain labels to find the differentiation accuracy. A process for randomly selecting learning and test data was run 1000 times to calculate the distribution and mean value of the differentiation accuracy and feature coefficients. Further, the label of the test data was randomly switched to calculate the chance level of differentiation accuracy for comparison with actual differentiation accuracy.

(Results)

Figure 5:
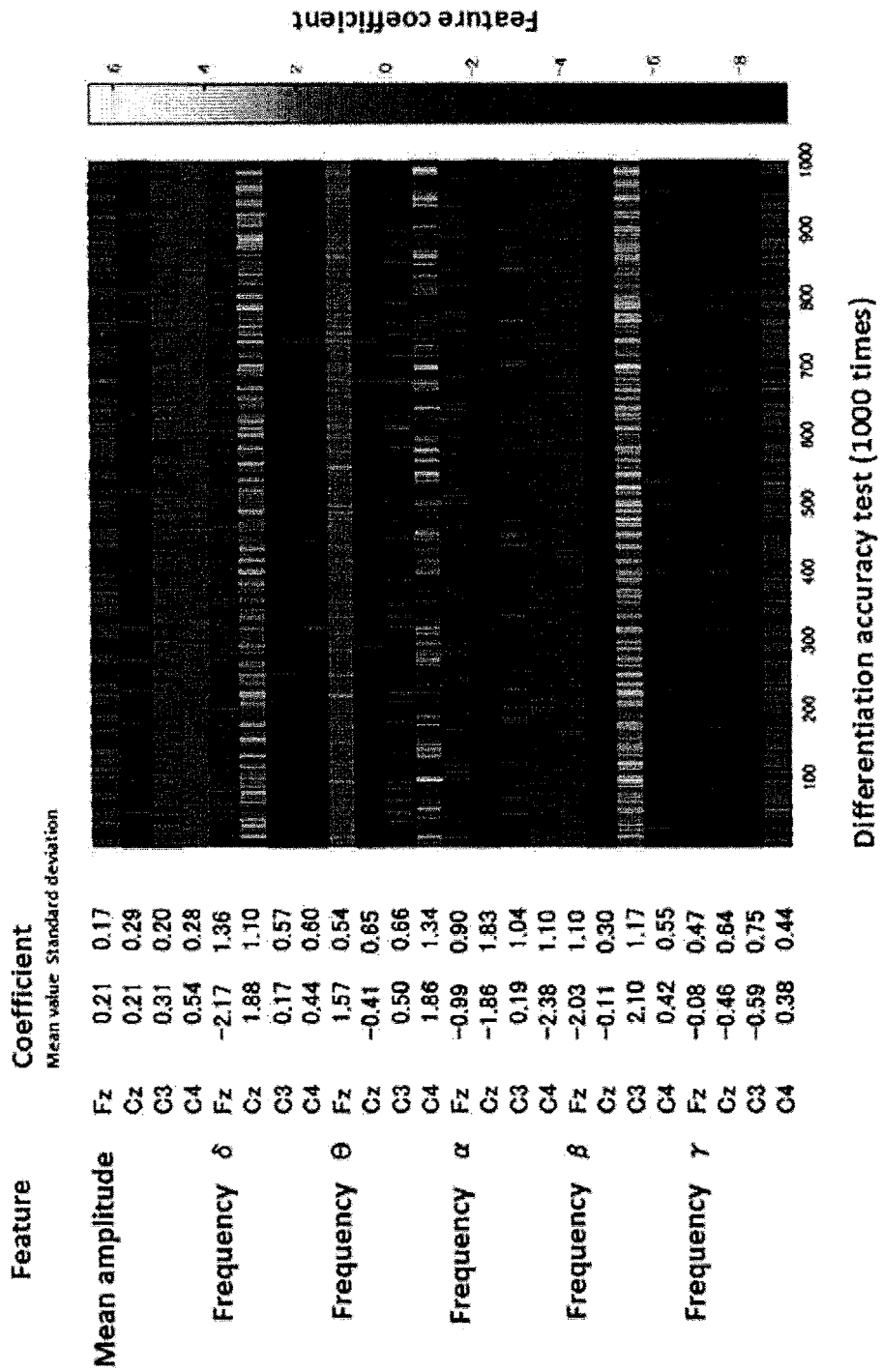
FIG. 5 shows a thermogram of the feature coefficients in Example 1. Differentiation test was run 1000 times (X axis). A total of 24 features included mean amplitude absolute values (4 features) and frequency power (20 features). In 1000 differentiation accuracy tests, the mean value of coefficients of features with high contribution was consistently high. For example, the coefficient in the region of change of the 5 band of the frontal portion exhibits a numerical value of "−2.17".
Figure 6:
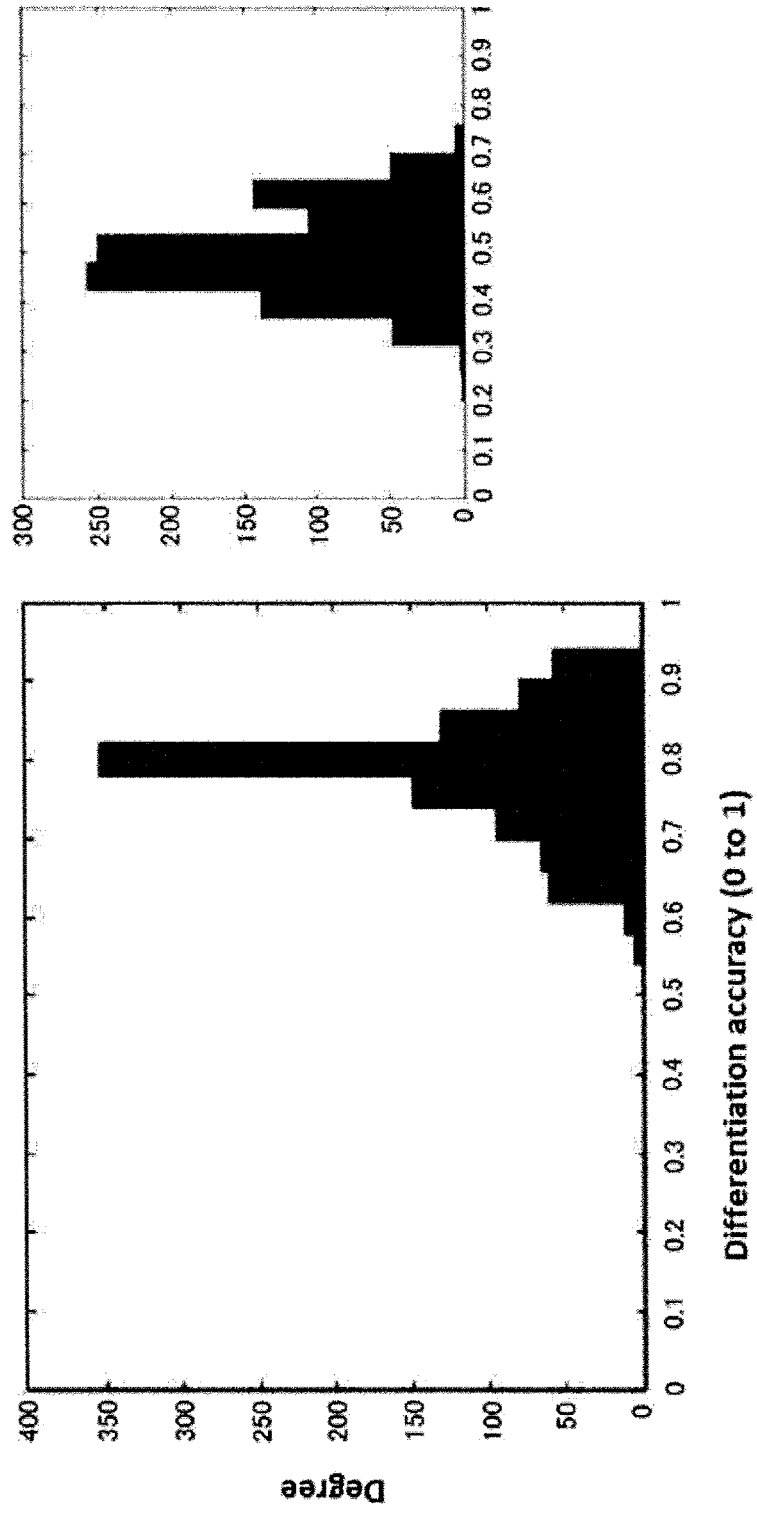
FIG. 6 shows a distribution of differentiation accuracy of test data in Example 1. The mean differentiation accuracy of 1000 tests was about 80%, exhibiting a numerical value that is about 30% higher compared to the mean differentiation accuracy when differentiation accuracy is estimated by randomizing the labels (strong/weak) of pain levels.

FIG. 5 shows the change in partial regression coefficients of features used in a regression equation in 1000 differentiation accuracy tests, and the mean value and standard deviation of the coefficients. Features with high contribution were frequency features such as α power at C4 (−2.38), δ power at Fz (−2.17), β power at C3 (2.10), β power at Fz (−2.03), δ power at Cz (1.88), θ power at C4 (1.86), α power at Cz (−1.86), and θ power at Fz (1.57). As shown in FIG. 6, 1000 differentiation accuracy was distributed in the range from 80% to less than 90% about 350 times, which was greater than 30% of the whole. The mean differentiation accuracy was 78.2±7.6%, which was about 30% higher compared to the differentiation accuracy at the chance level when the pain labels of test data were randomized (50±8.7%).

(Example 2: Use in Pre-Generated Regression Model (Differentiation Model))

In this Example, an example of an actual pain level differentiation apparatus is shown.

In actual practice, it is desirable to link or accessibly connect a differentiation model generation unit to a pain differentiation/estimation apparatus, as shown in FIG. 16. Such a pain differentiation/estimation apparatus is provided by utilizing the differentiation model from sparse modeling obtained in the present invention.

A method of differentiating/estimating a pain level of an unknown object being estimated using a pain differentiation/estimation model generated in advance in accordance with Example 1 is shown. A differentiation model that has been created in advance in this manner is stored or accessibly made available to a pain differentiation/estimation unit. While the subjects and data analysis method were the same as Example 1, model creation data was created by randomly excluding one object (four samples), and the excluded one object was inputted into the differentiation/estimation model as the unknown object being estimated.

(Results)

Figure 7:
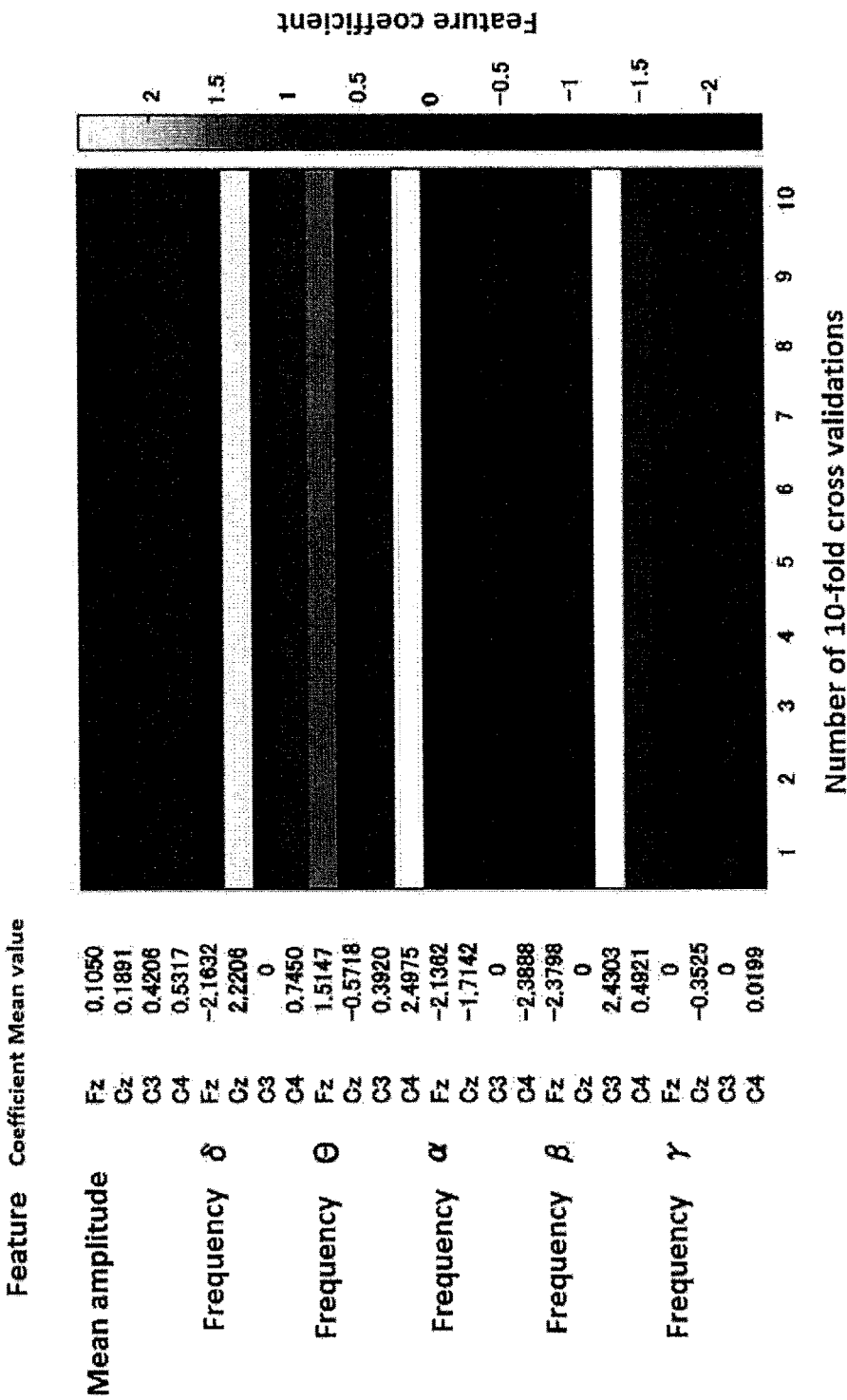
FIG. 7 shows a thermograph of feature coefficients upon differentiation model creation in Example 2. Feature coefficients used in a differentiation model were calculated by 10-fold cross validation using 156 sample data while randomly excluding data for 1 subject (4 samples) from data for 40 subjects.
Figure 8:
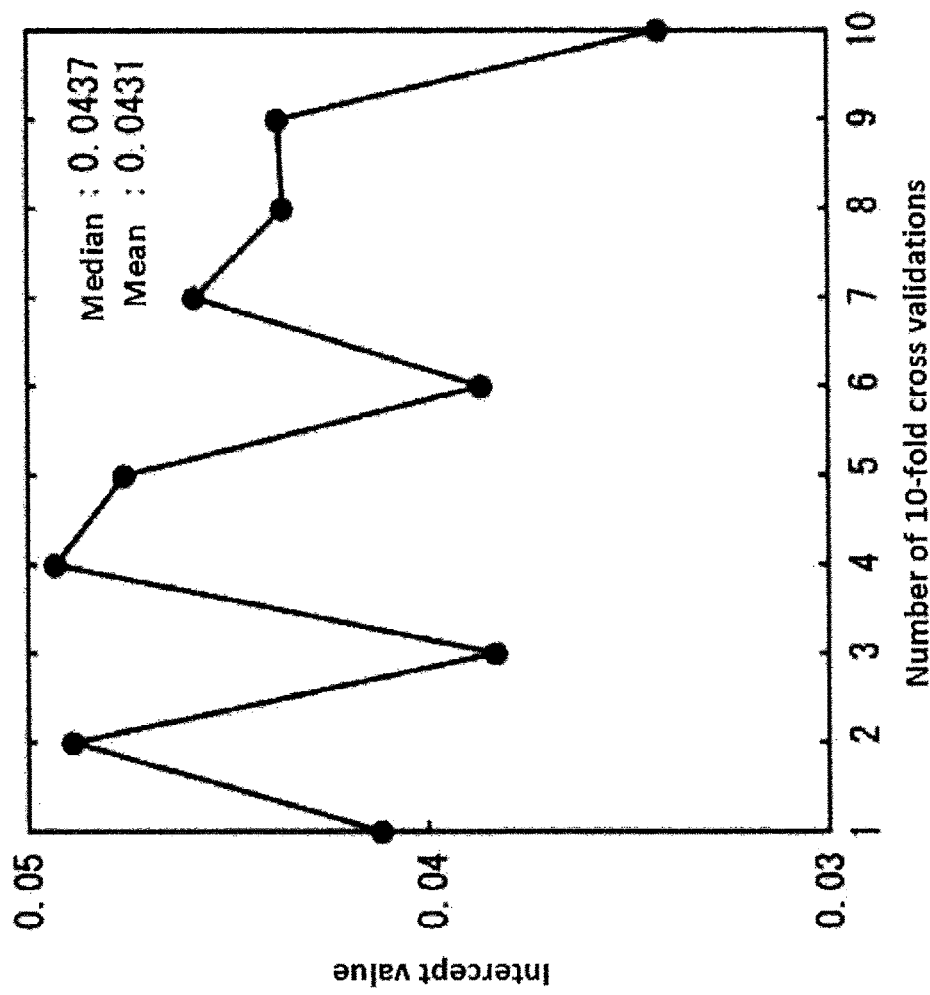
FIG. 8 shows a change in the value of intercept in 10-fold cross validation upon differentiation model creation in Example 2.
Figure 9:
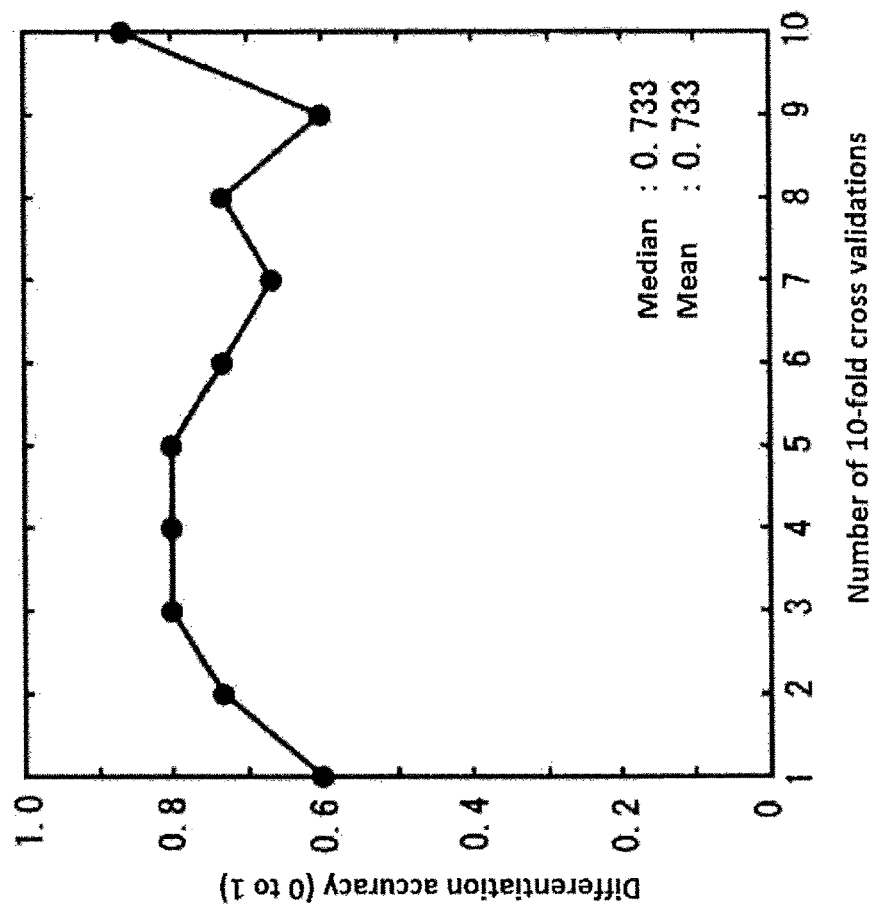
FIG. 9 shows the change in differentiation accuracy in 10-fold cross validation upon differentiation model creation in Example 2.

As shown in FIG. 7, features such as δ power at C4 (2.50), β power at C3 (2.43), α power at C4 (2.39), β power at Fz (−2.38), δ power at Cz (2.22), δ power at Fz (−2.16), α power at Fz (−2.13), and θ power at Fz (1.51) had high contribute in a model according to sparse model analysis for differentiation model creation. As shown in FIG. 8, the intercept as of model creation varied in the range of 0.03 0.05, and the median and mean were both about 0.043. FIG. 9 shows the change in differentiation accuracy in 10-fold cross validation. Accuracy (maximum value of "1") was within the range of 0.6 to 0.9, and the median and mean were both 0.733. The optimal λ was 0.0027 in all cases. From the above results, a pain level differentiation/estimation model such as that in FIG. 10 was created using the mean value of feature coefficients and intercepts. Estimation values equal to or less than 50% were categorized as "weak pain level" and values greater than 50% as "strong pain level" by using a threshold value level of 50% and collated with actual pain levels. FIG. 11 shows the pain level differentiation/estimation equation for one unknown object being estimated who was excluded, and output results. The figure shows that a pain level can be accurately differentiated/estimated from a brain feature with a differentiation/estimation model for this object.

Example 3: Differentiation of Instantaneous Pain

In this Example, instantaneous pain was differentiated using a pain oddball task. High temperature stimulation was used as stimulation for instantaneous pain. After testing brainwaves, the degree of unpleasantness of pain stimulation used was studied by subjective reporting.

(Method)
(Participants)

The same group of 80 healthy adult subjects in their 20s to 70s participated in a pain oddball paradigm experiment using high temperature stimulation. Informed consent was obtained from the participants prior to the experiment. All participants self-reported as having no history of a neurological and/or psychiatric illness, or acute and/or chronic pain under clinical drug therapy conditions. This Example was in compliance with the Declaration of Helsinki and conducted under approval of the Osaka University Hospital ethics committee.

(Experimental Stimulation and Procedure)

Figure 20:
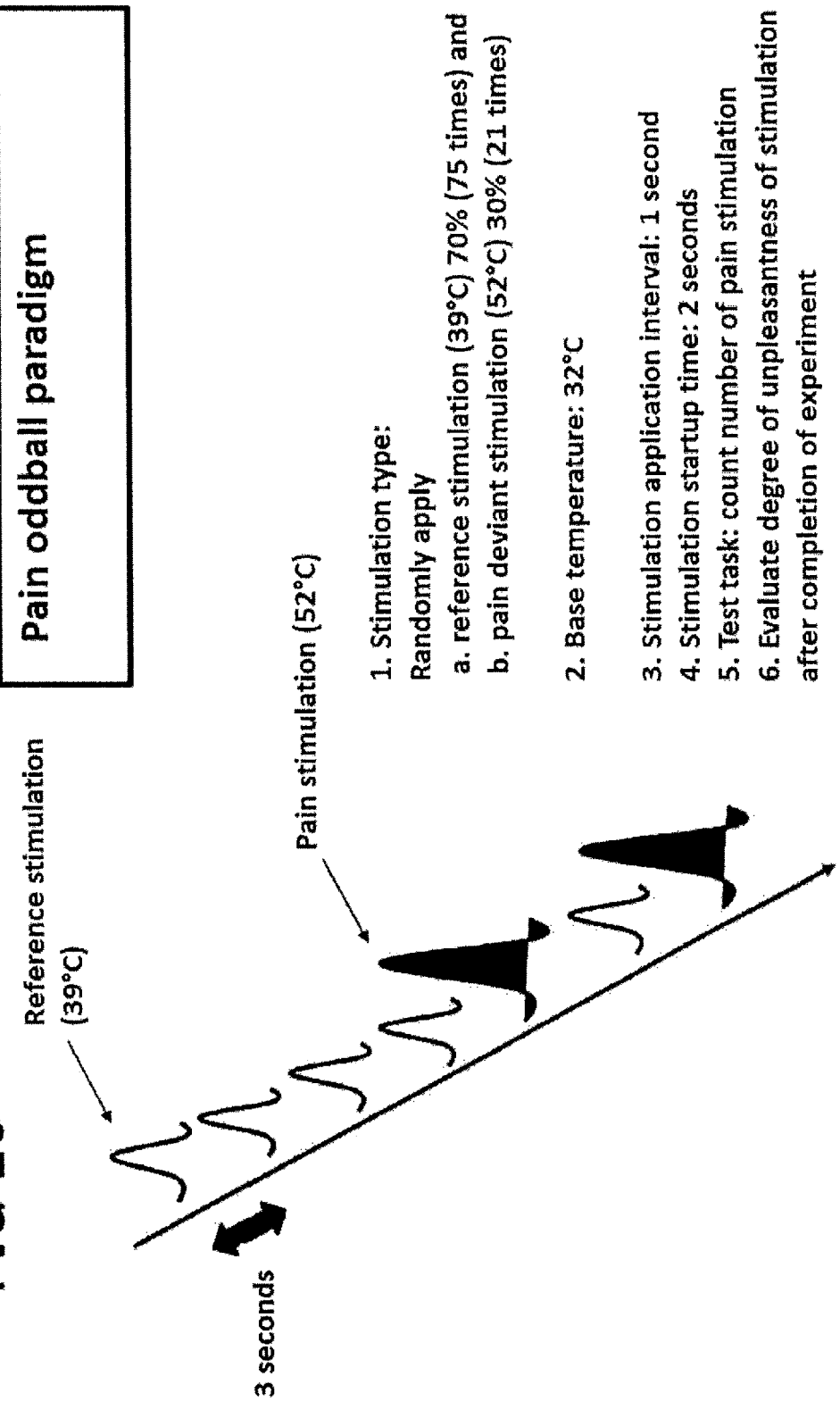
FIG. 20 shows an instantaneous pain experiment method used in the Examples of the invention. The "pain odd ball paradigm" was used in this Example. This paradigm randomly applies reference stimulation (39° C.) at a high frequency=(about 70%) and deviant stimulation (52° C.) for strong pain at a low frequency (about 30%). Brainwaves are simultaneously recorded, and the arithmetic mean waveform of reference stimulation and deviant stimulation is calculated for comparison based on the method shown in FIG. 19.

The outline of the experiment is illustrated in FIG. 20. A temperature stimulation system (Pathway; Medoc Co., Ltd., Ramat Yishai, Israel) was used to apply high temperature stimulation to the right forearm of the participants. Reference stimulation (39° C.: 75 times) and deviant stimulation (52° C.: 21 times) of strong pain were randomly applied while setting the base temperature at 32° C. Reference and deviant stimulation were generated as pulses in two seconds from starting. The interval between stimulations was one second. Subjects silently counted the number of pain stimulation during the test, and reported the number after completion. Additionally, after the completion of the brainwave experiment, a trial in which reference stimulation and deviant stimulation randomly occurs a plurality of times was performed. The unpleasantness was evaluated in the range of 0 to 100 (0: "no pain"; 100: "unbearable pain") on a computerized visual analog scale (COVAS). COVAS data was simultaneously recorded with changes in stimulation intensities.

(EEG Data Collection)

Brainwave data was recorded with a commercially available electroencephalograph from Ag/AgCl7 electrodes on the scalp (Fp1, Fp2, F3, F4, C3, C4, and Pz). The lead electrode was the earlobe. Each of the left and right electrodes was connected to the earlobe electrode on the same side. The frequency band was 0.3 to 120 Hz, and the sampling frequency was 1000 Hz. The impedance was maintained at 15 kΩ or less.

(EEG Analysis)

(Extraction of Feature of Amplitude)

The following regression filter was applied to the continuously recorded EEG data to remove eye movement noise (EGG).

Raw EEG=β×EOG+C [Numeral 1]

EEG estimate=raw EEG−β×EOG

β: regression coefficient
C: intercept
EEG estimate: estimated EEG

As the eye movement data, Fp1 and Fp2 data that are the closest to both eyes were used as EOG data (Fp1+Fp2). After EOG correction, a band pass filter (0.3 to 40 Hz) was applied to remove low and high frequency components. Epoch waveforms from 200 msec before application of stimulation to 2000 msec after application of stimulation were sampled for each stimulation condition. After baseline correction using mean potential before application of stimulation, artifacts were removed at ±50 µV, and arithmetic mean was calculated.

(Subjective Evaluation Analysis)

Subjective evaluation points for the degree of unpleasantness of reference and strong pain stimulation were calculated using a subjective evaluation paradigm. Each conditional stimulation was randomly applied three times. The maximum value was found. from 1 second before the start of the next stimulation to before the start of the next stimulation, and the mean value was found. Since subjective evaluation of pain generally increases or decreases with a delay from application of stimulation, the time setting described above was used to obtain accurate stimulation evaluation.

(Statistical Analysis)

(Persistent Property Analysis)

Reference stimulation and deviant stimulation for strong pain were compared with a t-test using the mean amplitude from 600 msec, where intermediate ERP time frame ends and late time frame starts, to 2000 msec from the overall arithmetic mean waveform of 80 subjects. The means amplitude of 200 to 600 msec was also compared using a t-test between the stimulations for comparison of the effects.

(Results and Discussion)

Figure 21:
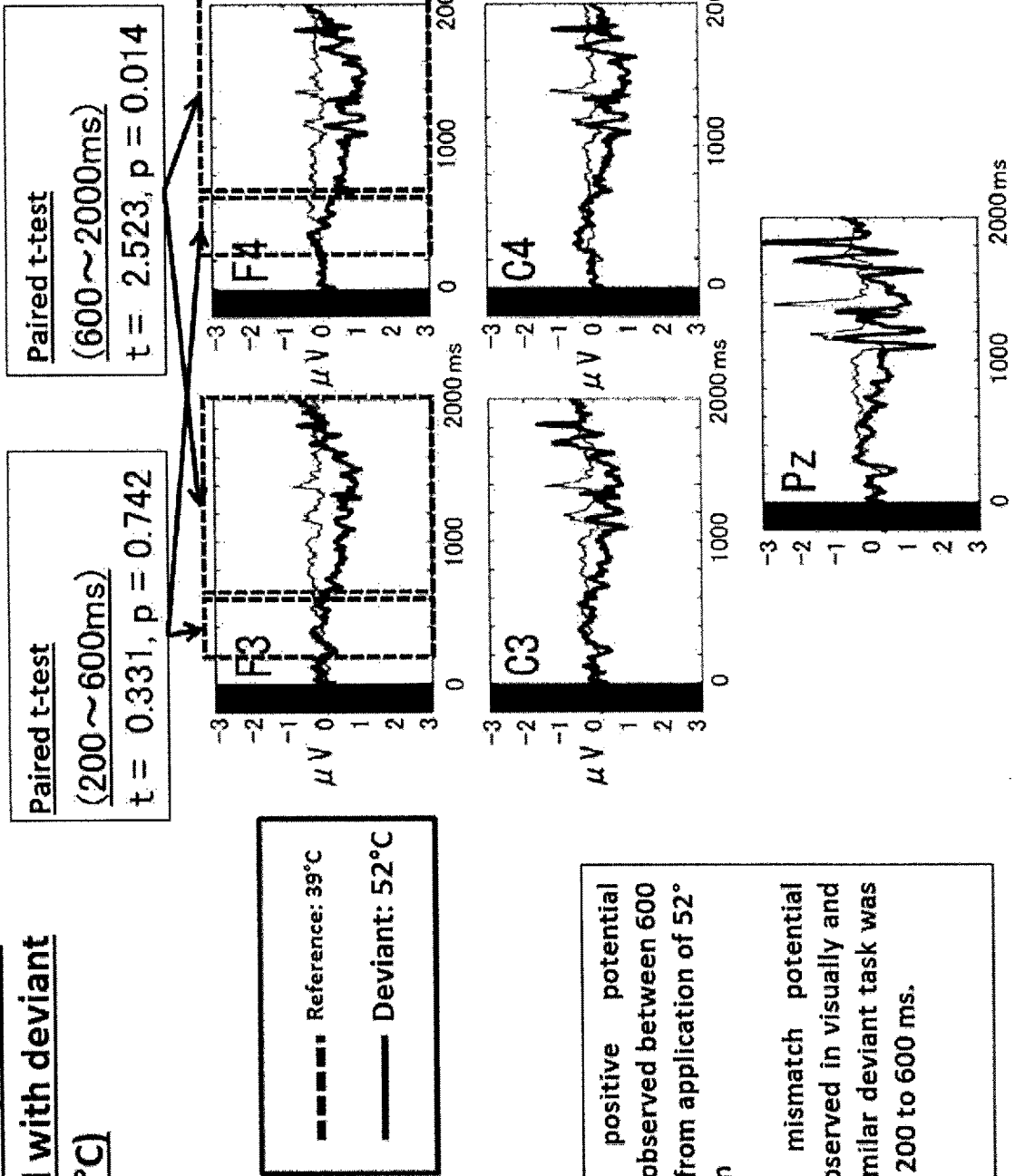
FIG. 21 shows a persistent positive potential effect, which is a persistent signal (property) observed with deviant stimulation (52° C.). A "persistent positive potential effect" was observed at 400 (F3, F4) or 600 (C3, C4) to 2000 msec from application of 52° C. stimulation. Meanwhile, mismatch potential or P300 observed in deviant tasks with similar visual or auditory perception was not significantly observed at 200 to 600 msec. The instantaneous pain paradigm randomly applied standard stimulation of 39° C. at 70% and 52° C. deviant stimulation at 30% by using a pain oddball paradigm. Subjects were instructed to count the number of pain stimulation to keep their attention to stimulation.

FIG. 21 shows an example of a persistent signal (property) found in the present invention. As can be understood at a glance, the waveform of deviant stimulation (52° C.) persistently shifted to the positive direction compared to reference stimulation (39° C.) up to the end of the epoch at 2000 msec. In view of the waveform of right frontal portion F4, the persistent effect thereof starts from about 400 msec at the earliest, and the effect continues for a very long time. When a paired t-test was performed using the mean potential of two electrodes at the frontal portions (600 to 2000 ms), a significant difference was confirmed between the conditions (t=2.523, p=0.014). Meanwhile, a significant difference was not found between the conditions in the intermediate time frame before 600 msec (200 to 600 msec) (t=0.331, p=0.742). It can be understood in view of the above results that deviant stimulation exhibited a persistent effect from the intermediate to late time frame.

Figure 22:
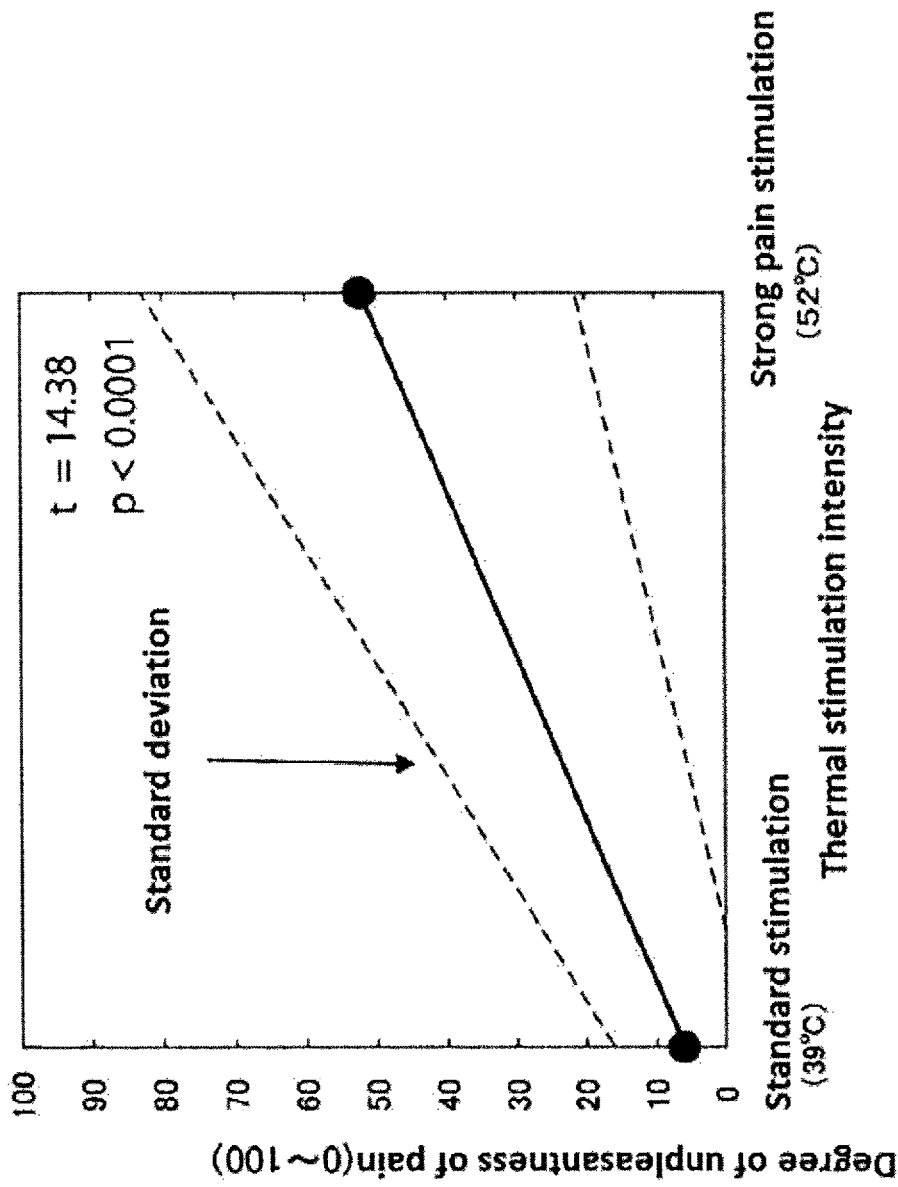
FIG. 22 shows subjective evaluation of the degree of unpleasantness of pain from standard stimulation (39° C.) and deviant stimulation (52° C.). The degree of unpleasantness is significantly higher for the 52° C. stimulation than the 39° C. stimulation. The experimental paradigm randomly applied stimulation of 39° C. and 52° C. a plurality of times. The subjects continuously evaluated the degree of unpleasantness of pain when stimulation was applied.
Figure 23:
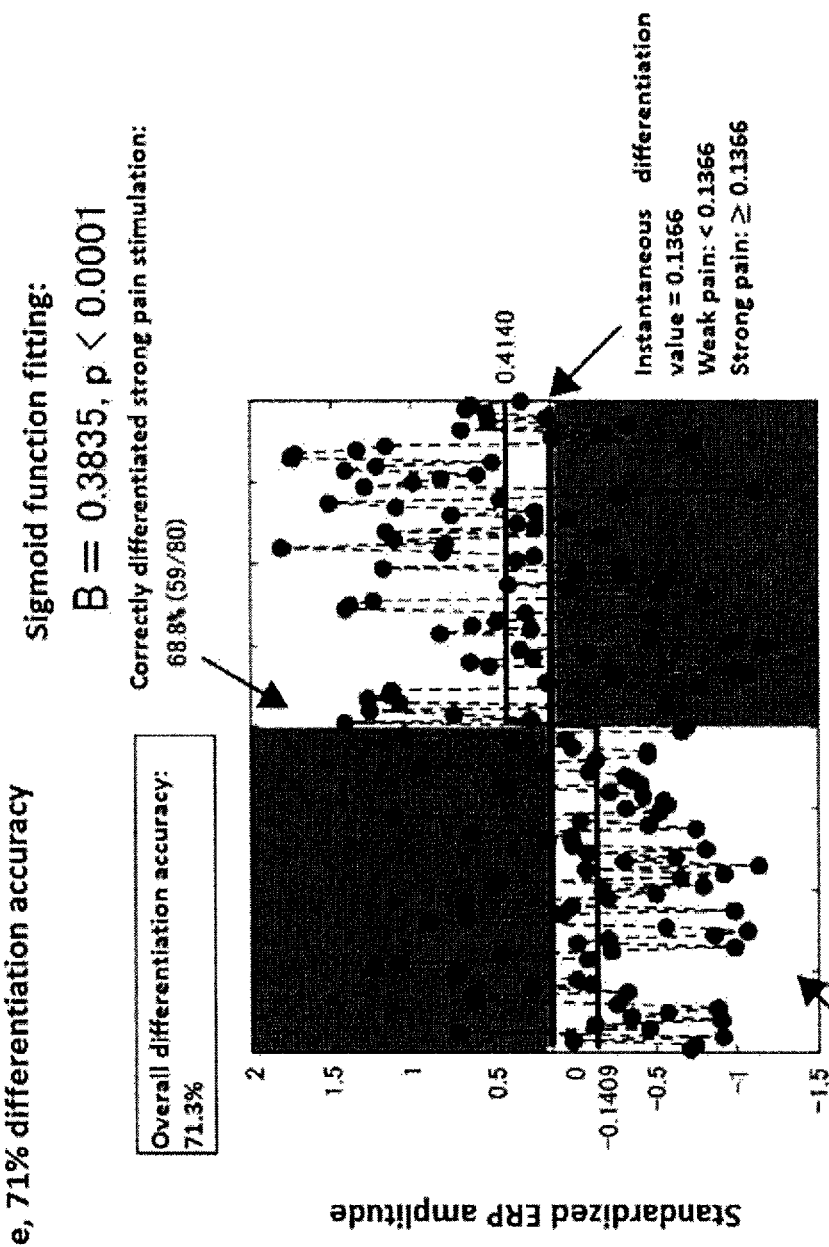
FIG. 23 shows an instantaneous pain differentiation value (inflection point in a sigmoid function). When strong and weak pain was classified using an instantaneous pain differentiation value, differentiation accuracy of 71% was exhibited. An instantaneous pain differentiation value is a value based on a persistent property.

FIG. 22 shows subjective evaluation of the degree of unpleasantness of pain from reference stimulation (39° C.) and deviant stimulation (52° C.). The degree of unpleasantness was significantly higher for the 52° C. stimulation than the 39° C. stimulation (t=14.38, p<0.0001). Thus, the persistent positive effect in the EEG analysis described above can be understood as an effect reflecting an increase in the degree of unpleasantness of strong pain stimulation.

Example 4: Differentiation/Estimation Process of Two Levels of Instantaneous Pain Using Persistent ERP Feature Instantaneous pain was differentiated and estimated using the persistent ERP feature observed in Example 1 and a LASSO (regularization) algorithm.

(Materials and Methods)

The experimental paradigm, EEG data collection, and analysis method are in accordance with Example 1. This Example performed sparse model analysis by newly using a LASSO (Least absolute shrinkage and selection operator), and calculated an optimal coefficient of a multiple regression model and a model intercept to differentiate and estimate two levels of instantaneous pain.

Figure 24:
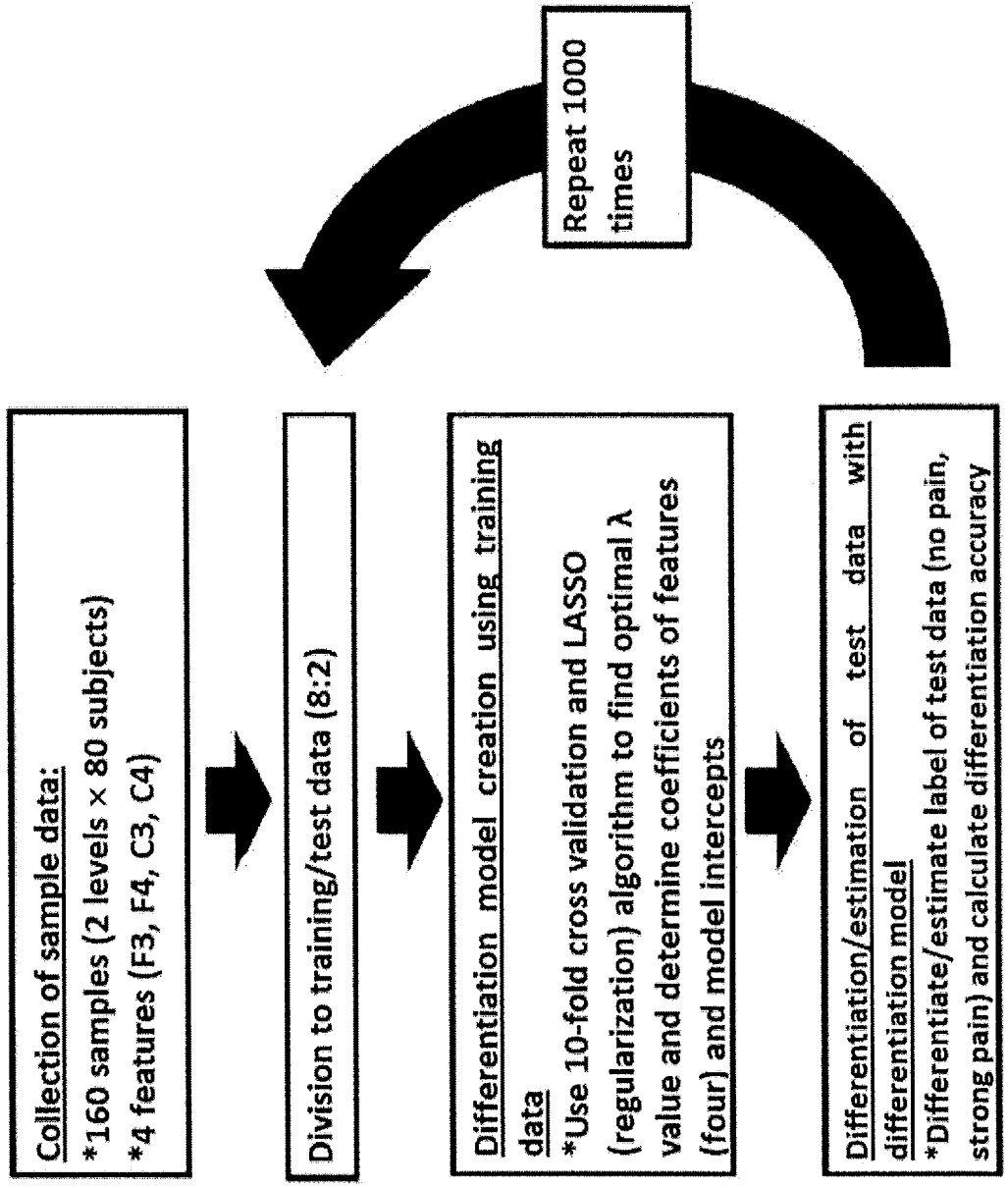
FIG. 24 shows an outline of a differentiation/estimation process of two levels of instantaneous pain. The process of the invention collects sample data (e.g., 160 samples (2 levels×80 subjects), 4 features (F3, F4, C3, C4)), divides the data into training/test data (8:2), creates a differentiation model using the training data (e.g., finds the optimal λ value and determines coefficients of the features (four) and intercept of a model by using 10-fold cross validation or LASSO (regularization) algorithm), and differentiates/estimates test data from the differentiation model (differentiates/estimates labels (no pain, strong pain) of test data to calculate differentiation accuracy).

As shown in FIG. 24, the collected data (160 samples=two levels×80 subjects) was divided into "training (learning) data" and "test data". After calculating the optimal λ using LASSO algorithm and 10-fold cross validation with the training data, a partial regression coefficients and intercepts for four features were determined. For the four features, the mean potential (standardized among individuals) of reference stimulation and strong pain stimulation from 1000 msec to 1600 msec where persistent potential is notably observed in the F3, F4, C3, and C4 electrodes was used. The λ value is a hyperparamter functioning in regularization, serving the function of smoothing the compatibility of the model and increasing the generalization capability. For regularization, L1 regularization is used. The LASSO function of MATLAB solves the following minimization problem.

Min(Dev($\beta_0$+β)+λΣ|$\beta_j$|) [Numeral 1]

Min: minimization
Dev: degree of deviation (discrepancy of a regression model estimation value using intercept $\beta_0$ and regression coefficient β from an observed value)
N: number of samples
λ: regularization parameter with a positive value In this Example, posterior distribution of differentiation accuracy was obtained by repeating the process described above 1000 times. To show that the differentiation accuracy of observed data is higher than random differentiation accuracy, the same process was used, two levels of pain were randomized, and the differentiation accuracy at the chance level was calculated for comparison and review.

(Results)

Figure 25:
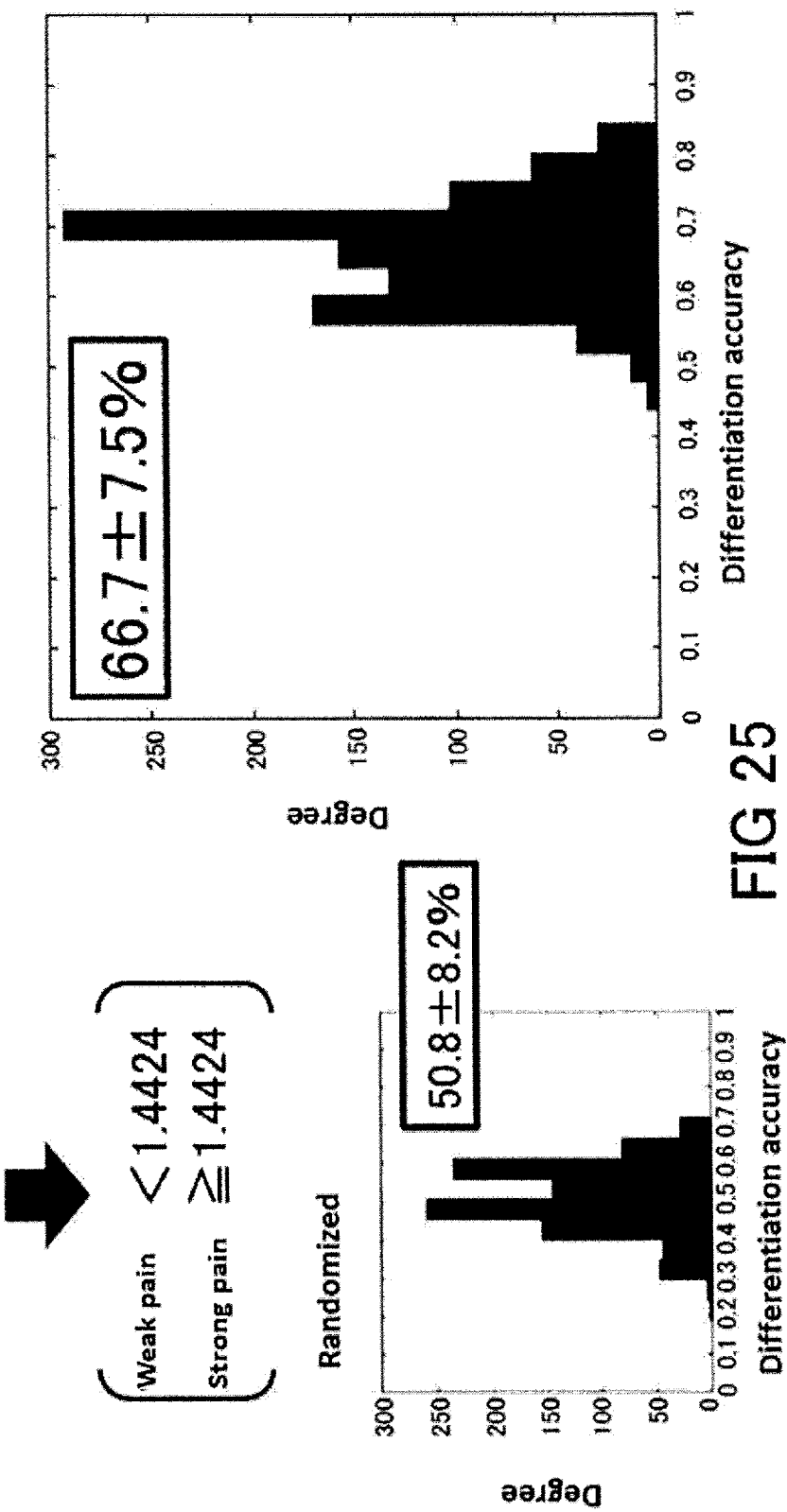
FIG. 25 shows differentiation accuracy for instantaneous pain using four persistent ERP features (amplitude of 1000 to 1600 msec) by the differentiation/estimation process in FIG. 24. In the process of FIG. 24, differentiation rate is calculated 1000 times for 1000 model validations. Differentiation accuracy of actual instantaneous pain level was about 70%, which was a nearly 20% higher numerical value compared to the differentiation accuracy at a chance level, about 51%. An estimation value is calculated using a multiple regression equation using the β coefficient and intercept found in FIG. 24. The calculated value is binomially classified into having instantaneous pain and no instantaneous pain using an intermediate value, i.e., differentiation value, and collated with actual pain levels.

FIG. 25 shows results of differentiating and estimating two levels of instantaneous pain using persistent ERP features. A differentiation model using coefficients and intercepts of four features obtained by 1000 LASSO analyses can be summarized as follows.

$$Y = 0.1659 \times F3 + 0.171 \times F4 - 0.0079 \times C3 - 0.0841 \times C4 + 0.6671 \quad \text{[Numeral 2]}$$

An instantaneous pain classifier is shows as an example of a result outputted when test data is inputted into a specific model for 1000 differentiation analyses. With a classifiere of "1.4424" as the threshold value, a value less than the threshold value was deemed weak pain or no pain (reference stimulation), and a value equal to or greater than the threshold value was deemed strong pain, and collated with actual pain levels to calculate differentiation accuracy. The results for differentiating test data 1000 times are the graph on the right side of FIG. 25. The mean differentiation accuracy was "66.7"%. This differentiation accuracy was a numerical value that is about 16% higher relative to the differentiation accuracy of "50.8%" from randomizing differentiation labels, indicating that persistent ERP features are effective for differentiating instantaneous pain.

Example 5: Comparative Example of Differentiation Models Using Non-Persistent ERP Features To further study the effectiveness of differentiating instantaneous pain using a persistent feature in Example 4, instantaneous pain was differentiated and estimated using the LASSO (regularization) algorithm and non-persistent ERP feature in Example 3.

(Materials and Methods)

The experimental paradigm, EEG data collection, EEG analysis method, and differentiation/estimation analysis are in accordance with Example 4. In this Example, a non-persistent brainwave segment from 200 msec to 600 msec was used as the feature used in differentiation/estimation.

(Results)

Figure 26:
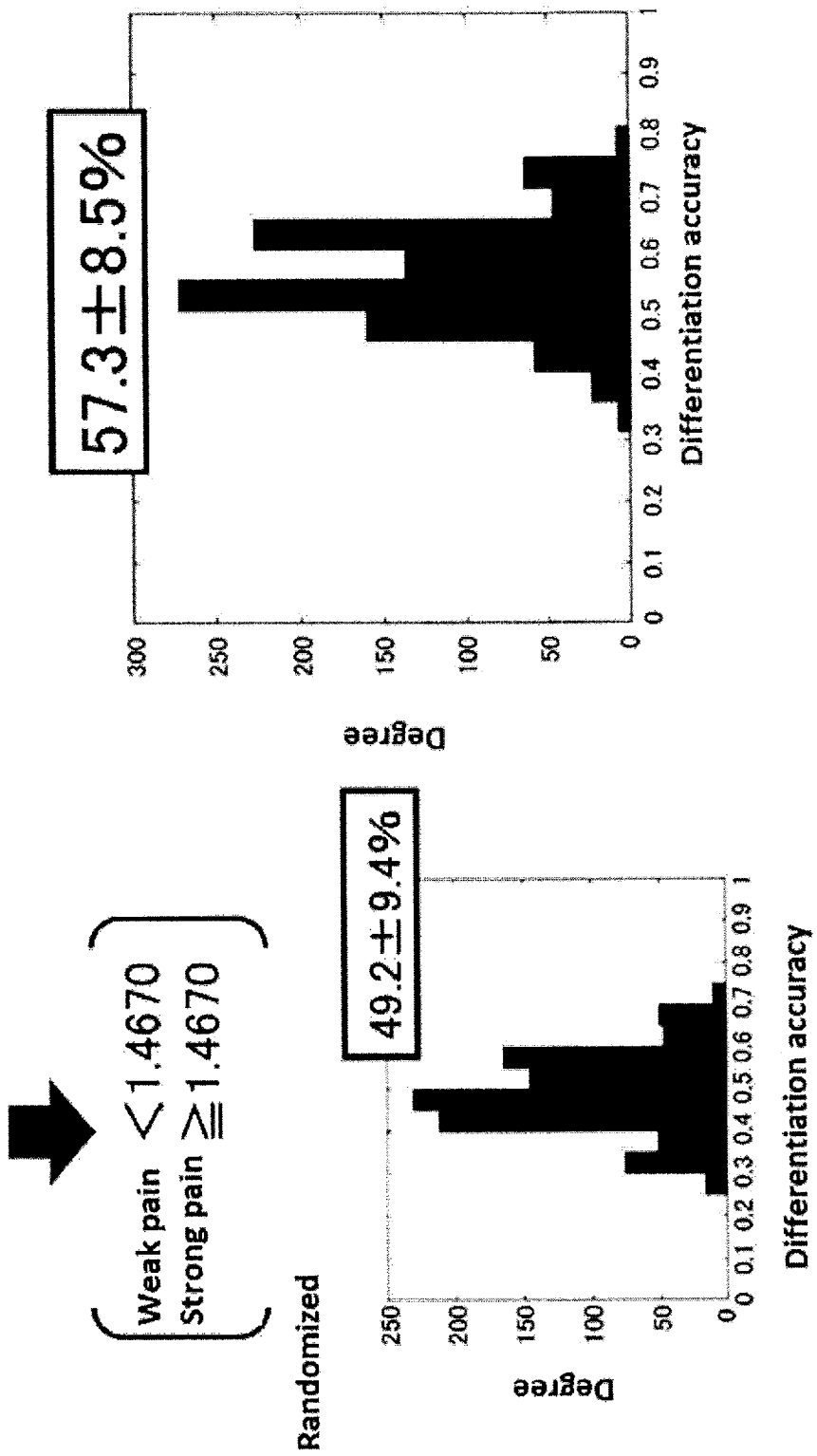
FIG. 26 shows accuracy of differentiating instantaneous pain using four non-persistent ERP features (amplitude of 200 to 600 msec) by the differentiation/estimation process in FIG. 24. In this analysis, binomial classification of having instantaneous pain and no instantaneous pain was performed using a non-persistent feature in the time segment from 200 to 600 msec that does not exhibit a persistent property by using the same differentiation test process as the Example shown in FIG. 25. The differentiation accuracy decreased about 10% compared to the differentiation accuracy using features in in a time segment exhibiting a persistent property. For differentiation accuracy of random data, similar differentiation accuracy (about 50%) is exhibited in this time segment and persistent segment.

FIG. 26 shows results of differentiating and estimating two levels of instantaneous pain using a non-persistent ERP feature. A differentiation model using coefficients and intercepts of four features obtained by LASSO analysis (1000 test data testing) can be summarized as follows.

$$Y = -0.0704 \times F3 + 0.1479 \times F4 + 0.2220 \times C3 - 0.2485 \times C4 + 1.4917 \quad \text{[Numeral 3]}$$

An instantaneous pain classifier is shown as an example of a result outputted when specific test data is inputted into a specific differentiation model. A classifier was "1.4670", which was close to the example of persistent feature with a difference of about "0.02". λ value less than the threshold value was deemed weak pain or no pain (reference stimulation), and a value equal to or greater than the threshold value was deemed strong pain, and collated with actual pain levels to calculate differentiation accuracy. The results for differentiating and analyzing 1000 times are the graph on the right side of FIG. 26. The mean differentiation accuracy was "57.3"%. This differentiation accuracy was higher than the chance level (50%) and about 8% higher relative to the differentiation accuracy of "49.2%" from randomizing differentiation labels, but about 10% lower than the differentiation accuracy using a persistent ERP feature (66.7%).

In view of the above results, this Example also shows that a persistent ERP feature is effective for differentiating two levels of instantaneous pain. The importance of a feature associated with conscious pain manifested in the intermediate to late time frame instead of the brain activity in the early time frame that is immediately manifested indicates that it is effective to find the point where physical intrusion changes to psychological intrusion for pain differentiation.

(Note)

As disclosed above, the present invention has been exemplified by the use of its preferred embodiments. However, it is understood that the scope of the present invention should be interpreted based solely on the Claims. It is also understood that any patent, patent application, and references cited herein should be incorporated herein by reference in the same manner as the contents are specifically described herein. The present application claims priority to Japanese Patent Application No. 2017-137723 (filed on Jul. 14, 2017) and Japanese Patent Application No. 2017-193501 (filed on Oct. 3, 2017) with the Japan Patent Office. The entire content thereof is incorporated herein by reference.

INDUSTRIAL APPLICABILITY

The present invention is capable of classifying instantaneous pain accurately without applying strong pain, and enables diagnosis or therapy of pain in more detail.

The present invention is also capable of determining instantaneous pain, and enables diagnosis or therapy of instantaneous pain in more detail.

REFERENCE SIGNS LIST

1000: reference stimulation unit
1500: object
2000: brainwave data obtaining unit
2500: electroencephalograph
2600: brainwave feature extraction unit
3000: differentiation model generation unit
3200: pain level differentiation/estimation (classification) unit
4000: pain visualization unit
5100: pain level differentiation/estimation system
5200: brainwave measurement unit
5250: brainwave recording sensor
5300: pain differentiation/estimation apparatus unit
5400: brainwave signal processing unit
5500: brainwave feature extraction unit
5600: pain differentiation/estimation unit
5700: pain differentiation correction unit
5800: pain level visualization unit
5900: stimulation apparatus unit
5920: reference stimulation application terminal
5940: reference stimulation generation unit
5960: reference stimulation level visualization unit
11000: stimulation application unit
11500: object
12000: brainwave data obtaining unit
12500: electroencephalograph
13000: pain determination value generation unit
14000: pain determination unit
15099: object 15100: pain determination system
15200: brainwave measurement unit
15220: electroencephalograph
15250: brainwave recording sensor
15270: brainwave amplification unit
15300: pain determination apparatus
15400: brainwave signal processing unit
15500: brainwave feature extraction unit
15600: pain determination unit
15700: pain determination value generation unit
15800: determination level visualization unit
15900: stimulation apparatus unit
15920: stimulation application unit
15960: stimulation information visualization unit

The invention claimed is:

1. A method of controlling a system for differentiating or evaluating pain, the system including an electroencephalograph having electrodes for measuring brainwave data of a subject, a memory for storing a program and reference brainwave data, and a processor for executing procedures of analyzing the measured brainwave data based on the program, the method comprising:
comparing, by the processor, the brainwave data of the subject transmitted from the electroencephalograph with the reference brainwave data read out from the memory over a predetermined period, wherein
the brainwave data of the subject is measured after application of target stimulation and during the predetermined period starting at the earliest point among i) an occurrence of evoked brainwave potential, ii) an occurrence of early event related potential, and iii) 250 msec after the application of the target stimulation, and
the reference brainwave data is measured after application of reference stimulation during the predetermined period starting at same timing as that of the brainwave data of the subject, wherein the reference stimulation is a baseline of comparison for measurement of pain and does not result in pain;
determining, by the processor, whether either one of the evoked brainwave potential and the early event related potential in the brainwave data of the subject has a duration different from that in the reference brainwave data;
determining, by the processor, upon detecting the different duration, that the brainwave data of the subject has a persistent component to indicate pain when following conditions i) and ii) are satisfied,
i) if the different duration corresponding to the persistent component is not eliminated when a standard line of the brainwave data of the subject is aligned to the baseline by linear correction, and
ii) if the persistent component is eliminated when a predetermined low frequency band component is blocked;
classifying, by the processor, the pain using a multi-level classifier, wherein the multi-level classifier is generated by sigmoid function fitting or machine learning; and
visualizing, by the processor, the degree of pain based on the classification by the multi-level classifier.

2. The method of claim 1, wherein the predetermined period has a length of 2000 msec.

3. The method of claim 1, further comprising analyzing the compared data using sigmoid function fitting.

4. A non-transitory computer-readable recording medium for storing a program for making a computer execute a method of controlling a system for differentiating or evaluating pain, the system including electroencephalograph having electrodes for measuring brainwave data of a subject and the computer, the computer including a memory for storing a program and reference brainwave data and a processor for executing procedures of analyzing the measured brainwave data based on the program, the method comprising:
comparing, by the processor, the brainwave data of the subject transmitted from the electroencephalograph with the reference brainwave data read out from the memory over a predetermined period, wherein
the brainwave data of the subject is measured after application of target stimulation and during the predetermined period starting at the earliest point among i) an occurrence of evoked brainwave potential, ii) an occurrence of early event related potential, and iii) 250 msec after the application of the target stimulation, and
the reference brainwave data is measured after application of reference stimulation during the predetermined period starting at same timing as that of the brainwave data of the subject, wherein the reference stimulation is a baseline of comparison for measurement of pain and does not result in pain;
determining, by the processor, whether either one of the evoked brainwave potential and the early event related potential in the brainwave data of the subject has a duration different from that in the reference brainwave data;
determining, by the processor, upon detecting the different duration, that the brainwave data of the subject has a persistent component to indicate pain when following conditions i) and ii) are satisfied,
i) if the different duration corresponding to the persistent component is not eliminated when a standard line of the brainwave data of the subject is aligned to the baseline by linear correction, and
ii) if the persistent component is eliminated when a predetermined low frequency band component is blocked;
classifying, by the processor, the pain using a multi-level classifier, wherein the multi-level classifier is generated by sigmoid function fitting or machine learning; and
visualizing, by the processor, the degree of pain based on the classification by the multi-level classifier.

5. A system for differentiating or evaluating pain, comprising:
an electroencephalograph having electrodes for measuring brainwave data of a subject,
a memory for storing a program and reference brainwave data, and
a processor for executing procedures of analyzing the measured brainwave data based on the program, wherein the processor is configured to:
a) compare the brainwave data of the subject transmitted from the electroencephalograph with the reference brainwave data read out from the memory over a predetermined period, wherein
the brainwave data of the subject is measured after application of target stimulation and during the predetermined period starting at the earliest point among i) an occurrence of evoked brainwave potential, ii) an occurrence of early event related potential, and iii) 250 msec after the application of the target stimulation, and
the reference brainwave data is measured after application of reference stimulation during the predetermined period starting at same timing as that of the brainwave data of the subject, wherein the reference stimulation is a baseline of comparison for measurement of pain and does not result in pain;
b) determine whether either one of the evoked brainwave potential and the early event related potential in the brainwave data of the subject has a duration different from that in the reference brainwave data;
c) determine, upon detecting the different duration, that the brainwave data of the subject has a persistent component to indicate pain when following conditions i) and ii) are satisfied,
  i) if the different duration corresponding to the persistent component is not eliminated when a standard line of the brainwave data of the subject is aligned to the baseline by linear correction, and
  ii) if the persistent component is eliminated when a predetermined low frequency band component is blocked;
d) classify the pain using a multi-level classifier, wherein the multi-level classifier is generated by sigmoid function fitting or machine learning; and
e) visualize the degree of pain based on the classification by the multi-level classifier.

\* \* \* \* \*